(12) United States Patent
Silla et al.

(10) Patent No.: US 8,377,653 B2
(45) Date of Patent: *Feb. 19, 2013

(54) VIRAL EXPRESSION PLASMIDS FOR PRODUCTION OF PROTEINS, ANTIBODIES, ENZYMES, VIRUS-LIKE PARTICLES AND FOR USE IN CELL-BASED ASSAYS

(75) Inventors: Toomas Silla, Tartu (EE); Ingrid Tagen, Tartu (EE); Anne Kalling, Tartu (EE); Radi Tegova, Tartu (EE); Mart Ustav, Tartu (EE); Tiiu Mandel, Tartu (EE); Urve Toots, Tartu (EE); Andres Tover, Tartu (EE); Aare Abroi, Tartu (EE); Ene Ustav, Tartu (EE); Jelizaveta Geimanen, Tartu (EE); Kadri Janikson, Tartu (EE)

(73) Assignee: Icosagen Cell Factory Oü, Tartu (EE)

( * ) Notice: Subject to any disclaimer, the term of this patent is extended or adjusted under 35 U.S.C. 154(b) by 74 days.

This patent is subject to a terminal disclaimer.

(21) Appl. No.: 12/803,831

(22) Filed: Jul. 7, 2010

(65) Prior Publication Data

US 2011/0076760 A1    Mar. 31, 2011

Related U.S. Application Data

(63) Continuation-in-part of application No. 11/351,809, filed on Feb. 10, 2006, now Pat. No. 7,790,446.

(51) Int. Cl.
*C12N 5/10* (2006.01)
*C12N 15/00* (2006.01)

(52) U.S. Cl. .............. 435/69.1; 435/320.1; 435/325
(58) Field of Classification Search .............. 435/69.1, 435/320.1, 325

See application file for complete search history.

(56) References Cited

U.S. PATENT DOCUMENTS

| | | | |
|---|---|---|---|
| 6,255,071 B1 * | 7/2001 | Beach et al. | 435/69.1 |
| 7,763,258 B2 | 7/2010 | Doms | |
| 7,790,446 B2 * | 9/2010 | Silla et al. | 435/320.1 |
| 7,919,270 B2 | 4/2011 | Kunaparaju | |
| 2003/0129169 A1 * | 7/2003 | Krohn et al. | 424/93.21 |
| 2006/0088819 A1 * | 4/2006 | Houghton et al. | 435/5 |

FOREIGN PATENT DOCUMENTS

WO    WO 2007/089582 A2    8/2007

OTHER PUBLICATIONS

Invitrogen (http://tools.invitrogen.com/content/sfs/productnotes/F_071215_MammalianExpressionVectors.pdf; last visited Mar. 21, 2012).*
Takamizawa et al, J. Virol. 65(3):1105-1113, 1991.*
Maarit Suomalainen and Henrik Garoff; Incorporation of Homologous and Heterologous Proteins into the Envelope of Moloney Murine Leukemia Virus; Journal of Virology, Aug. 1994, vol. 68, No. 8, p. 4879-4889.

* cited by examiner

*Primary Examiner* — Kevin K. Hill
(74) *Attorney, Agent, or Firm* — Gearhart Law, LLC

(57) ABSTRACT

This disclosure shows that the EBV FR-element comprised of EBNA1 multimeric binding sites can provide the stable maintenance replication function to the mouse polyomavirus (PyV) core origin plasmids in the presence of BPV-1 E2 protein and PyV large T-antigen (LT).

20 Claims, 36 Drawing Sheets

FR (Family of Repeats) element
EBNA-1 binding sites                    Py ori

FR (Family of Repeats) element          Py ori

1   CGGGTATCATATGCTGACTGTATATGCATG
2   AGGATAGCATATGCTACCCGGATACAGATT
3   AGGATAGCATATACTACCCAGATATAGATT
4   AGGATAGCATATGCTACCCAGATATAGATT
5   AGGATAGCCTATGCTACCCAGATATAAATT
6   AGGATAGCATATACTACCCAGATATAGATT
7   AGGATAGCATATGCTACCCAGATATAGATT
8   AGGATAGCCTATGCTACCCAGATATAGATT
9   AGGATAGCATATGCTACCCAGATATAGATT
10  AGGATAGCATATGCTATCCAGATATTT
11  TGGGTAGTATATGCTACCCAGATATAAATT
12  AGGATAGCATATACTACCCTAATCTCTATT
13  AGGATAGCATATGCTACCCGGATACAGATT
14  AGGATAGCATATACTACCCAGATATAGATT
15  AGGATAGCATATGCTACCCAGATATAGATT
16  AGGATAGCCTATGCTACCCAGATATAAATT
17  AGGATAGCATATACTACCCAGATATAGATT
18  AGGATAGCATATGCTACCCAGATATAGATA
19  AGGATAGCCTATGCTACCCAGATATAGATT
20  AGGATAGCATATGCTATCCAGATATT
21  TGGGTAGTATATGCTACCCATGGCAACATTA

Fig. 1

REPLACEMENT SHEET

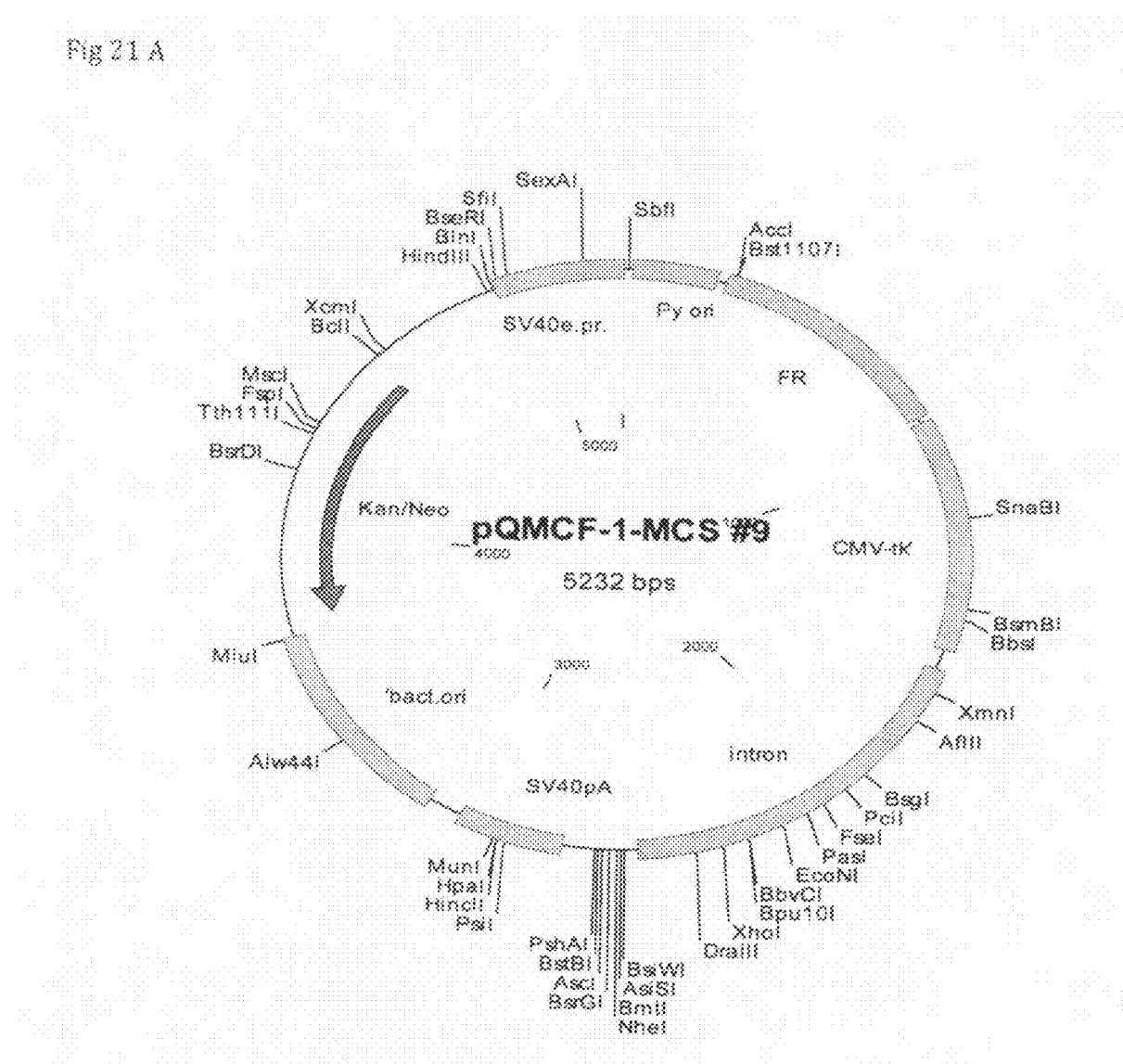

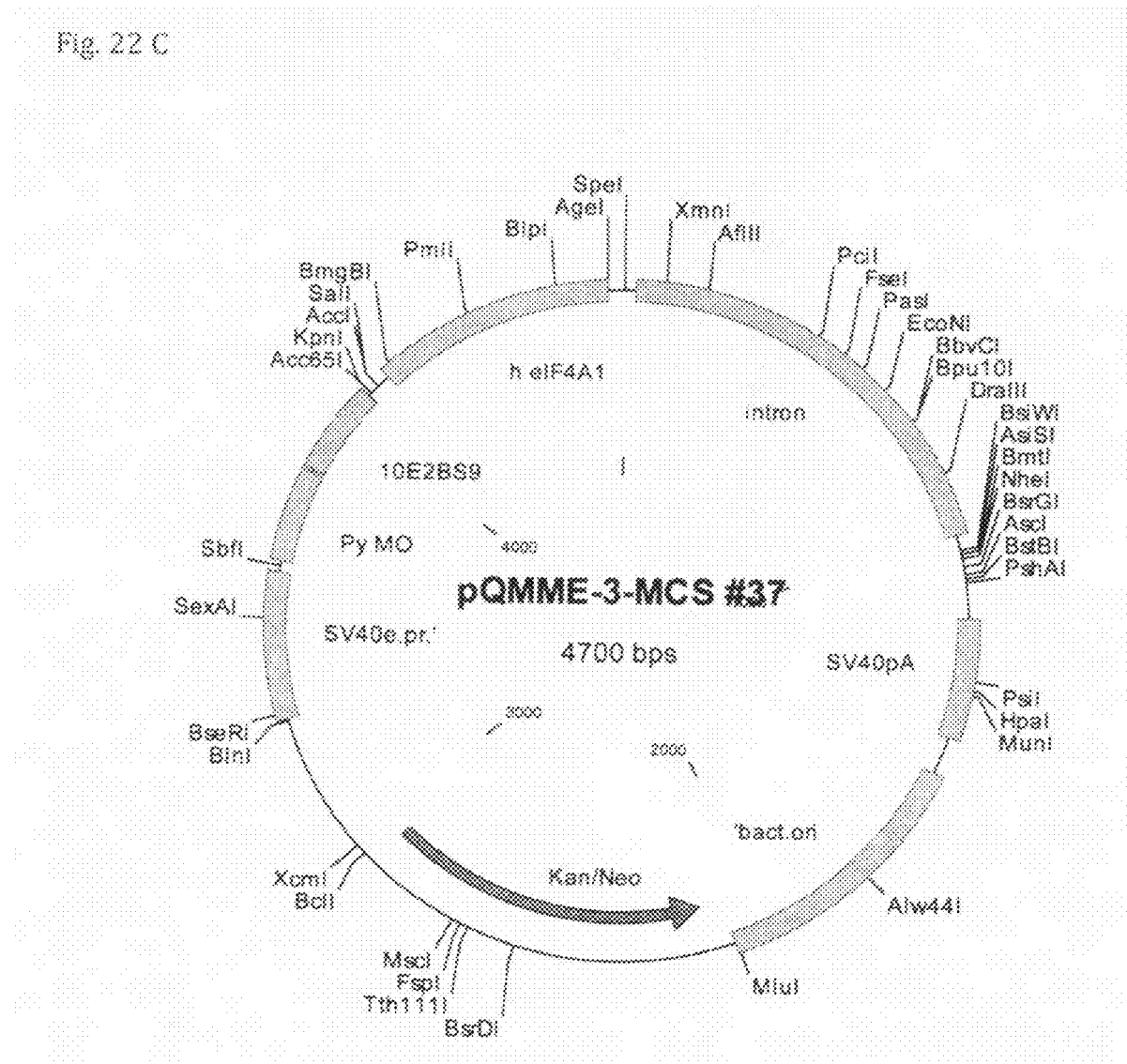

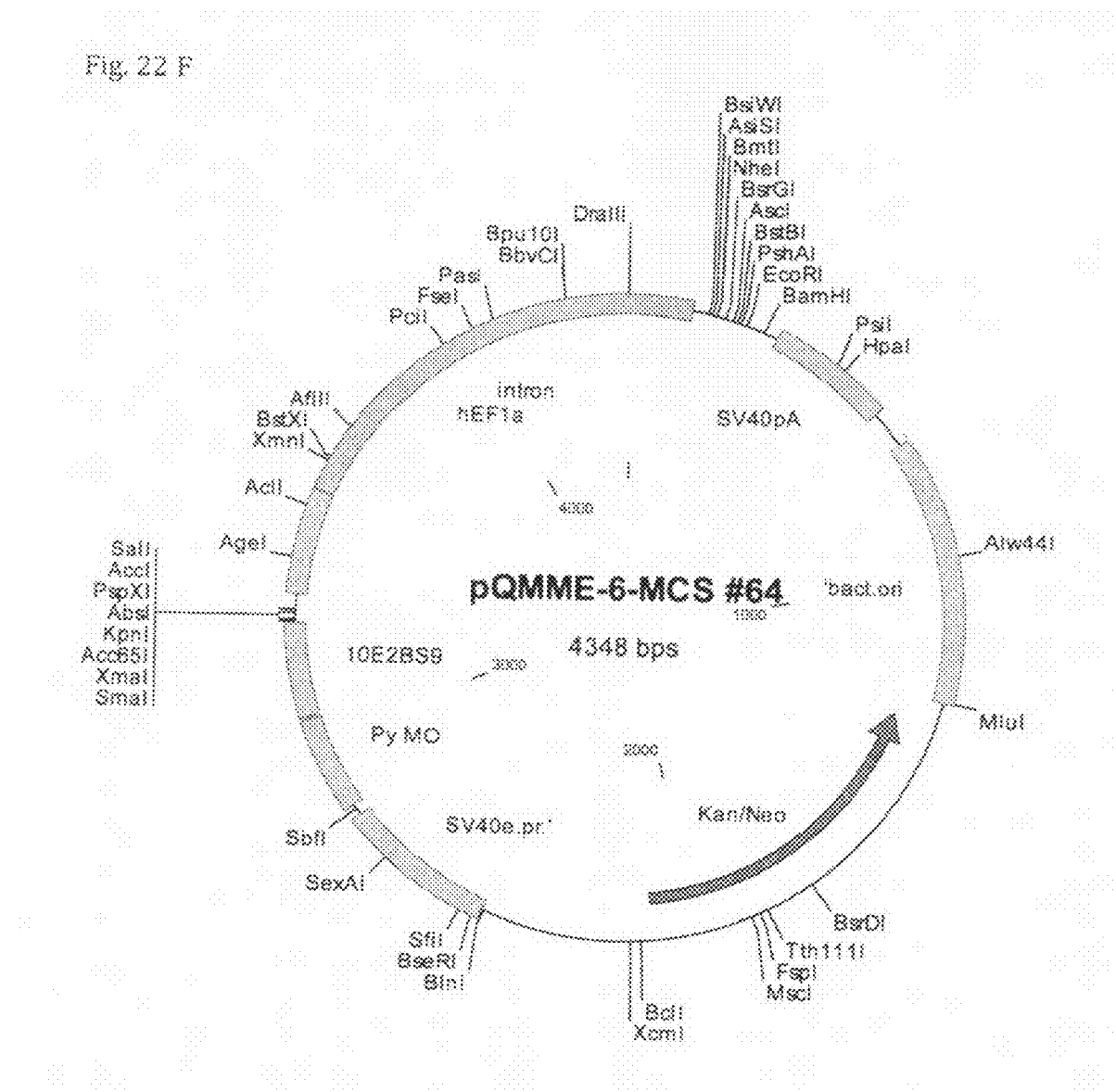

SEQUENCE LISTING

```
<160> NUMBER OF SEQ ID NOS: 44

<210> SEQ ID NO 1
<211> LENGTH: 622
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(683)
```

<223> OTHER INFORMATION: FR element

<400> SEQUENCE: 1

```
gggtatcata tgctgactgt atacgcatga ggatagcata tgctacccgg atacagatta      60
ggatagcata tactacccag atatagatta ggatagcata tgctacccag atatagatta     120
ggatagccta tgctacccag atataaatta ggatavcata tactacccag atatagatta     180
ggatagcata tgctacccag atatagatta ggatagccta tgctacccag atatagatta     240
ggatagcata tgctacccag atatagatta ggatagcata tgctatccag atatttgggt     300
agtatatgct acccatatat aaattaggat agcatatact accctaatct ctattaggat     360
agcatatgct acccggatac agattaggat agcatatact acccagatat agattaggat     420
agcatatgct acccagatat agattaggat agcctatgct acccagatat aaattaggat     480
agcatatact acccagatat agattaggat agcatatgct acccagatat agattaggat     540
agcctatgct acccagatat agattaggat agcatatgct atccagatat ttgggtagta     600
tatgctaccc atggcaacat ta                                              622
```

<210> SEQ ID NO 2
<211> LENGTH: 154
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(154)
<223> OTHER INFORMATION: PyV core origin

<400> SEQUENCE: 2

```
cctagaatgt ttccacccaa tcattactat gacaacagct gttttttta gtattaagca       60
gaggccgggg gcccctggcc tccgcttact ctggagaaaa agaagagagg cattgtagag     120
gcttccagag gcaacttgtc aaaacaggac tggc                                  154
```

<210> SEQ ID NO 3
<211> LENGTH: 19
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(19)
<223> OTHER INFORMATION: alternative EBNA1 binding site

<400> SEQUENCE: 3

```
cgggtatcat atgctgact                                                   19
```

<210> SEQ ID NO 4
<211> LENGTH: 19
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(19)
<223> OTHER INFORMATION: alternative EBNA1 binding site

<400> SEQUENCE: 4

```
aggatagcat atgctaccc                                                   19
```

<210> SEQ ID NO 5

```
<211> LENGTH: 19
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(19)
<223> OTHER INFORMATION: alternative EBNA1 binding site

<400> SEQUENCE: 5
aggatagcat atactaccc                                                19

<210> SEQ ID NO 6
<211> LENGTH: 19
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(19)
<223> OTHER INFORMATION: alternative EBNA1 binding site

<400> SEQUENCE: 6
aggatagcct atgctaccc                                                19

<210> SEQ ID NO 7
<211> LENGTH: 206
<212> TYPE: DNA
<213> ORGANISM: artificial sequence
<220> FEATURE:
<223> OTHER INFORMATION: chemically synthesised
<220> FEATURE:
<221> NAME/KEY: misc_feature
<222> LOCATION: (1)..(206)
<223> OTHER INFORMATION: MME minichromosomal maintenance  element

<400> SEQUENCE: 7
ctgtaccgtt gccggtcgga tctgtaccgt tgccggtcgg atctgtaccg ttgccggtcg    60
gatctgtacc gttgccggtc ggatctgtac cgttgccggt cggatctgta ccgttgccgg   120
tcggatctgt accgttgccg gtcggatctg taccgttgcc ggtcggatct gtaccgttgc   180
cggtcggatc tgtaccgttg ccggtc                                       206

<210> SEQ ID NO 8
<211> LENGTH: 244
<212> TYPE: DNA
<213> ORGANISM: Homo sapiens
<220> FEATURE:
<221> NAME/KEY: misc_feature
<222> LOCATION: (1)..(244)
<223> OTHER INFORMATION: hEFalfa promoter

<400> SEQUENCE: 8
gctccggtgc ccgtcagtgg gcagagcgca catcgcccac agtccccgag aagttggggg    60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag ctgaagcttc   240
gagg                                                              244

<210> SEQ ID NO 9
<211> LENGTH: 528
<212> TYPE: DNA
<213> ORGANISM: Homo sapiens
<220> FEATURE:
```

<221> NAME/KEY: misc_feature
<222> LOCATION: (1)..(528)
<223> OTHER INFORMATION: HeIF4alpha promoter

<400> SEQUENCE: 9

| | | |
|---|---|---|
| ctagatgatt tccttcatcc ctggcacacg tccaggcagt gtcgaatcca tctctgctac | 60 | |
| aggggaaaac aaataacatt tgagtccagt ggagaccggg agcagaagta aagggaagtg | 120 | |
| ataaccccca gagcccggaa gcctctggag gctgagacct cgcccccctt gcgtgatagg | 180 | |
| gcctacggag ccacatgacc aaggcactgt cgcctccgca cgtgtgagag tgcagggccc | 240 | |
| caagatggct gccaggcctc gaggcctgac tcttctatgt cacttccgta ccggcgagaa | 300 | |
| aggcgggccc tccagccaat gaggctgcgg ggcgggcctt caccttgata ggcactcgag | 360 | |
| ttatccaatg gtgcctgcgg gccggagcga ctaggaacta acgtcatgcc gagttgctga | 420 | |
| gcgccggcag gcggggccgg ggcggccaaa ccaatgcgat ggccggggcg gagtcgggcg | 480 | |
| ctctataagt tgtcgatagg cgggcactcc gccctagttt ctaaggaa | 528 | |

<210> SEQ ID NO 10
<211> LENGTH: 18
<212> TYPE: DNA
<213> ORGANISM: articial sequence
<220> FEATURE:
<221> NAME/KEY: misc_feature
<222> LOCATION: (1)..(18)
<223> OTHER INFORMATION: primer

<400> SEQUENCE: 10
agggagctac tcctgatg                                                       18

<210> SEQ ID NO 11
<211> LENGTH: 18
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(18)
<223> OTHER INFORMATION: primer

<400> SEQUENCE: 11
ctaccaccac tccgactt                                                       18

<210> SEQ ID NO 12
<211> LENGTH: 1528
<212> TYPE: DNA
<213> ORGANISM: Homo sapiens
<220> FEATURE:
<221> NAME/KEY: misc_feature
<222> LOCATION: (1)..(1528)
<223> OTHER INFORMATION: Beta actin promoter

<400> SEQUENCE: 12

| | | |
|---|---|---|
| ctagagttcc atgtccttat atggactcat ctttgcctat tgcgacacac actcaatgaa | 60 | |
| cacctactac gcgctgcaaa gagccccgca ggcctgaggt gccccacct caccactctt | 120 | |
| cctattttg tgtaaaaatc cagcttcttg tcaccacctc caaggagggg gaggaggagg | 180 | |
| aaggcaggtt cctctaggct gagccgaatg ccctctgtg gtcccacgcc actgatcgct | 240 | |
| gcatgcccac cacctgggta cacacagtct gtgattcccg gagcagaacg gaccctgccc | 300 | |
| acccggtctt gtgtgctact cagtggacag acccaaggca agaaagggtg acaaggacag | 360 | |
| ggtcttccca ggctggcttt gagttcctag caccgccccg cccccaatcc tctgtggcac | 420 | |

-continued

| | |
|---|---:|
| atggagtctt ggtccccaga gtcccccagc ggcctccaga tggtctggga gggcagttca | 480 |
| gctgtggctg cgcatagcag acatacaacg gacggtgggc ccagacccag gctgtgtaga | 540 |
| cccagccccc ccgccccgca gtgcctaggt cacccactaa cgcccaggc ctggtcttgg | 600 |
| ctgggcgtga ctgttaccct caaaagcagg cagctccagg gtaaaaggtg ccctgccctg | 660 |
| tagagcccac cttccttccc agggctgcgg ctgggtaggt ttgtagcctt catcacgggc | 720 |
| cacctccagc cactggaccg ctggcccctg ccctgtcctg gggagtgtgg tcctgcgact | 780 |
| tctaagtggc cgcaagccac ctgactcccc caacaccaca ctctacctct caagcccagg | 840 |
| tctctcccta gtgacccacc cagcacattt agctagctga ccccacagc cagaggtcct | 900 |
| caggccctgc tttcagggca gttgctctga agtcggcaag ggggagtgac tgcctggcca | 960 |
| ctccatgccc tccaagagct ccttctgcag gagcgtacag aacccagggc cctggcaccc | 1020 |
| gtgcagaccc tggcccaccc cacctgggcg ctcagtgccc aagagatgtc cacacctagg | 1080 |
| atgtcccgcg gtgggtgggg ggcccgagag acgggcaggc cggggcagg cctggccatg | 1140 |
| cggggccgaa ccgggcactg cccagcgtgg ggcgcgggg ccacggcgcg cgcccccagc | 1200 |
| ccccgggccc agcaccccaa ggcggccaac gccaaaactc tccctcctcc tcttcctcaa | 1260 |
| tctcgctctc gctctttttt tttttcgcaa aaggagggga gaggggtaa aaaaatgctg | 1320 |
| cactgtgcgg cgaagccggt gagtgagcgg cgcggggcca atcagcgtgc gccgttccga | 1380 |
| aagttgcctt ttatggctcg agcggccgcg gcggcgccct ataaacccca gcggcgcgac | 1440 |
| gcgccaccac cgccgagacc gcgtccgccc cgcgagcaca gagcctcgcc tttgccgatc | 1500 |
| cgccgcccgt ccacacccgc cgaccggt | 1528 |

<210> SEQ ID NO 13
<211> LENGTH: 606
<212> TYPE: DNA
<213> ORGANISM: Human cytomegalovirus
<220> FEATURE:
<221> NAME/KEY: misc_feature
<222> LOCATION: (1)..(606)
<223> OTHER INFORMATION: promoter

<400> SEQUENCE: 13

| | |
|---|---:|
| ggctggatcg gtcccggtgt cttctatgga ggtcaaaaca gcgtggatgg cgtctccagg | 60 |
| cgatctgacg gttcactaaa cgagctctgc ttatatagac ctcccaccgt acacgcctac | 120 |
| cgcccatttg cgtcaatggg gcggagttgt tacgacattt ggaaagtcc cgttgatttt | 180 |
| ggtgccaaaa caaactccca ttgacgtcaa tggggtggac acttggaaat ccccgtgagt | 240 |
| caaaccgcta tccacgccca ttgatgtact gccaaaaccg catcaccatg gtaatagcga | 300 |
| tgactaatac gtagatgtac tgccaagtag gaaagtccca taaggtcatg tactgggcat | 360 |
| aatgccaggc gggccattta ccgtcattga cgtcaatagg gggcgtactt ggcatatgat | 420 |
| acacttgatg tactgccaag tgggcagttt accgtaaata ctccacccat tgacgtcaat | 480 |
| ggaaagtccc tattggcgtt actatgggaa catacgtcat tattgacgtc aatgggcggg | 540 |
| ggtcgttggg cggtcagcca ggcgggccat ttaccgtaag ttatgtaacg gggcgagctc | 600 |
| gaattc | 606 |

<210> SEQ ID NO 14
<211> LENGTH: 532
<212> TYPE: DNA
<213> ORGANISM: artificial sequence
<220> FEATURE:
<223> OTHER INFORMATION: chemically synthesized
<220> FEATURE:

<221> NAME/KEY: misc_feature
<222> LOCATION: (1)..(532)
<223> OTHER INFORMATION: HEF1 alpha HTLV promoter

<400> SEQUENCE: 14

```
gctccggtgc cgtcagtgg gcagagcgca catcgcccac agtccccgag aagttggggg      60
gaggggtcgg caattgaacc ggtgcctaga aaggtggcg cggggtaaac tgggaaagtg     120
atgtcgtgta ctggctccgc cttttttccg agggtgggg agaaccgtat ataagtgcag     180
tagtcgccgt gaacgttctt tttcgcaacg ggtttgccgc cagaacacag ctgaagcttc    240
gagggggctcg catctctcct tcacgcgccc gccgccctac ctgaggccgc catccacgcc    300
ggttgagtcg cgttctgccg cctcccgcct gtggtgcctc ctgaactgcg tccgccgtct    360
aggtaagttt aaagctcagg tcgagaccgg gcctttgtcc ggcgctccct tggagcctac    420
ctagactcag ccggctctcc acgctttgcc tgaccctgct tgctcaactc tacgtctttg    480
tttcgttttc tgttctgcgc cgttacagat ccaagctgtg accggcgcct ac            532
```

<210> SEQ ID NO 15
<211> LENGTH: 269
<212> TYPE: DNA
<213> ORGANISM: simian virus
<220> FEATURE:
<221> NAME/KEY: misc_feature
<222> LOCATION: (1)..(269)
<223> OTHER INFORMATION: SV40 polyA

<400> SEQUENCE: 15

```
aattaacatt taaatgatct accacatttg tagaggtttt acttgcttta aaaaacctcc     60
cacacctccc cctgaacctg aaacataaaa tgaatgcaat tgttgttgtt aacttgttta    120
ttgcagctta taatggttac aaataaagca atagcatcac aaatttcaca aataaagcaa    180
tagcatcaca aatttcacaa ataaagcatt ttttcactg cattctagtt gtggtttgtc    240
caaactcatc aatgtatctt atcatgtcg                                     269
```

<210> SEQ ID NO 16
<211> LENGTH: 527
<212> TYPE: DNA
<213> ORGANISM: Rous sarcoma virus
<220> FEATURE:
<221> NAME/KEY: misc_feature
<222> LOCATION: (1)..(527)
<223> OTHER INFORMATION: RV-LTR promoter

<400> SEQUENCE: 16

```
ctgctccctg cttgtgtgtt ggaggtcgct gagtagtgcg cgagcaaaat ttaagctaca     60
acaaggcaag gcttgaccga caattgcatg aagaatctgc ttagggttag gcgttttgcg    120
ctgcttcgcg atgtacgggc cagatatacg cgtatctgag gggactaggg tgtgtttagg    180
cgaaaagcgg ggcttcggtt gtacgcggtt aggagtcccc tcaggatata gtagtttcgc    240
ttttgcatag ggagggggaa atgtagtctt atgcaatact cttgtagtct tgcaacatgg    300
taacgatgag ttagcaacat gccttacaag gagagaaaaa gcaccgtgca tgccgattgg    360
tggaagtaag gtggtacgat cgtgccttat taggaaggca acagacgggt ctgacatgga    420
ttggacgaac cactgaattc cgcattgcag agatattgta tttaagtgcc tagctcgata    480
caataaacgc catttgacca ttcaccacat tggtgtgcac ctccaag                  527
```

<210> SEQ ID NO 17
<211> LENGTH: 330
<212> TYPE: DNA

<213> ORGANISM: simian virus
<220> FEATURE:
<221> NAME/KEY: misc_feature
<222> LOCATION: (1)..(330)
<223> OTHER INFORMATION: SC early promoter

<400> SEQUENCE: 17

```
aggcctccaa aaaagcctcc tcactacttc tggaatagct cagaggccga ggcggcctcg     60
gcctctgcat aaataaaaaa aattagtcag ccatggggcg gagaatgggc ggaactgggc    120
ggagttaggg gcgggatggg cggagttagg ggcgggacta tggttgctga ctaattgaga    180
tgcatgcttt gcatacttct gcctgctggg gagcctgggg actttccaca cctggttgct    240
gactaattga gatgcatgct ttgcatactt ctgcctgctg gggagcctgg ggactttcca    300
caccctaact gacacacatt ccacagggtc                                     330
```

<210> SEQ ID NO 18
<211> LENGTH: 795
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(795)
<223> OTHER INFORMATION: Km/Neo resistance sequence

<400> SEQUENCE: 18

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcaaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

<210> SEQ ID NO 19
<211> LENGTH: 943
<212> TYPE: DNA
<213> ORGANISM: Homo sapiens
<220> FEATURE:
<221> NAME/KEY: misc_feature
<222> LOCATION: (1)..(943)
<223> OTHER INFORMATION: intron

<400> SEQUENCE: 19

```
ctgaaatgga agaaaaaaac tttgaaccac tgtctgaggc ttgagaatga accaagatcc     60
aaactcaaaa aggcaaatt ccaaggagaa ttcatcaag tgccaagctg gcctaacttc    120
agtctccacc cactcagtgt ggggaaactc catcgcataa aaccctcc cccaacctaa    180
```

```
agacgacgta ctccaaaagc tcgagaacta atcgaggtgc ctggacggcg cccggtactc    240
cgtggagtca catgaagcga cggctgagga cggaaaggcc ttttcctttt gtgtgggtga    300
ctcacccgcc cgctctcccg agcgccgcgt cctccatttt gagctccctg cagcagggcc    360
gggaagcggc catctttccg ctcacgcaac tggtgccgac cgggccagcc ttgccgccca    420
gggcggggcg atacacggcg gcgcgaggcc aggcaccaga gcaggccggc cagcttgaga    480 ctaccccgt ccgattctcg gtggccgcgc tcgcaggccc cgcctcgccg aacatgtgcg     540
ctgggacgca cgggccccgt cgccgcccgc ggccccaaaa accgaaatac cagtgtgcag    600
atcttggccc gcatttacaa gactatcttg ccagaaaaaa agcgtcgcag caggtcatca    660
aaaattttaa atggctagag acttatcgaa agcagcgaga caggcgcgaa ggtgccacca    720
gattcgcacg cggcggcccc agcgcccaag ccaggcctca actcaagcac gaggcgaagg    780
ggctccttaa gcgcaaggcc tcgaactctc ccacccactt ccaacccgaa gctcgggatc    840
aagaatcacg tactgcagcc aggggcgtgg aagtaattca aggcacgcaa gggccataac    900
ccgtaaagag gccaggcccg cgggaaccac acacggcact tac                      943
```

<210> SEQ ID NO 20
<211> LENGTH: 10
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(10)
<223> OTHER INFORMATION: tag sequence

<400> SEQUENCE: 20

Thr Val Lys Ala Lys Leu Leu Ser Val Glu
1               5                   10

<210> SEQ ID NO 21
<211> LENGTH: 10
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(10)
<223> OTHER INFORMATION: tag sequence

<400> SEQUENCE: 21

Ser Ser Thr Ser Ser Asp Phe Arg Asp Arg
1               5                   10

<210> SEQ ID NO 22
<211> LENGTH: 15
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(15)
<223> OTHER INFORMATION: tag sequences

<400> SEQUENCE: 22

Thr Pro Gln Asp Leu Asn Thr Met Leu Asn Thr Val Gly Gly His
1               5                   10                  15

<210> SEQ ID NO 23
<211> LENGTH: 20

```
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(20)
<223> OTHER INFORMATION: TAG-sequence

<400> SEQUENCE: 23

Leu Ser Ser Lys Ala Val Asn His Ile Arg Ser Val Trp Lys Asp Leu
1               5                   10                  15

Leu Glu Asp Thr
            20

<210> SEQ ID NO 24
<211> LENGTH: 2025
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(2025)

<400> SEQUENCE: 24
```

| | | | | | |
|---|---|---|---|---|---|
| ttacttgtac | agctcgtcca | tgccgagagt | gatcccggcg | gcggtcacga | actccagcag | 60 |
| gaccatgtga | tcgcgcttct | cgttggggtc | tttgctcagg | gcggactggg | tgctcaggta | 120 |
| gtggttgtcg | ggcagcagca | cggggccgtc | gccgatgggg | gtgttctgct | ggtagtggtc | 180 |
| ggcgagctgc | acgctgccgt | cctcgatgtt | gtggcggatc | ttgaagttca | ccttgatgcc | 240 |
| gttcttctgc | ttgtcggcca | tgatatagac | gttgtggctg | ttgtagttgt | actccagctt | 300 |
| gtgccccagg | atgttgccgt | cctccttgaa | gtcgatgccc | ttcagctcga | tgcggttcac | 360 |
| cagggtgtcg | ccctcgaact | tcacctcggc | gcgggtcttg | tagttgccgt | cgtccttgaa | 420 |
| gaagatggtg | cgctcctgga | cgtagccttc | gggcatggcg | gacttgaaga | agtcgtgctg | 480 |
| cttcatgtgg | tcggggtagc | ggctgaagca | ctgcacgccg | taggtcaggg | tggtcacgag | 540 |
| ggtgggccag | ggcacgggca | gcttgccggt | ggtgcagatg | aacttcaggg | tcagcttgcc | 600 |
| gtaggtggca | tcgccctcgc | cctgccggga | cacgctgaac | ttgtggccgt | ttacgtcgcc | 660 |
| gtccagctcg | accaggatgg | gcaccacccc | ggtgaacagc | tcctcgccct | tgctcaccat | 720 |
| tttgtcgtca | tcgtctttgt | agtcgttcat | gctgtcctta | tggctgctcc | ggtctgtgtt | 780 |
| gtggttgttt | tgatcgtggt | tcttccactg | gatgcttgtt | ccgttcatgg | ggaccgaggt | 840 |
| catcagactt | ttggactggt | aacagcagca | gcagaggcat | gactggaaac | aattttttaaa | 900 |
| tttcttgctc | acaaaataca | gagctatggg | gtttatacat | gaattcatgg | ttgccaagtt | 960 |
| aataccgatg | taatccatga | gcagtaagaa | actaagtaat | tcacatcggt | tcttgtccat | 1020 |
| ctcgttatac | acagttttct | tcaatatacg | gcttaaatga | agagggaacc | agcaaagagc | 1080 |
| aaaaattaca | accaagcaga | aaactgtttt | tgccacttct | cgacgctgct | taagatgttc | 1140 |
| actgagggca | attctcaagc | tgccattcct | tctgttcaac | atctcacaag | tcatgagggt | 1200 |
| gtagaagatc | gcagtgcaca | ccaagggcat | acagaaatag | aacccgaaga | gccaccagtc | 1260 |
| ctttacatct | tggtagaact | ccatgaattt | tgatgtggca | ttgagcatac | aggttttatg | 1320 |
| ctgttcaccc | ctatattcaa | agggtaccat | gacgaagcca | atcgcttcag | gaatggccag | 1380 |
| gataaaggac | aggatccaga | tggagacaat | ttcaatggca | gttaccaaag | gaatcccaat | 1440 |
| tccctgaaca | cgactccagg | aggcaactgc | tctgtacctg | tcaacactaa | gagcgcagag | 1500 |

| | |
|---|---|
| gttgaggacg gtgatcccca ccgaggactt ctgcaaaaag gggaacagct tgcaaagaaa | 1560 |
| tacgccaaag tcattgtgat caaaaggcca gcgcccagcc agcagcttaa atacattgat | 1620 |
| agggagatca atgaccacat agataaggtc tccaagggca agactggcta tcagcgcgtt | 1680 |
| ggggccattc ctcatacatt tgttctggta aatgatcctg agcagagttg cattccccac | 1740 |
| cattcccacg atgaaaatag tacaagatat cacagtgtta atgtatttga aagctgaagt | 1800 |
| aattttagtc tgctgtgggc aatagttgtg cattgagcca ttgctgggta ggaccaaatt | 1860 |
| agtgggttga tgagtggtaa ccaggaagct gagctctgtg ccacgaaaag tggtgaaatc | 1920 |
| atccacatga ttgcttagat ttgtgctgta tctctcagga ttatcactga ttacacatcc | 1980 |
| aaccagtgcc agccaaaagg atgccctgag gcaaagggtt tccat | 2025 |

<210> SEQ ID NO 25
<211> LENGTH: 584
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(584)
<223> OTHER INFORMATION: pMB1 origin of replication

<400> SEQUENCE: 25

| | |
|---|---|
| gcgttgctgg cgttttttcca taggctccgc cccccctgacg agcatcacaa aaatcgacgc | 60 |
| tcaagtcaga ggtggcgaaa cccgacagga ctataaagat accaggcgtt tccccctgga | 120 |
| agctccctcg tgcgctctcc tgttccgacc ctgccgctta ccggatacct gtccgccttt | 180 |
| ctcccttcgg gaagcgtggc gctttctcat agctcacgct gtaggtatct cagttcggtg | 240 |
| taggtcgttc gctccaagct gggctgtgtg cacgaacccc ccgttcagcc cgaccgctgc | 300 |
| gccttatccg gtaactatcg tcttgagtcc aacccggtaa gacacgactt atcgccactg | 360 |
| gcagcagcca ctggtaacag gattagcaga gcgaggtatg taggcggtgc tacagagttc | 420 |
| ttgaagtggt ggcctaacta cggctacact agaagaacag tatttggtat ctgcgctctg | 480 |
| ctgaagccag ttaccttcgg aaaaagagtt ggtagctctt gatccggcaa acaaaccacc | 540 |
| gctggtagcg gtggtttttt tgtttgcaag cagcagatta cgcg | 584 |

<210> SEQ ID NO 26
<211> LENGTH: 1433
<212> TYPE: DNA
<213> ORGANISM: HIV
<220> FEATURE:
<221> NAME/KEY: misc_feature
<222> LOCATION: (1)..(1433)
<223> OTHER INFORMATION: scrgag protein cDNA

<400> SEQUENCE: 26

| | |
|---|---|
| atgggatcct ccaagagtaa gcccaaggac cacatcgtgt gggccagccg cgagctggag | 60 |
| cgcttcgccg tgaaccccgg cctgctcgag accagcgaag gctgccgcca gatcatgggc | 120 |
| cagctccagc ccagcctcca gaccggcagc gaggagctgc gcagcctgta caacaccgtg | 180 |
| gccaccctgt actgcgtgca ccagaagatc gaggtgaagg acaccaagga ggccctggac | 240 |
| aaggtggagg aggagcagaa caacagcaag aagaaggccc agcaggaggc cgccgacgcc | 300 |
| ggcaaccgca accaagtcag ccagaactac cccatcgtgc agaacctgca gggccagatg | 360 |
| gtgcaccagg ccatcagccc ccgcacccta aacgcctggg tgaaggtggt ggaggagaag | 420 |
| gccttcagcc ccgaggtgat ccccatgttc agcgccctga gcgagggcgc taccccccag | 480 |

```
gacctgaaca ccatgctgaa caccgtgggc ggccaccagg ccgccatgca gatgctgaag    540
gagaccatca acgaggaggc cgccgagtgg gaccgcctgc accccgtgca cgccgggccc    600 atcgccccg gccagatgcg cgagccccgc ggcagcgaca tcgccggcac caccagcacc     660
ctccaggagc agatcggctg gatgaccaac aaccccccca tccccgtggg cgagatctac    720
aagcgctgga tcatcctggg cctgaacaag atcgtccgca tgtacagccc caccagcatc    780
ctggacatca gcagggccc caaggagccc ttccgcgact acgtggaccg cttctacaag     840
accctgcgcg ccgagcaggc cacccaggag gtgaagaact ggatgaccga gaccctgctg    900
gtgcagaacg ccaaccccga ctgcaagacc atcctcaagg ccctgggacc cgccgccacc    960
ctggaggaga tgatgaccgc ctgccaaggc gtgggaggcc caggccacaa ggccagagtg   1020
ctggccgagg ccatgagcca ggtgaccggc agcgctgcca tcatgatgca gagaggcaac   1080
ttcagaaacc agagaaagac cgtgaagtgc ttcaactgcg gcaaggaggg acacatcgcc   1140
agaaactgca gagctcccag aaagaagggc tgctggaagt gcggaaagga gggacaccag   1200
atgaaggact gcaccgagag acaggccaac ttcctgggca agatctggcc cagccacaag   1260
ggcagacccg gcaacttcct gcagagcaga cccgagccca ccgctcctcc cgaggagagc   1320
ttcagattcg gcgaggccac cgctcctagc cagaagcagg agcccatcga caaggagctg   1380
tacccactgg ccagcctgaa gagcctgttc ggcagcgacc caagcagcca gat          1433
```

<210> SEQ ID NO 27
<211> LENGTH: 72
<212> TYPE: DNA
<213> ORGANISM: foot and mouth disease virus
<220> FEATURE:
<221> NAME/KEY: misc_feature
<222> LOCATION: (1)..(72)
<223> OTHER INFORMATION: 2 A-peptide encoding sequence

<400> SEQUENCE: 27

```
gcaccggtga aacagacttt gaattttgac cttctcaagt tggcgggaga cgtggagtcc     60
aaccctgggc cc                                                         72
```

<210> SEQ ID NO 28
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 28

```
aggatagcat atgctaccc                                                  19
```

<210> SEQ ID NO 29
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)

<400> SEQUENCE: 29

```
aggatagcat atactaccc                                                  19
```

```
<210> SEQ ID NO 30
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 30
aggatagcat atgctaccc                                               19

<210> SEQ ID NO 31
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 31
aggatagcct atgctaccc                                               19

<210> SEQ ID NO 32
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 32
aggatagcat atgctaccc                                               19

<210> SEQ ID NO 33
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 33
aggatagcat atgctatcc                                               19

<210> SEQ ID NO 34
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 34
tgggtagtat atgctaccc                                               19
```

```
<210> SEQ ID NO 35
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 35
aggatagcat atactaccc                                               19

<210> SEQ ID NO 36
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 36
aggatagcat atgctaccc                                               19

<210> SEQ ID NO 37
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 37
aggatagcat atactaccc                                               19

<210> SEQ ID NO 38
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 38
aggatagcat atgctaccc                                               19

<210> SEQ ID NO 39
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 39
aggatagcct atgctaccc                                               19
```

```
<210> SEQ ID NO 40
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 40
aggatagcat atactaccc                                              19

<210> SEQ ID NO 41
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 41
aggatagcat atgctaccc                                              19

<210> SEQ ID NO 42
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 42
aggatagcct atgctaccc                                              19

<210> SEQ ID NO 43
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 43
aggatagcat atgctatcc                                              19

<210> SEQ ID NO 44
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: alternative EBNA1 binding site

<400> SEQUENCE: 44
tgggtagtat atgctaccc                                              19
```

VIRAL EXPRESSION PLASMIDS FOR PRODUCTION OF PROTEINS, ANTIBODIES, ENZYMES, VIRUS-LIKE PARTICLES AND FOR USE IN CELL-BASED ASSAYS

PRIORITY

This application claims priority of non provisional patent application Ser. No. 11/351,809 which was filed on Feb. 10, 2006 now U.S. Pat. No. 7,790,446 and of which this is a continuation-in-part.

SEQUENCE LISTING

This application contains sequence data provided on a computer readable diskette and as a paper version. The paper version of the sequence data is identical to the data provided on the diskette.

TECHNICAL FIELD OF THE INVENTION

The present invention relates to production of proteins, antibodies, enzymes and virus like particles in novel engineered animal and human cell lines using eukaryotic hybrid replication origin carrying extrachromosomally replicating expression plasmids. The present invention also relates to short term production of the proteins of interest for research purposes lasting up to 14 days. The present invention also relates to production of the proteins of interest using stable long term extrachromosomal replication of hybrid expression plasmid in engineered eukaryotic cell lines in large quantities in bioreactors or fermentors. The present invention also relates to use of long term extrachromosomal replication of the hybrid expression plasmids in engineered animal and human cells lines for providing expression of the proteins at physiological level in the form of epitope-tagged proteins for the purpose designing cell-based assays for identification of the active drug candidates using High Content Analysis.

BACKGROUND OF THE INVENTION

Several eukaryotic DNA viruses maintain their genomes as extrachromosomal multicopy nuclear episomes in proliferating host cells. Such episomal maintenance is characteristic of latent infection of the Bovine papillomavirus type 1 (BPV-1), Epstein-Barr Virus (EBV) as well as for Kaposi sarcoma associated Human herpesvirus type 8 (HHV8). The latency of the viral genome in dividing cell population requires activity of the viral genome at the two phases of the cell cycle: the viral genome replication during the S phase and proper segregation and partitioning of the replicated genomes into daughter cells during the host cell mitosis. For BPV-1 and two members of the gammaherpesvirus family—EBV and HHV8 an effective segregation of viral genomes into daughter cells and nuclear retention during mitosis is mediated through a single viral protein serving as a molecular linker, which attaches viral genomes to the host mitotic chromosomes. This linker protein is a viral regulatory protein E2 for BPV-1, viral transactivator EBNA1 for EBV and viral transcription repressor LANA1 for HHV8.

For initiation of the BPV-1 DNA replication in vivo, minimal origin region in cis and two viral proteins—E1 and E2, in trans, are absolutely essential. However, the minimal origin (MO) is not sufficient for stable extrachromosomal replication in dividing cells. An additional element, the Minichromosome Maintenance Element (MME) ensures the long-term episomal persistence of the genome in the presence of viral E1 and the E2 proteins in the dividing cells. In the BPV-1 genome, total of 17 E2 protein binding sites with different affinities to E2 can be identified: 12 of these are locating in the noncoding upstream regulatory region (URR). We have shown that the minichromosome maintenance element (MME) activity can be provided by the subset of the E2 binding sites. The function of multimeric E2 protein binding sites in the stable maintenance of the BPV-1 genomes is to provide the anchoring function for the E2 protein, which therefore tethers MME containing plasmids to mitotic chromosomes. This linkage between the BPV-1 genome and host chromatin ensures also that the viral genome is targeted to the nucleus when the nuclear membrane is reassembled during mitosis. In the case of EBV, the stable maintenance of replicated genomes is achieved due to the EBNA 1 protein and FR-element, which is comprised of multimeric EBNA1 protein binding sites.

We have shown that the BPV 1 E2 protein dependent MME (Abroi et al. 2004) and EBV EBNA1 dependent FR (Männik, Janikson and Ustav, unpublished) segregation/partitioning activities function independently from replication of the plasmids.

Transfection or infection of permissive cells with polyomavirus genome or replicator results in amplificational replication leading to cell death due to the over-replication. The mechanism of the BPV-1 origin based episomal replication is more complex and controlled. On one hand the first amplificational replication step, resembling in many aspects polyomavirus lytic over-replication is crucial for establishment of the stable episomal replication of the papillomavirus DNA. Such replication leads to increase of expression level of the viral proteins and copy-number of the viral genome. Increase of the E1 protein concentration, however, over certain limit induces the "onion-skin" type replication of the BPV-1 origin and generation of the replication intermediates having tendency for high frequency of DNA rearrangements and integration of the fragments of the viral DNA into chromosomal DNA. To maintain the stability and intactness of the viral genome, virus has to apply certain mechanism to assure proper balance between initiation and elongation of replication fork as well as segregation/partitioning of the viral plasmids during cell division Therapeutic protein production in small and large scale is important field of development in pharmaceutical industry, because proteins produced in animal cells have proper processing, post-translational modification and therefore have adequate activity for treatment of the physiological condition. In general, for research purposes, the transient expression systems are used. The expression plasmids equipped with strong promoter driving expression of gene of interest is transfected into the appropriate cells using either chemical transfection to (like Lipofectamine 2000) or physical transfection, like electroporation. Transfection could be carried out in small scale, resulting in small amount of produced protein or transfected in large scale (up to 100 liters of cell suspension) allowing harvesting expressed protein in large quantity. Problem with large scale transfections is high cost for expensive transfection agent, large quantity of the expression plasmid, and high cost for maintaining large quantity of the cell culture. In these cases the transient transfection has been optimized for 293 HEK cells. However, therapeutic proteins for human use are mostly produced in Chinese Hamster Ovary (CHO cells), which have been proved to be safe and effective for production of therapeutic proteins. This is achieved by generating CHO stable super-producer cell lines isolated as result of screening and several subclonings. These steps are time and money consuming and therefore impractical for research applications. Use of CHO cells has turned out to be difficult in transient production assays due to the poor transfection and production capability.

In order to overcome the shortage of CHO cells in production of therapeutic proteins in transient transfections, use of episomal expression vectors is one of the possibilities enhancing expression plasmid copy-number and maintaining it in the cells for extended time for enlarging fraction of cell producing therapeutic protein as well as improving yield of the protein production.

The stable episomal maintenance systems described earlier (U.S. Pat. No. 6,479,279) were provided with homologous replication origins. Characteristic for these systems is for example a high mutation frequency, especially recombination. Furthermore, the system does not maintain stably replicating episomes in cells because part of the cells lose their plasmid in every generations. This deficiency of the system can be compensated by application of continuous antibiotic selection pressure on cells in order to eliminate the plasmid-negative cells from the culture. This fact creates serious limits for the system to be used for example in protein production.

U.S. patent application Ser. No. 10/938,864 (Kunaparaju) provides a heterologous system, which is capable of stable episomal replication lasting a couple of weeks. Kunaparaju uses two functional replicons in the expression plasmid—one dependent on wtPyV replication origin and Large T-antigen and second, oriP and EBNA1. Limitations in this system is use of wild type polyomavirus origin equipped with enhancer which we have shown to initiate over-replication and generating too high copy-number of the plasmid eventually leading to death of the cells. Cell adaptation to too high copy-number will include rearrangement of the plasmid leading to genetic instability and therefore incompatibility with the requirements for therapeutic protein production. Second limitation is use of complete oriP, which is comprised of two elements— Dyad Symmetry Element (DUE), which is eukaryotic origin of replication functioning as a result of cellular replication factors and Family of Repeats (FR), which is serving as cis-sequence for EBNA1 dependent segregation/partitioning of the plasmid. It means that Kunaparaju et al. invention uses two viral eukaryotic origins of replication, which may fire independently of each other and generate a conflict between initiation of DNA replication. The present disclosure provides improvements over the problems encountering prior systems.

SUMMARY OF THE INVENTION

The present disclosure provides an extended episomal maintenance system with heterologous replication origin, stable episomal replication lasting longer than with any prior art method, cell viability staying high for longer than with any other known method.

The present disclosure provides a system where plasmids containing core polyoma virus origin (not containing enhancer function) partition into daughter cells. The system according to this disclosure provides a hybrid system where a unique configuration of polyoma virus origin (core polyomavirus origin not containing enhancer function) is stable for initiation of replication by the large T antigen and is segregated due to the action of helper protein EBNA1 from Epstein-Barr virus acting on multimeric EBNA1 binding sites fused to the PyV enhancerless replication origin during the mitosis.

An advantage of the present system is that high copy-number extrachromsomal state of chimeric origins is maintained without rearrangement. The present invention further provides a possibility to combine vectors with polyoma virus origin and papilloma origin into a single cell, thereby enabling expression of more than one different recombinant proteins or RNAs in one cell. A further advantage of the current system is that it provides stable episomal maintenance in the cell that lasts up to several months as opposed to all previous systems, which provide maintenance of maximally a few weeks.

In U.S. patent application Ser. No. 11/351,809 we showed how the stable maintenance can be provided with a hybrid plasmid containing the PyV core origin, and MME element containing at least 5 E2-binding sites. We also showed that the extended stable maintenance can be provided also by replacing the enhancer with EBNA1-binding sites of EBV. Here we describe in more details the expression system comprising PyV core origin, and FR element of EBV in various applications.

The problem that we aim to solve is that production of gene products in animal cell systems is costly and time consuming. This problem has been solved in the present disclosure by providing data, which show that transient expression of gene products in the engineered cells is possible due to the high efficiency of delivery of the expression plasmids. Since the genes of interest are replicated and maintained outside the chromatin in the nucleus, the replicating expression plasmids do not have positional effect of the host cell DNA on expression of the gene of interest like it has been shown for the stable cell lines carrying integrated expression cassettes. The extrachromosomal plasmids go to the progeny in cell division and segregation, maintain transcriptional activity and with the method of the current disclosure, the expression of the gene products can be continued for months. This enables generation of the production of the proteins of interest using cell population with homologous copy-number of extrachromosomal expression plasmids without additional subcloning. Use of the expression system according this disclosures allows production of therapeutic proteins in research setting using the transient mode of expression. Additional benefit of the system disclosed here is that we can generate cell banks and maintain these in liquid nitrogen, which allows repeated production of the protein of interest. Further, we can use the same cell banks for large scale production of the therapeutic proteins in cost and time effective way.

Development of stable expression in cell lines takes usually several months or even years. The system that we describe here is enabling generation of production cell culture in transient format as well as stable long-term culture and is much faster and therefore useful and novel. Further more, transient systems so far known do not have capability of maintaining expression plasmid in the cell and therefore they have very limited half-life; i.e. maximally up to 7 days. In addition, those systems may need construction of recombinant viruses, which makes the systems expensive and very time consuming. Our system provides a marked improvement to the existing art; the system according to this disclosure provides a transient expression system that maintains the expression levels for several weeks and even up to several months.

The present disclosure provides a possibility to develop stable cell lines when the vector according to this disclosure contains a selection marker and the cells are cultivated on a medium containing the selective agent. The present disclosure also provides a possibility to express gene products in a cell line for shorter time when the vector does not contain a selection marker. However, even without using selection pressure the current system provides stable maintenance that lasts longer than with any other comparable system previously known.

The present disclosure further enables development of a multi-replicon expression system, where more than one gene products are expressed from different replicons and the replicons are locating in same cell. Such a mechanism is useful for example to express different subunits of antibodies or enzyme subunits in one cell or to study interactions of macromolecules expressed in the cell.

An object of the present disclosure is to provide a mechanism to extended episomal maintenance of polyoma virus core origin.

Another object of the present disclosure is to provide a mechanism to extended episomal maintenance of polyoma virus core origin plasmids without selective pressure for use in transient production of the proteins.

Yet another object of the present disclosure is to provide constructs in conjunction with the segregations/partitioning elements from EBV.

A further object of the present disclosure is to provide cell lines capable of supporting the replication and episomal maintenance of hybrid plasmids.

A still further object of the present disclosure is to provide a transient system for extended (up to 14 days without selection) expression of gene products in eukaryotic cells allowing expansion of the volume of the production culture and therefore output of the protein of interest.

An even further object of the present disclosure is to provide cell lines harboring more than one different vector and thereby providing expression of more than one different genes of interest.

Yet a further object of the present disclosure is to provide a transient system for long lasting production therapeutic, prophylactic or endotoxine free gene products for diagnostic and other applications in eukaryotic cells.

Another object of the present disclosure is to provide a transient system for long lasting production of RNA or proteins in eukaryotic cells. The cells can be cultivated and gene products can be expressed in small and large scale; from laboratory flasks and Petri dishes up to big fermentors.

Yet another object of the present disclosure is to provide a system for extended production of proteins, antibodies, enzymes and virus-like particles.

In patent application Ser. No. 11/351,809, we showed that the BPV-1 E2 protein dependent MME comprising E2 multimeric binding sites can provide extended maintenance replication function to the mouse polyomavirus (PyV) core origin plasmids in the presence of BPV-1 E2 protein and PyV large T-antigen (LT), but fail to do so for the complete PyV origin. In mouse fibroblast cell-lines expressing PyV LT and BPV-1 E2 (COP5/E2), the plasmids carrying PyV core origin linked to at least five multimeric E2 protein binding sites show the capacity for long term episomal replication, which can be monitored for more than 5 months (under selective conditions). Overall structural integrity as well as the intactness of domains of BPV-1 E2 are required for efficient episomal maintenance. Our data showed clearly that the large T antigen dependent replication function of the polyomavirus and extended maintenance functions of the BPV-1 are compatible in certain configurations. Further quantitative analysis of the loss of the episomal plasmids carrying hybrid origin showed that MME dependent plasmids are lost with the frequency of 6% per generation.

Similar hybrid origins comprising the EBV FR-element and polyomavirus replication origin were constructed and studied in the cell lines expressing EBNA1 and polyomavirus large T antigen (LT). Our data suggest convincingly that segregation/partitioning functions of the BPV-1 and EBV can effectively be used for extended episomal maintenance of the polyomavirus core origin.

BRIEF DESCRIPTION OF THE FIGURES

FIG. 1. Schematic representation of mouse polyoma virus core origin of replication and FR (Family of repeats) element. Here, FR element (SEQ ID NO:1) contains 21 possible EBNA-1 binding sequences (SEQ ID NOs: 3, 4, 5, 6, 28-43). DNA fragments containing EBNA-1 binding sequences are aligned and underlined.

Line 1. Protein marker (#SM0671, lot: 00052778, Fermentas); Line 2. CHOEBNALT85 [pQMCF-1-DNaseI] culture supernatant before production phase, Line 3. CHOEBNALT85 [pQMCF-1-DNaseI] culture supernatant, 4$^{th}$ day of production Line 4. CHOEBNALT85 [pQMCF-1-DNaseI] culture supernatant, last day of production; Line 5. CHOEBNALT85 [pQMCF-1-DNaseI] culture supernatant, cells were taken from production cell bank (last day of production).

Figure 10:
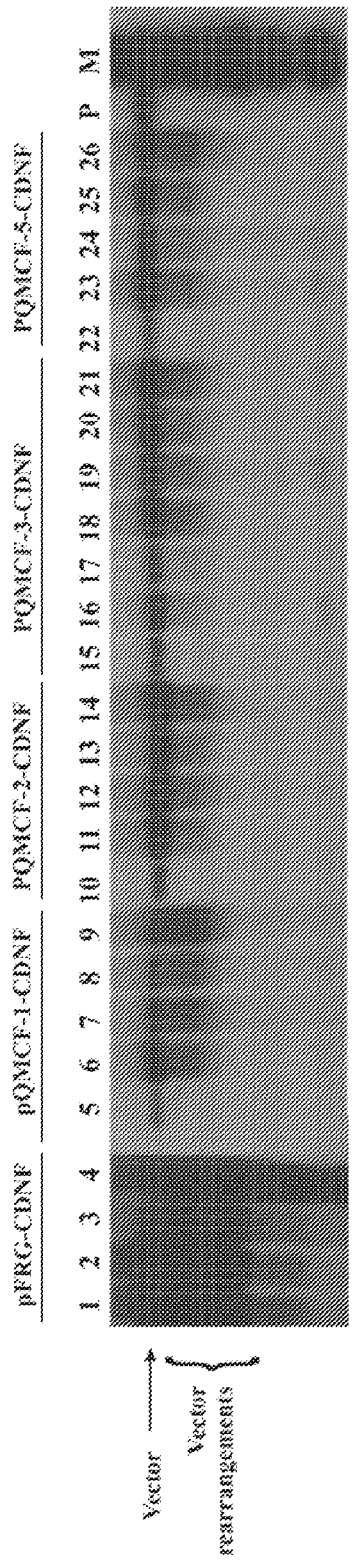

FIG. 10. Southern-Blot analysis of bovine DNaseI production plasmids. Lines 1-4 Old version pQMCF vector during production phase; Lines 5-9 pQMCF-1-DNaseI (CMV promoter containing vector), Lines 10-14 pQMCF-2-DNaseI (hEF1-HTLV promoter containing vector), Lines 15-21 pQMCF-3-DNaseI (heIF4a promoter-containing vector), Lines 22-26 pQMCF-5-DNaseI (RSV-LTR containing vector)., Lines 27-31 pQMCF-6-DNaseI (hEF 1α containing vector). Lines 5, 10, 15 22 and 27 exhibit time point 48 h after transfection. All other lines represent samples taken before production phase or during production phase. Line 32—control; Line 33 DNA size marker.

Figure 11:
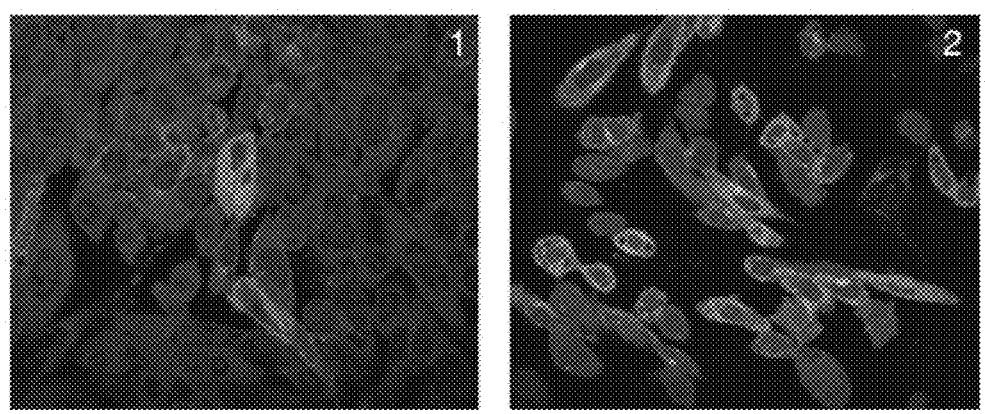

FIG. 11. Analysis of ETAR-translocation assay. Adherent CHOEBNALT cells were stably transfected with ETAR-EGFP (SEQ ID NO:24) bearing QMCF plasmid. After 4 weeks of G418 selection cells were treated with 300 nM of endothelin-1. Non-endotheline-1 treated cells; 2: ETAR-EGFP internalization in after endothelin-1 treatment. Green—GFP signals from ETAR-EGFP fusion protein; red—cytosol and nucleoli (Nikon Eclipse TE-2000-U; 60×).

Figure 12:
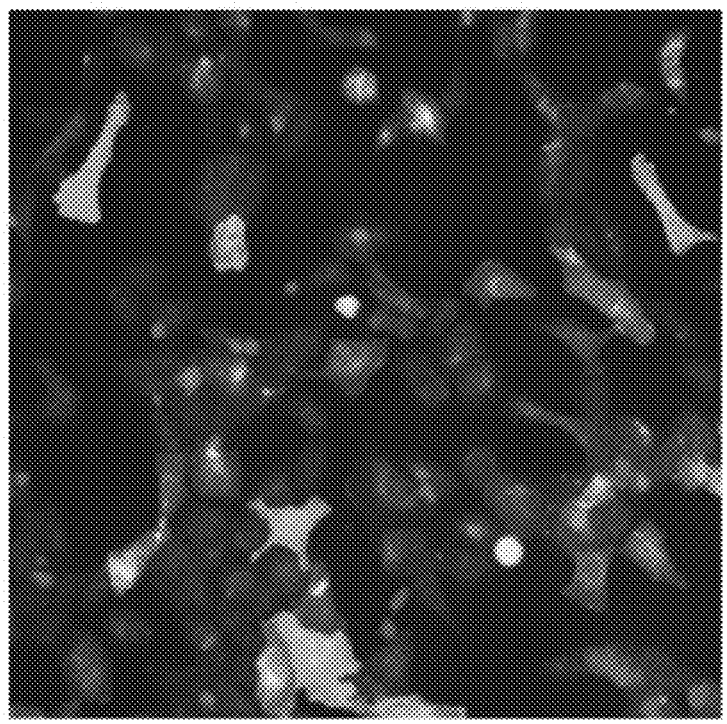

FIG. 12. Detection of ETAR-5E11 tag fusion protein in adherent U2OSEBNALTD3 cells. Green—ETAR-5E11tag fusion protein; red—cytosol and nucleoli (ArrayScan VTi 40×).

Figure 13:
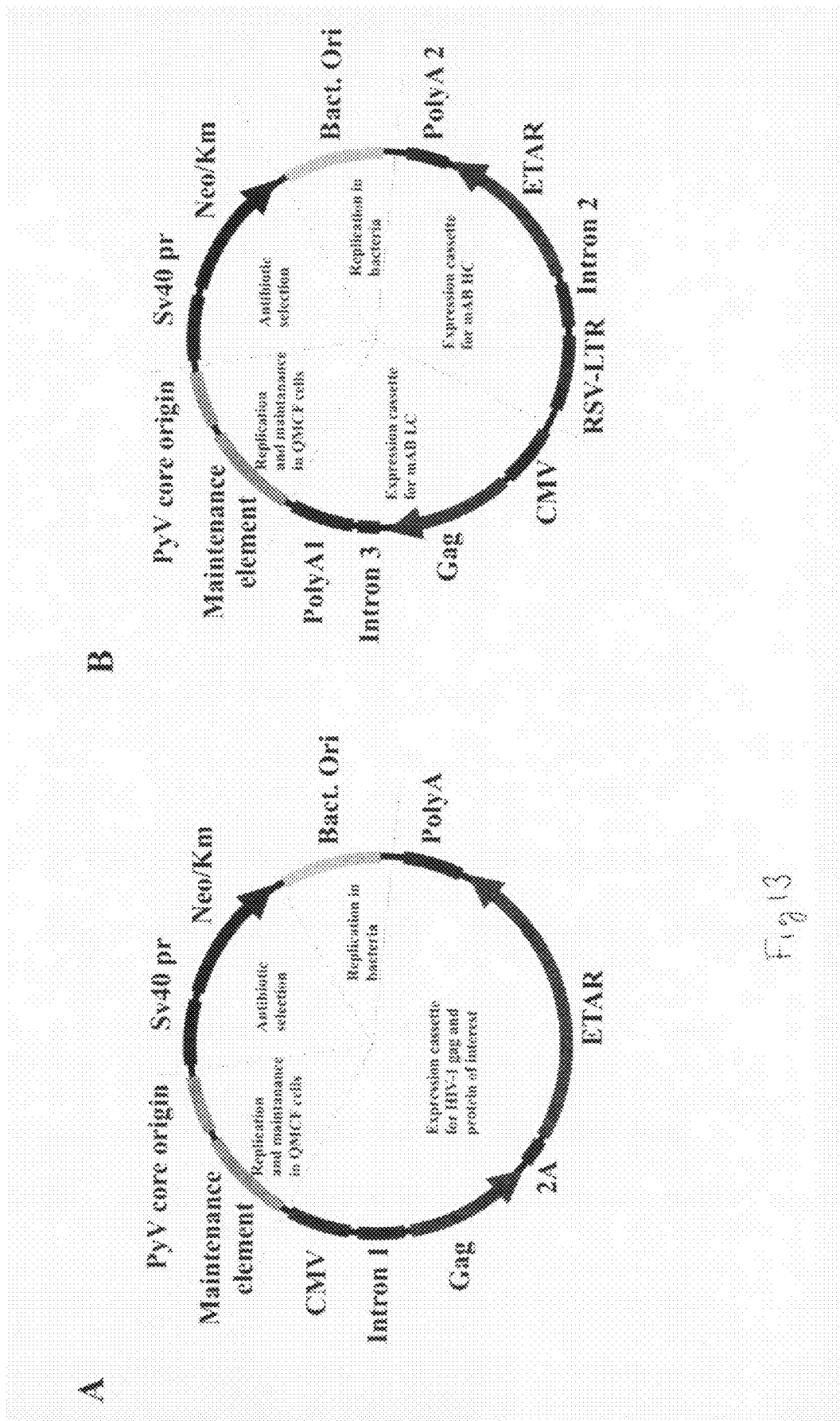

FIG. 13. Schematic representation of single-expression (A) and double-expression (B) cassette containing vector for expression of Virus Like Particles (VLP-s) 1. Replication and maintenance in QMCF cells: Maintenance element—(Epstein-Barr Virus Family of Repeats (FR)); PyV core origin—murine polyomavirus origin of replication without enhancer element; 2. Antibiotic selection: SV40 pr—SV 40 promoter controlling expression of Neo resistance gene; Neo/Km—Neomycin/Kanamycin resistance marker for selection of plasmid containing cells in bacteria and eukaryotic cells; 3. Replication in bacteria: pMMB origin of replication; 4. Expression cassette: Promoters (CMV for gag protein expression, RSV-LTR or hEF1α-HTLV for protein of interest expression); Intron—hEF1α intron (Intron 1 and intron 2) in 5' position from gene of interest, bgh intron (SEQ ID NO: 26) (Intron 3) in 3' position of gag protein expression gene; Gag—HIV-1 or MLV gag protein; 2A—Foot-and-mouth disease virus (FMDV) 2A peptide (SEQ ID NO:27); ETAR—G-protein coupled receptor (example protein); polyA—SV40 polyadenylation sequence (PolyA and PolyA2) regulating expression of Neo/Km and gene of interest simultaneously, polyA1—bgh polyA regulating expression of gag protein.

Figure 14:
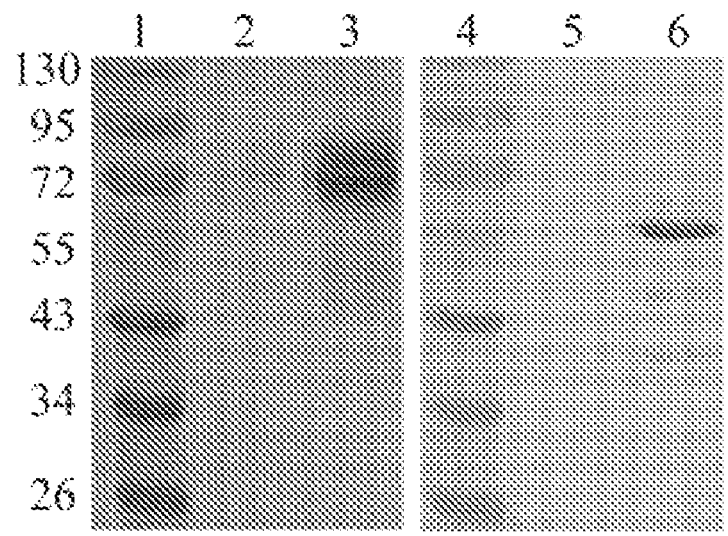

FIG. 14. Production of ETAR-pseudotyped HIV-gag based VLP-s using 293EBNALT75 cell line. All samples were ultracentrifuged for VLP purification. Lines 1 and 2 ETAR is detected by BPV E2 tag antibody, lines 5-6 detected using HIV-gag specific antibody. Line 1. Protein marker (#SM0671, lot: 00052778, Fermentas). Line 2. Supernatant of 293EBNALT75 expressing ETAR. Line 3. Supernatant of 293EBNALT75 expressing ETAR and HIV-gag. Line 4. Protein marker (#SM0671, lot: 00052778, Fermentas). Line 5. Supernatant of 293EBNALT75 expressing ETAR. Line 6. Supernatant of 293EBNALT75 expressing HIV-gag.

Figure 15:
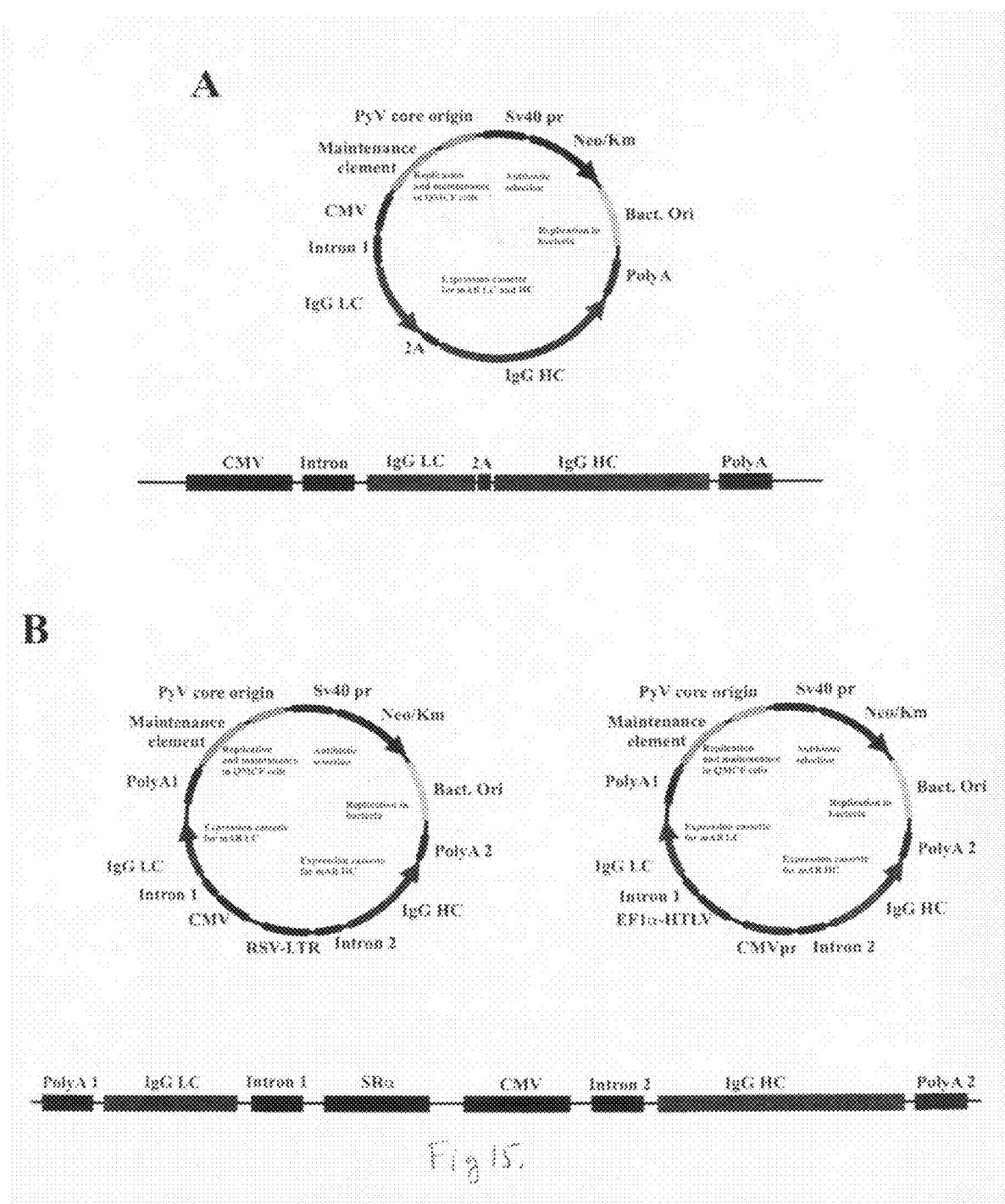

FIG. 15. Schematic representation of single- and double-expression cassette containing vector for expression of monoclonal antibodies 1. Replication and maintenance in QMCF cells: Maintenance element—(Epstein-Barr Virus Family of Repeats (FR)); PyV core origin—murine polyomavirus origin of replication without enhancer element; 2. Antibiotic selection: SV40 pr—SV 40 promoter controlling expression of Neo resistance gene; Neo/Km—Neomycin/Kanamycin resistance marker for selection of plasmid containing cells in bacteria and eukaryotic cells; 3. Replication in bacteria: pMMB origin of replication; 4. Expression cassette: Promoters (CMV, RSV-LTR or hEF1α-HTLV for expression of antibody heavy and light chain is used); Intron-hEF1α intron and CMV intron in 5' position from gene of interest) 2A—Foot-and-mouth disease virus (FMDV) 2A peptide; IgG HC and IgG LC—coding regions for expression of antibody heavy- and light chains; polyA—SV40 polyadenylation sequence regulating expression of Neo/Km and gene of interest simultaneously or bgh polyA is used for regulation of expression of antibody light- or heavy chain.

Figure 16:
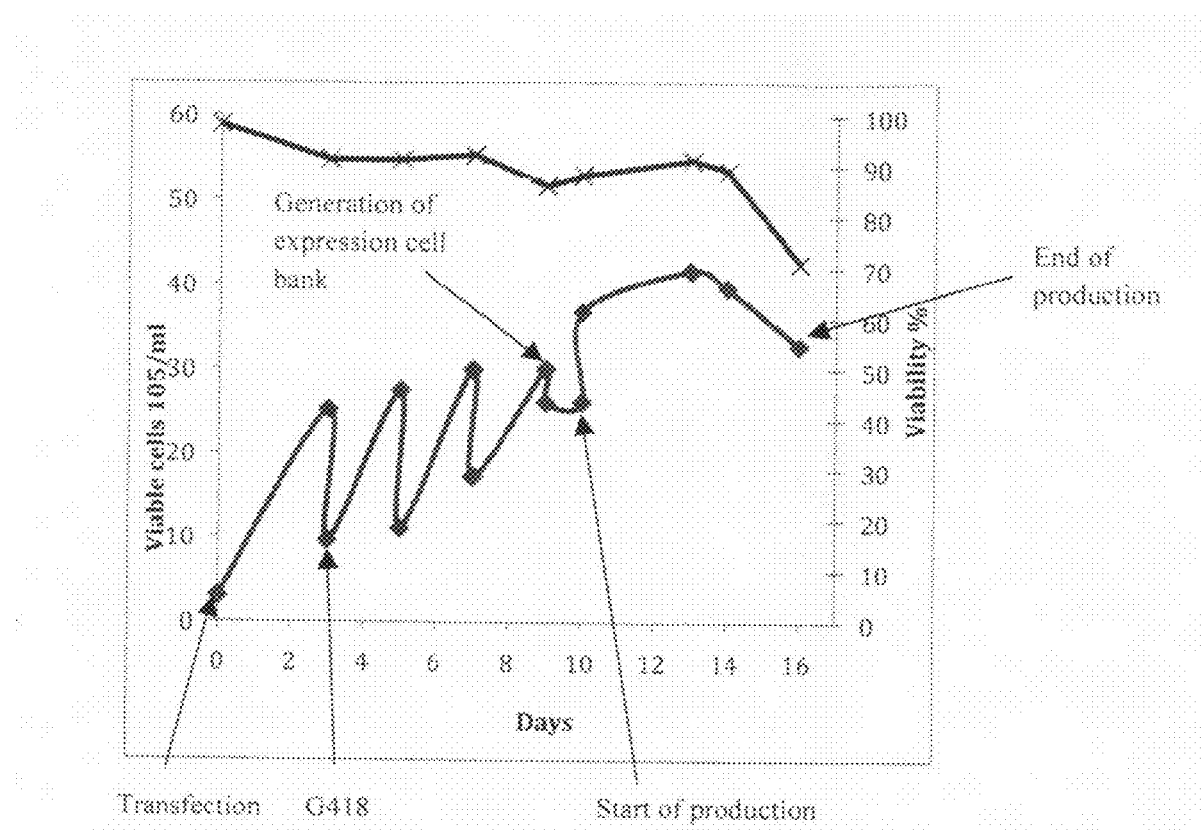

FIG. 16. Growth of the monoclonal antibody-expressing CHOEBNALT85 cell culture. 48 h after transfection G418 (700 μg/ml) was added. 9 days after transfection expression cell bank was generated. From day 10 to 16 the production phase was performed. Temperature was reduced to 30° C., additional nutrients were added to the medium. The viability of the cell culture was more than 85% during antibiotic selection and production. At day 16 when viability of the culture starts to decline, supernatant of the culture was clarified by centrifugation and filtered through 0.45 μm filter.

Figure 17:
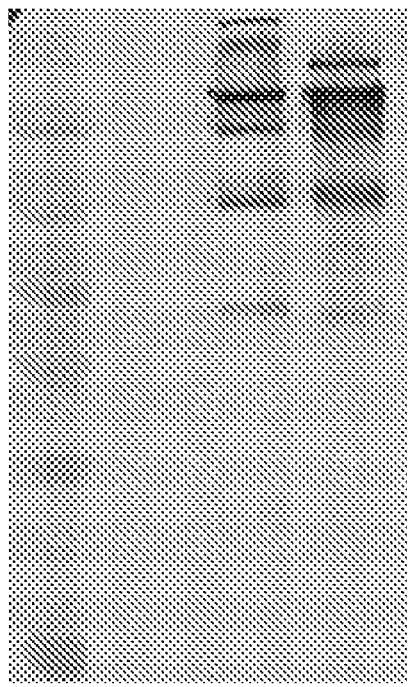

FIG. 17. Western-Blot analysis of partially humanized (chimeric) tyrosinase A antibody expressed by CHOEBNALT85 cells. Line 1. Protein marker (#SM0671, lot: 00052778, Fermentas); Line 2. Non-transfected CHOEBNALT85 cell growth medium; Line 3. Supernatant of CHOEBNALT85 cell line expressing recombinant monoclonal partially humanized (chimeric) tyrosinase A antibody; Line 4. Positive control (ImmunoPure Human IgG Whole Molecule 31154, Pierce).

Figure 18:
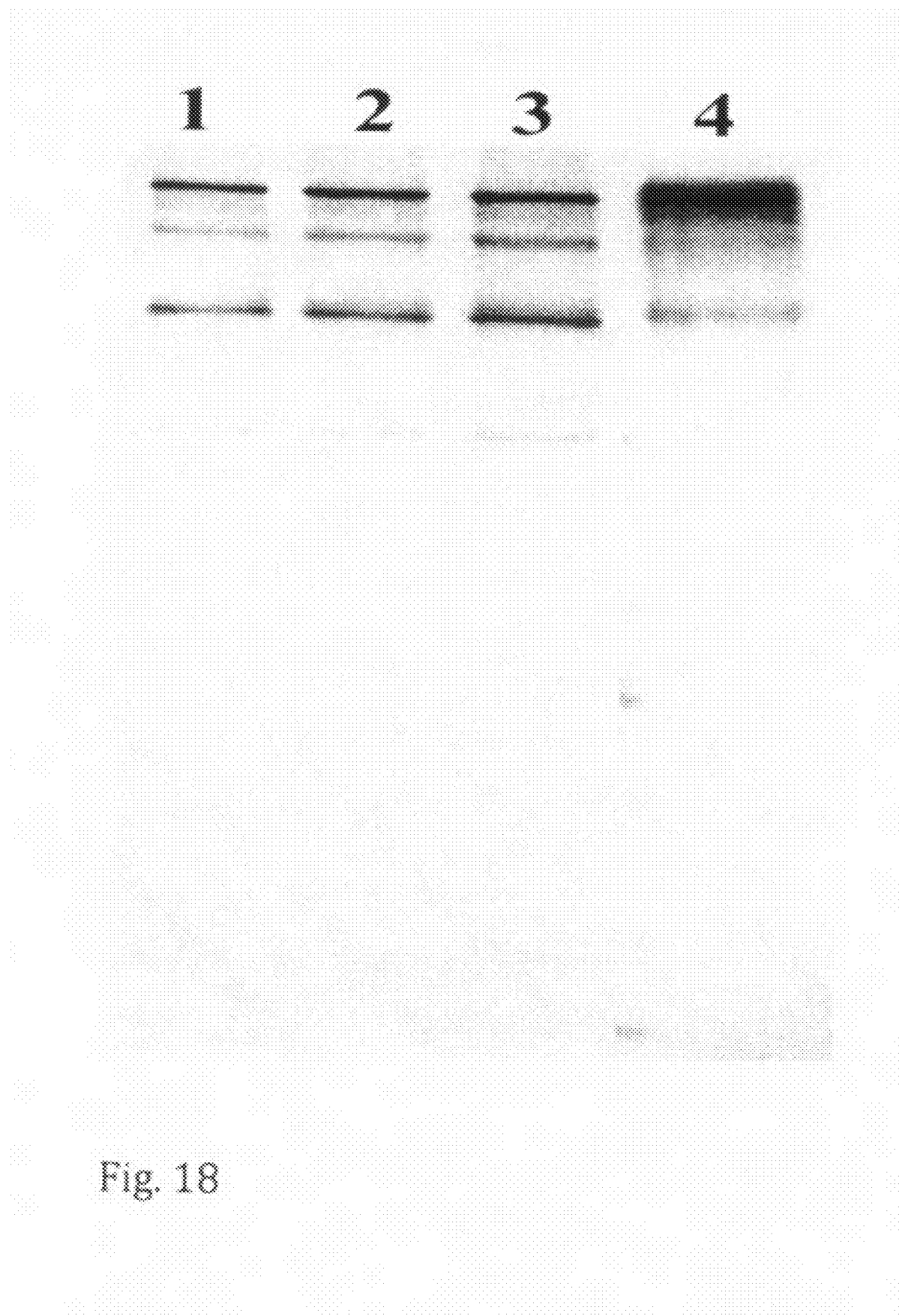

FIG. 18. Western-Blot analysis of partially humanized (chimeric) tyrosinase A antibody expressed by CHOEBN-ALT85 cells. Line 1. Supernatant of CHOEBNALT85 cell line expressing recombinant monoclonal partially humanized (chimeric) tyrosinase A antibody, time point before production phase; Lines 2 and 3. Supernatant of CHOEBNALT85 cell line expressing recombinant monoclonal partially humanized (chimeric) tyrosinase A antibody, time point during production phase; Line 4. Supernatant of CHOEBNALT85 cell line expressing recombinant monoclonal partially humanized (chimeric) tyrosinase A antibody, time point at the end of production phase.

Figure 19:
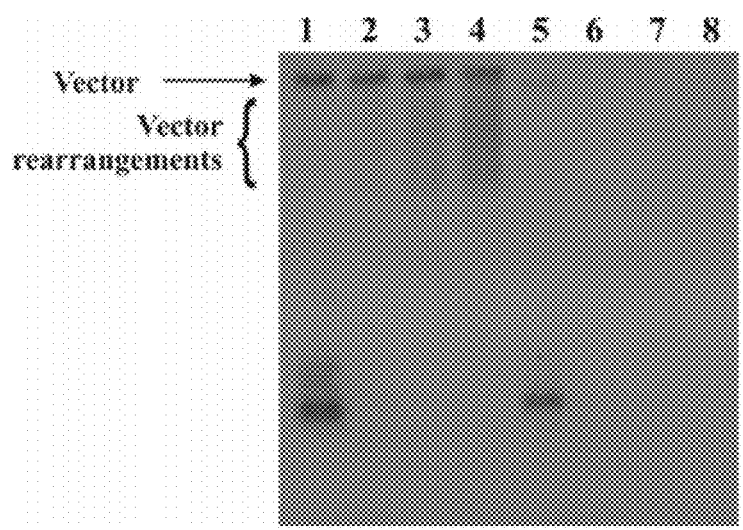

FIG. 19. Southern-Blot analysis of pFRG-EFFP and pFRG-EGFP-FR (without FR element). Lines 1-4 pFRG-EGFP; Lines 5-8 pFRG-EGFP-FR (without FR element). Time points of analysis in figure: Line 1 and 5. 48 hours after transfection; Lines 2 and 6 14 days after transfection; Lines 3 and 7 21 days after transfection; Lines 4 and 8 22 days after transfection.

Figure 20:
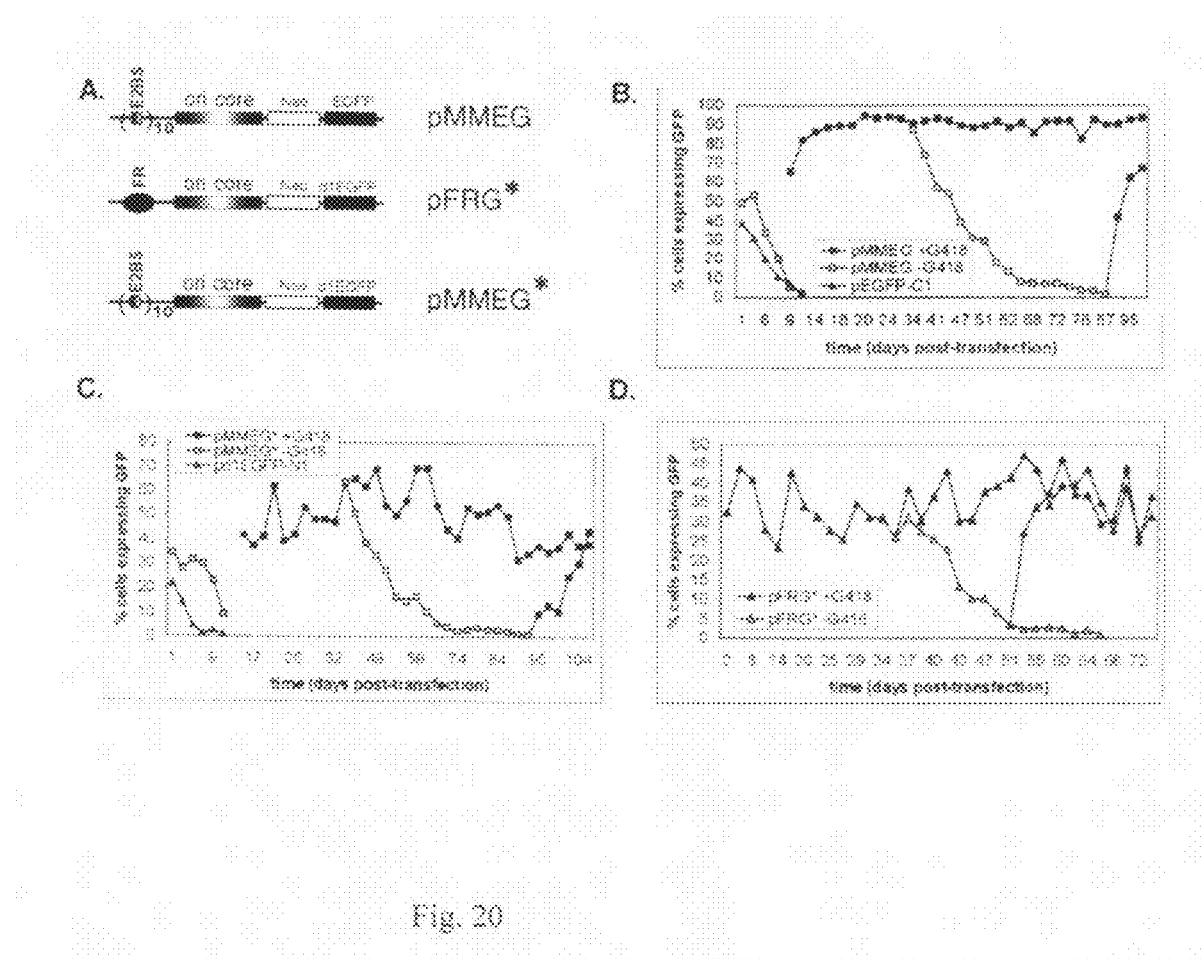

FIG. 20. Schematic representation of PyV hybrid origin constructs used in flow cytometry analysis (A). Time course of long-term EGFP (B) or short-term d1EGFP (C,D) expression in the presence or absence of G418 selection for various cell lines. COP5E2/PuroMMEG (B); COP5E2/PuroMMEG* (C); COP5EBNA1/PuroFRG* cell line (D).

FIG. 21A-F is a schematic illustration of the novel vectors according to this disclosure. The vectors are called pQMCF1-pQMCF6 A. pQMCF1 contains CMV promoter-driven expression cassette. B. pQMCF2 contains EF1α-HTLV promoter-driven expression cassette. C. pQMCF-3 contains heIF4a promoter-driven expression cassette D. pQMCF-4 contains β-actine promoter-driven expression cassette. E. pQMCF-5 contains RSV-LTR promoter-driven expression cassette. F. pQMCF-6 contains heIF1α promoter-driven expression cassette. Single-cutting restriction sites are shown in the maps.

Figure 22A:
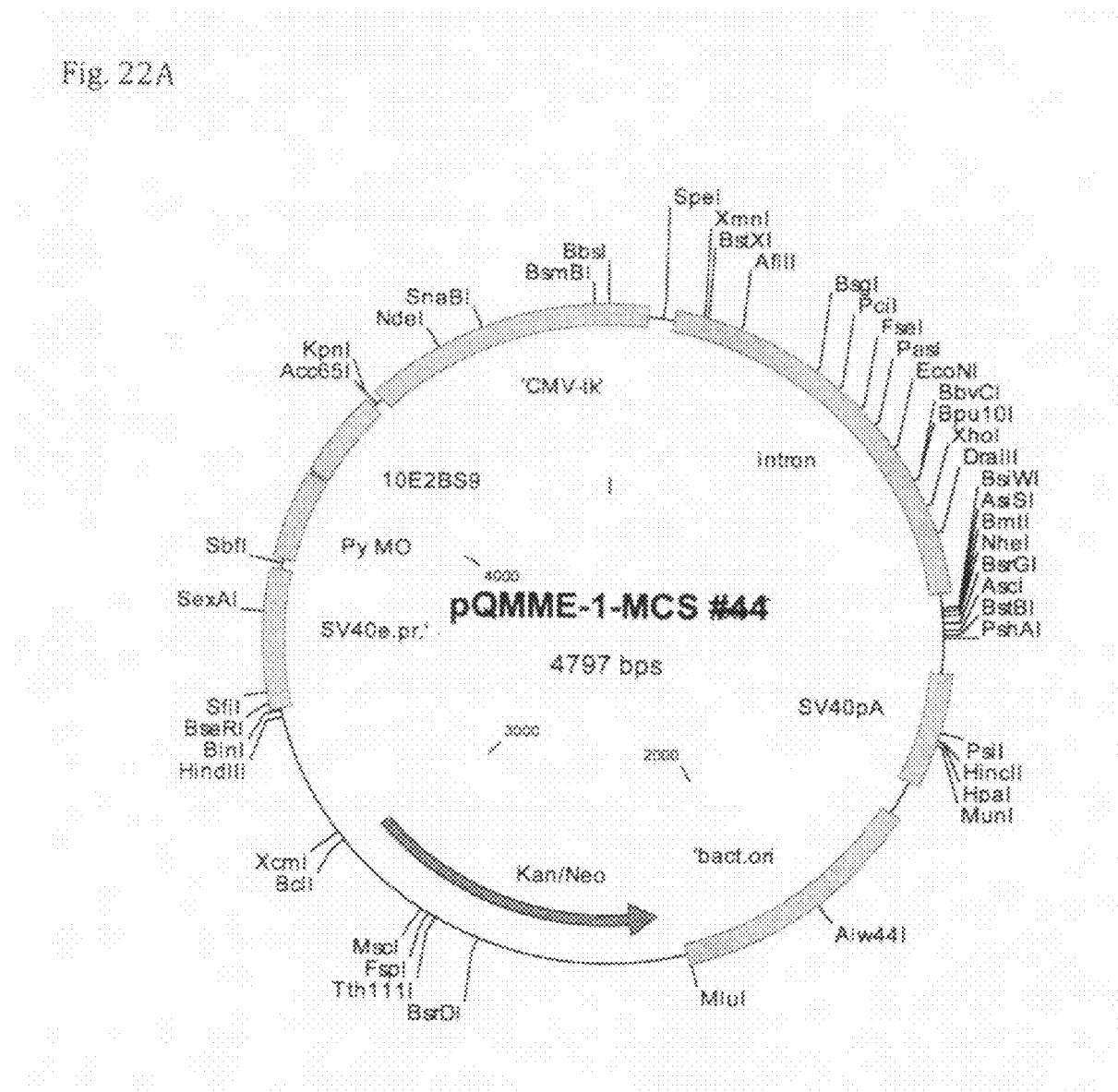
Figure 22B:
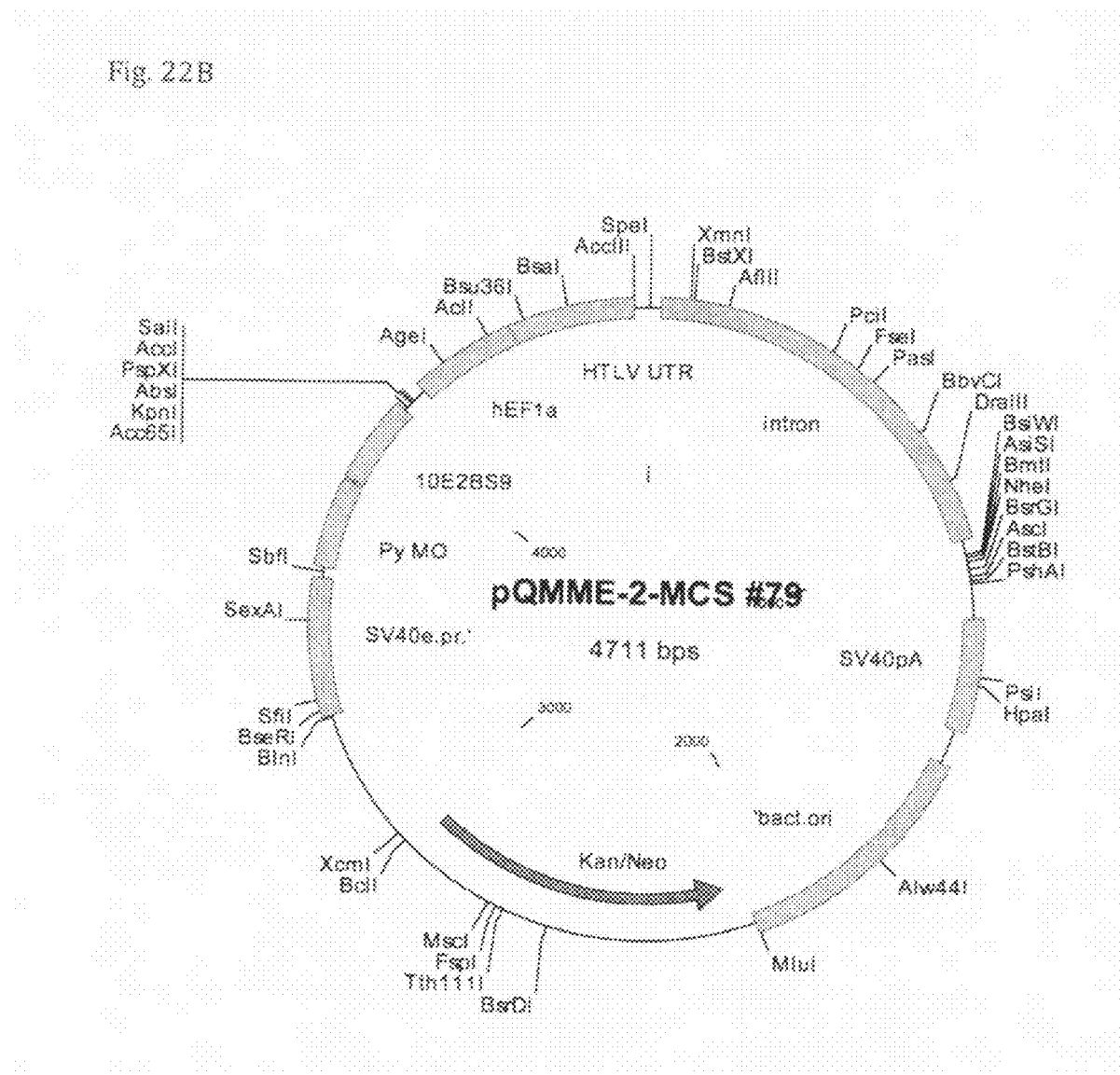
Figure 22:
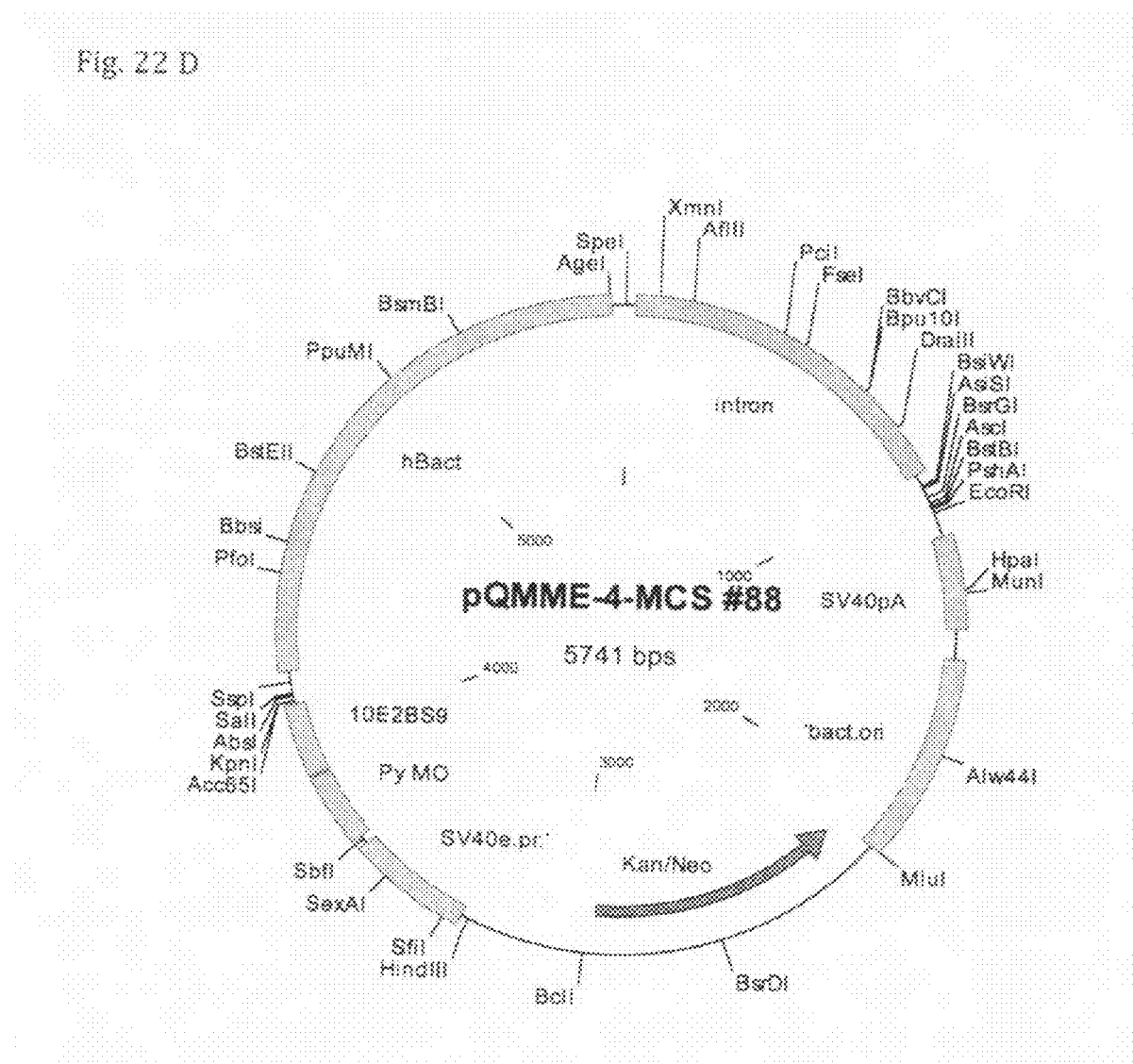
Figure 22:
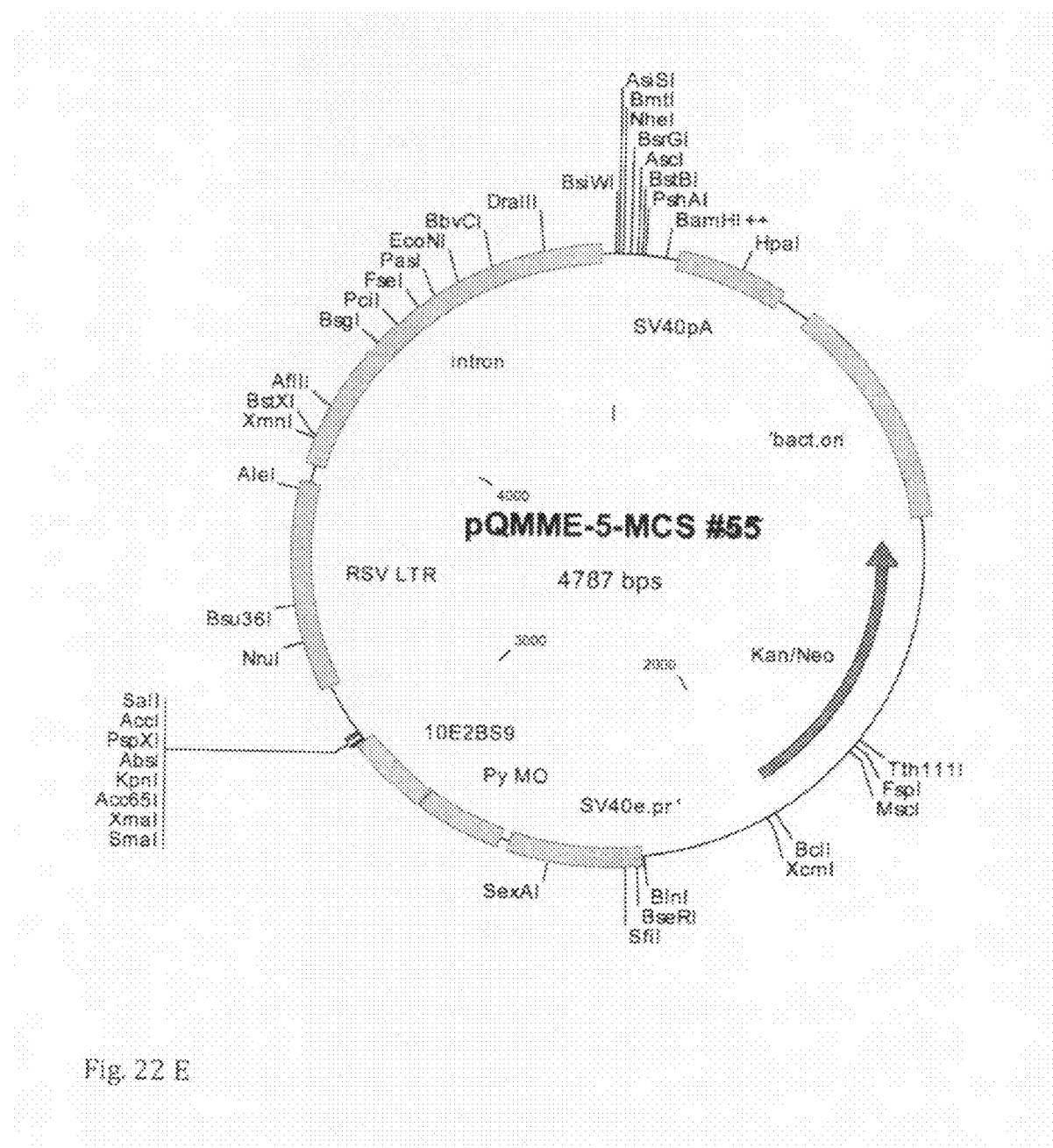

FIG. 22 A-F is a schematic illustration of the novel vectors according to this disclosure. The vectors are called pQMME 1-6. A. pQMME-1 contains CMV promoter-driven expression cassette. B. pQMME-2 contains hEF1α-HTLV promoter-driven expression cassette. C. pQMME-3 contains heIF4a promoter-driven expression cassette. D. pQMME-4 contains human β-actin promoter-driven expression cassette. E. pQMME-5 contains RSV-LTR promoter-driven expression cassette. F. pQMME-6 contains RSV-LTR promoter-driven expression cassette. Single-cutting restriction sites are shown in the maps.

Figure 23A:
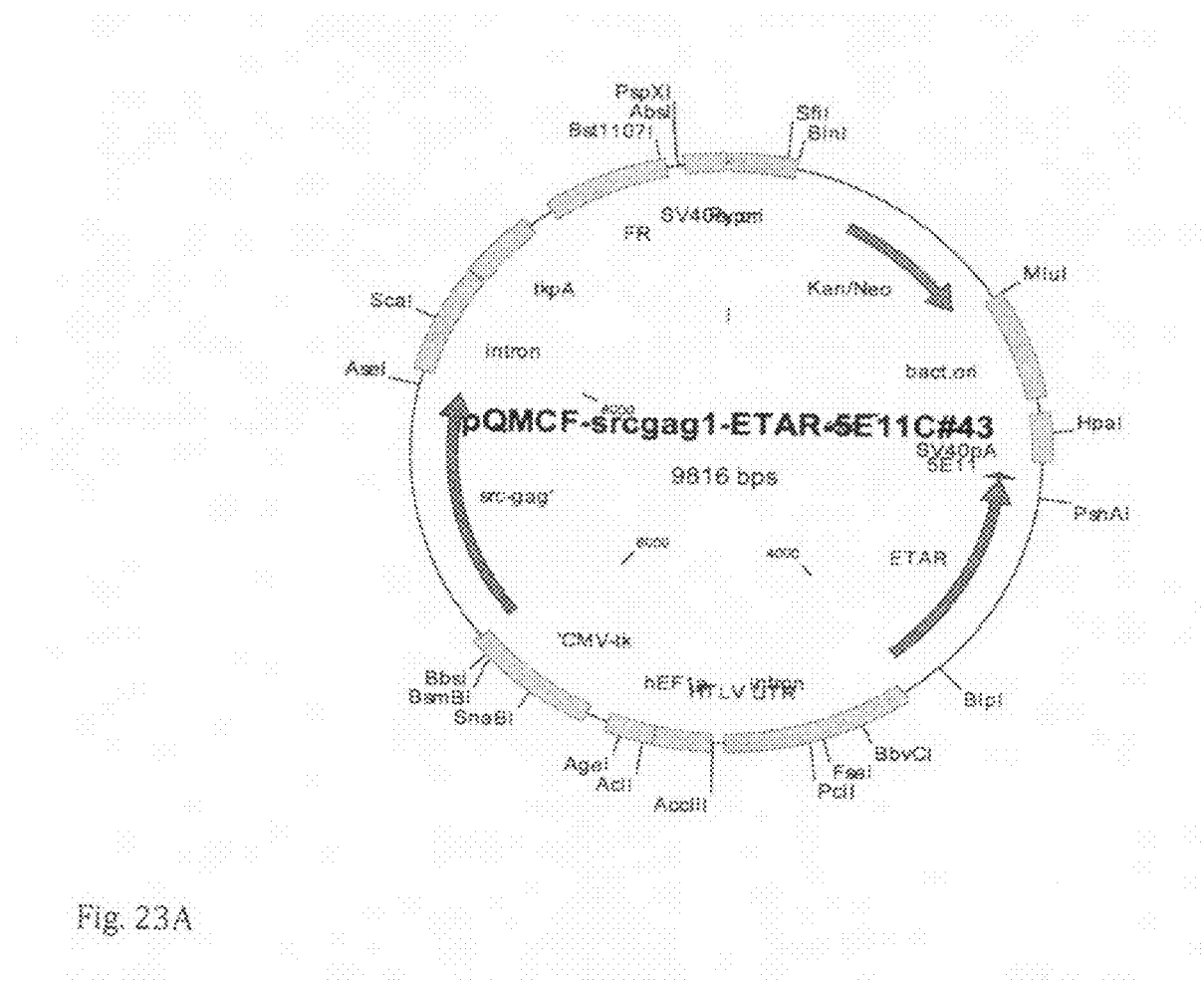
Figure 23B:
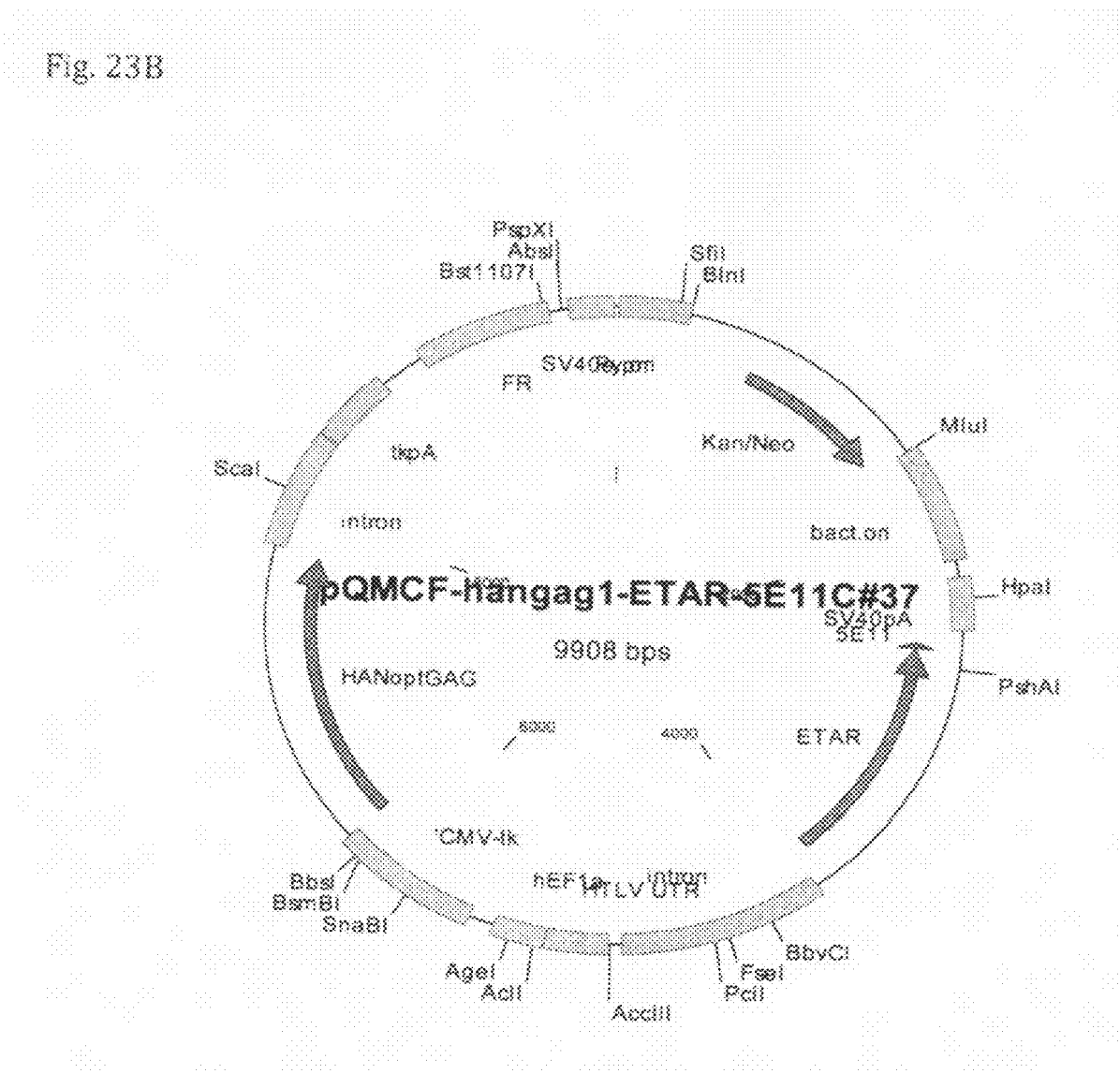

FIG. 23 A-B is a schematic illustration of the novel VLP expression vectors according to this disclosure. A. pQMCF-VLP-srcgag1 vector contains two expression cassettes: CMV promoter-driven expression cassette for srcgag protein (cDNA sequence according to SEQ ID NO:26) and hEF1α-HTLV promoter-driven expression cassette for ETAR expression. B. pQMCF-VLP-hangag1 vector contains two expression cassettes: CMV promoter-driven expression cassette for srcgag protein and hEF1α-HTLV promoter-driven expression cassette for ETAR expression. Single-cutting restriction sites are shown in the maps and the sequence.

Figure 24A:
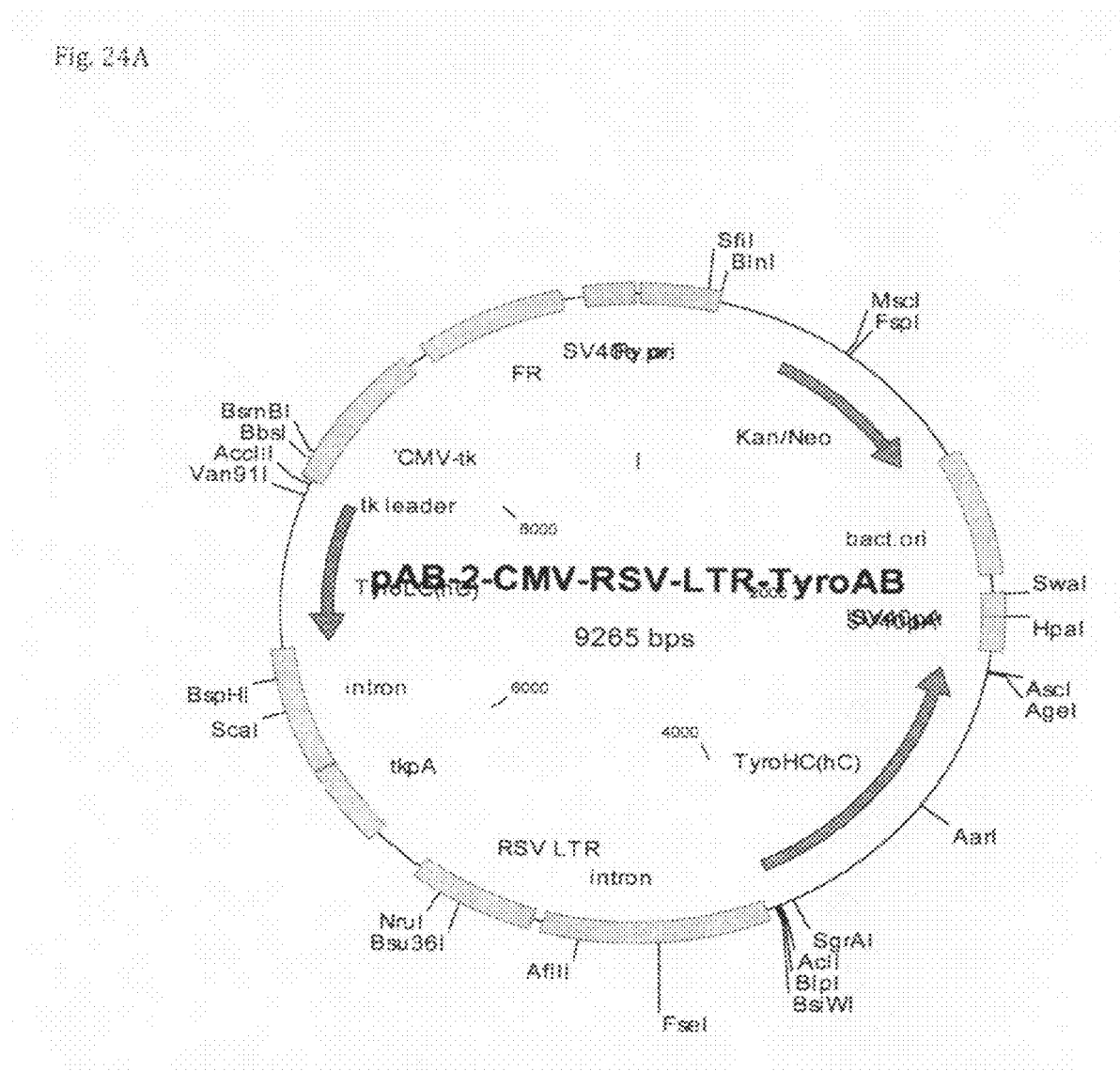

FIG. 24 is a schematic illustration of the novel monoclonal antibodies expression vectors. A. Map of partially humanized (chimeric) tyrosinase A antibody expression vector (two expression cassettes: CMV promoter-driven antibody light chain expression cassette and RSV-LTR promoter-driven expression cassette for antibody heavy chain expression cassette). Single-cutting restriction sites are shown in the map. Expression cassettes of antibody light- and heavy chain are locating in same direction. B. Map of partially humanized (chimeric) tyrosinase A antibody expression vector (two expression cassettes: CMV promoter-driven antibody light chain expression cassette and RSV-LTR promoter-driven expression cassette for antibody heavy chain expression cassette). Single-cutting restriction sites are shown in the map. Expression cassettes of antibody light- and heavy chain are locating in opposite direction.

Figure 25:
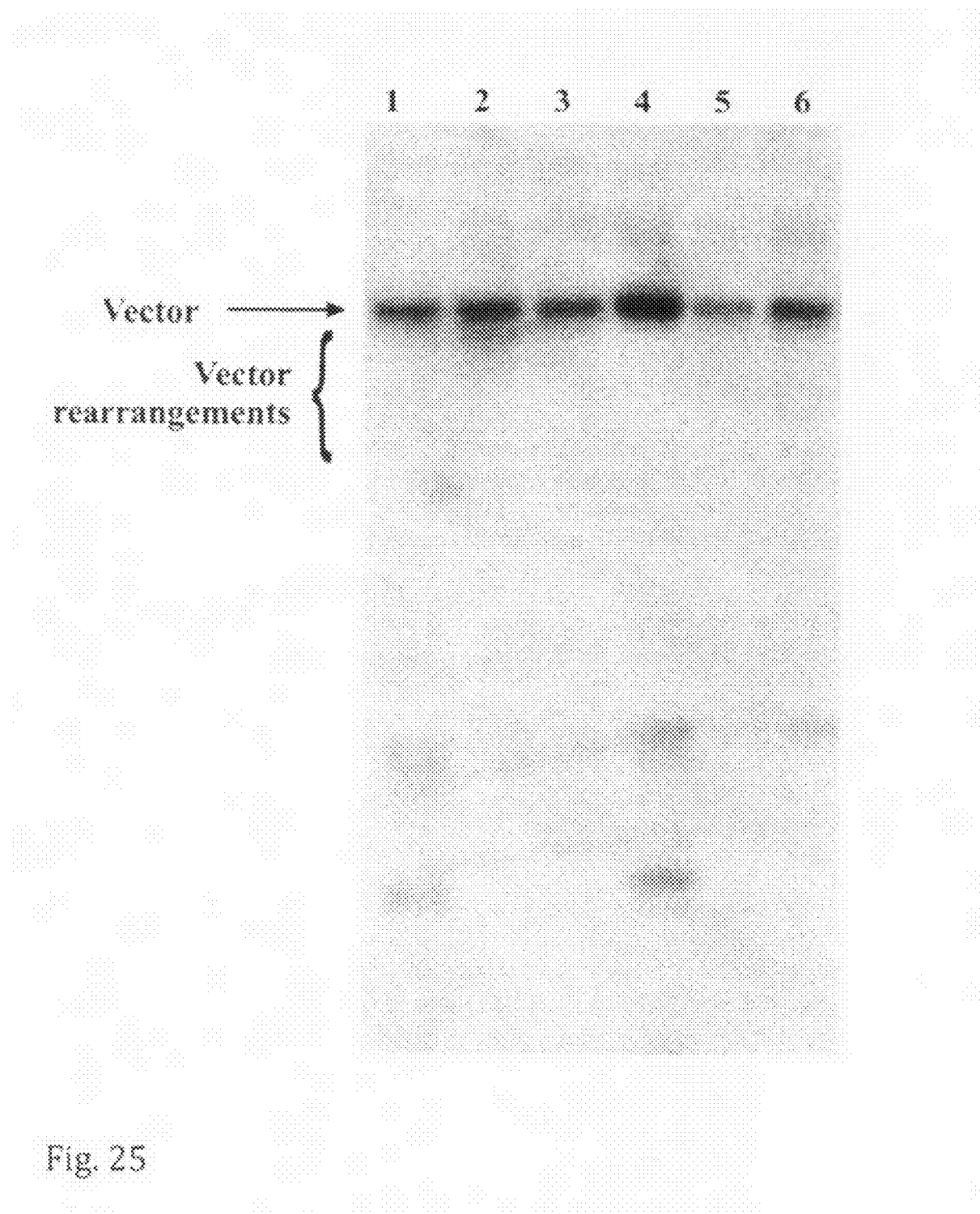

FIG. 25. Southern-Blot analysis of pQMME-1-EGFP and in U2OSEBNALTE2 adherent cell line. Lines 1-3 and 4-6 exhibit results of plasmid stability in two different U2OSEBNALTE2 cell lines. Lines 1 and 4 show results of time points 48 hours after transfection. Lines 2 and 6 show results of time points 32 days after transfection. Lines 3 and 6 show results of time points 52 days after transfection.

DETAILED DESCRIPTION OF THE INVENTION

Definitions

In this disclosure the following terms are used as defined below:

"Papillomavirus" refers to a member of the papilloma family of viruses, including but not limited to bovine papillomavirus (BPV) and human papillomavirus (HPV).

"Polyomavirus" refers to a member of polyoma family of viruses, including but not limited to mouse polyomavirus (PyV).

"Polyomavirus core origin" refers to a minimal cis-sequence within a polyomavirus that is necessary for initiation of DNA synthesis. The PyV core origin is essentially according to SEQ ID NO: 2. The core origin of PyV is located at nucleotides 5232-5297/1-88 in total 154 bp (5232 and 88 included) in sequence PLY2CG (Genebank accession number J02288). The polyomavirus core origin is also referred as PyV core origin or as minimal core origin.

The Minimum origin (MO) of BPV1 is defined as described in U.S. Pat. No. 6,479,279.

FR element refers to Epstein-Barr virus family of repeats. It comprises at least 16 EBNA1-binding sites. SEQ ID NO: 1 gives nucleotide sequence of one alternative synthetic FR-element. In this element 21 EBNA binding sites were used. The EBNA 1-binding sites in the FR-element do not need to be similar to each other. The EBNA 1-binding sites may be according to any one of SEQ ID NO: 3-6: (SEQ ID NO: 3 GGGTATCATATGCTGACT; SEQ ID NO: 4: GGGTATCATATGCTGACT; SEQ ID NO: 5 GGATAGCATATGCTACCC; SEQ ID NO:6: GGATAGCATATACTACCC) In the vectors according to this disclosure the EBNA-1 binding sites are separated by spacers.

"EBNA1" refers to viral transactivator for EBV and is encoded by nt 7421-8043 in EBV sequence with Genbank accession number V01555.

"E1" refers to the protein encoded by nt 849-2663 of BPV subtype1, or to nt 932-2779 of HPV of subtype 11, or to equivalent E1 proteins of other papillomaviruses, or to functional fragments or mutants of a papillomavirus E1 protein, i.e. fragments or mutants of E1 which possess the replication properties of E1.

"E2" refers to the protein encoded by nt 2594-3837 of BPV subtype 1; or to nt 2723-3823 of HPV subtype 11, or to equivalent E2 proteins of other papillomaviruses, or to functional fragments or mutants of a papillomavirus E2 protein, i.e. fragments or mutants of E2 which possess the replicating properties of E2.

"Minichromosomal maintenance element" (MME) refers to a region of the papilloma viral genome to which viral or human proteins essential for papilloma viral replication bind, which region according to this invention is essential for stable episomal maintenance of core origin in a host cell. Preferably, the MME is a sequence containing multiple binding sites for E2. According to this disclosure the MME contains at least 5 E2 binding sites. The sequential binding sites which constitute the MME need not be identical in sequence, but must be able to bind E2. SEQ ID NO:7 is one preferred example of the MME.

"E2 binding site" (E2BS) refers to the minimum sequence of papillomavirus double-stranded DNA to which the E2 protein binds. E2 binding site may be of BPV or of HPV. The affinities of the E2 binding sites vary and according to this disclosure E2 binding site means a high affinity binding site. In the vectors according to this disclosure the repetitive E2 binding sites are separated by spacers.

"Heterologous replication origin" refers to a system where the replication origin locates in a vector containing MME or FR-element of another virus species.

"A host cell" which is stably transformed according to the disclosure is a eukaryotic cell and preferably a mammalian cell, most preferably a human, mouse or hamster cell. The cell may be derived from any tissue. The host cell may be derived from CHO (hamster), COP (mouse) or human cell lines HEK293 or U2OS: CHOEBNALT85 is a cell line derived from CHO and expressing EBV EBNA1-protein and PyV-LT protein. 293EBNALT75 is a cell line derived from 293 and expressing EBV EBNA 1-protein and PyV LT-protein. U2OSEBNALTD3 is a cell line derived form U2OS and expressing EBV EBNA1-protein and PyV LT-protein.

"A gene of interest" refers to a gene encoding a gene product of interest such as a protein or RNA of interest.

"A gene product" refers to a product of the gene of interest. The product may be an expression product on RNA level or it can as well be an expressed protein or peptide. The gene products may be used for example as therapeutic or prophylactic purposes. The gene products may be endotoxine free products for diagnostic purpose. These uses are exemplary only and one skilled in the art would realize that there are other purposes as well according to this disclosure.

"Helper protein" refers to various viral proteins including viral regulatory proteins E1, E2, EBNA1, and LT.

"Extended episomal replication" refers to long term (during 20-30 cell generations) replication and maintenance of the expression plasmids and expression of protein of interest after transfection into the engineered cell without selective pressure We describe here a mechanism of extended replication of chimeric origins. We have developed PyV origin based constructs in conjunction with the segregation/partitioning elements from the EBV and the cell lines capable of supporting the replication and episomal maintenance of these plasmids. Polyomaviruses exhibit replication patterns that are uncoupled from the regulatory mechanisms of the host cell, so that each viral genome replicates many times within each cell cycle to the maximal level. The complete polyomavirus origin (wild type origin) includes transcriptional and replicational enhancer sequences, which dictate the origin activity and the efficiency of replication in specific cells by determining the availability of the replication factors and nucleotides. Papillomavirus origin replication control is similar to polyomavirus replication in the first, amplificational phase of the replication. However, in the latent replication phase copy number control mechanism is applied, which assures the controlled initiation of replication of the episomal viral genome in the latent replication phase. Epstein-Barr virus (EBV) uses entirely cellular replication machinery for initiation of the latent origin oriP replication, which strictly replicates once per cell cycle. Although the BPV-1 and polyomaviruses use the host replication machinery for viral genome replication, the initiation of replication is achieved by viral factors, while for stable maintenance with the EBV entirely cellular initiation and elongation machinery is used. The polyomavirus replicational enhancer can be exchanged with binding sites for different factors such as c-Jun and Gal4, without loosing its ability to promote replication (Guo et al., 1996).

The inventive step in this disclosure includes the finding that substitution of the wild-type PyV enhancer with at least 16 synthetic EBNA1 binding sites for the EBV protein, can replace replication enhancer function and makes it dependent on E2 protein. Similarly as in the previous disclosure (U.S. application Ser. No. 11/351,809) where addition of five or ten E2 binding sites to PyV wt origin did not cause additional replication activation, addition of the EBNA 1 binding sites to a PyV wt origin did not cause additional replication activation. Therefore, the viral origin seems to achieve in a host cell a maximum activity when a strong enhancer is present and after that point enhancement of replication is not possible, even if additional enhancer elements are added. This may be because of limitation of cellular factors or saturation of the nucleus with the active genetic elements. Accordingly, we observed many dead cells after transfection with PyV wt origin constructs.

It is known that EBNA1 protein of the EBV is necessary and sufficient for linking of the FR containing plasmids to the chromatin. The novelty of this disclosure includes the finding that FR functions outside of its natural replication origin and provides extended maintenance function only for constructs, which contain PyV core origin. In the case of wt PyV origin very strong transient replication was observed, however, it was impossible to rescue stable episomal replication of these plasmids, even after antibiotic selection for origin constructs. It is important to note that stably maintained constructs were in episomal state, no integration to host chromosomes was detected.

According to the present disclosure, EBV EBNA1 protein-dependent FR-element can provide extended maintenance functions to the PyV core origin plasmids in the presence of viral trans-factors. We have used stable replication assay and flow cytometric EGFP reporter expression assay for the analysis of the kinetics of the extended maintenance of the episomes. In the case of the BPV-1 and PyV, the origin of replication is fired several times during their amplificational replication in host cell S-phase and even during the stable replication of the BPV-1 the origin is not restricted to precisely once in each cell cycle. At the same time the EBV latent origin oriP replicates strictly once per cell cycle, the same way as chromosomal DNA. The present disclosure suggests that the extended maintenance of the episomes provided by the function of MME or FR-element, is not connected to the mode of replication of the episome. FR-element can provide an extended maintenance function to both types of origins—in its natural context within EBV latent origin oriP and in our hybrid replicon together with PyV core origin (SEQ ID NO:2).

The present disclosure also shows that the replication function is not connected to the stable maintenance function of the virus—replication origins of different viruses can be combined with different stable maintenance elements without the loss of either function. It has been shown previously that the cellular receptors of BPV-1 E2 protein and EBV EBNA1 protein, which link the episomes to mitotic host chromatin and therefore provide the stable maintenance function, are different. The present disclosure suggests that the different localization of the episome on mitotic chromosomes does not interfere with the replication of PyV core origin.

The Rate of Loss of Episomal Plasmids is Lower than in Control Plasmids

We have analyzed the episomal maintenance of the pMMEG, pMMEG* and pFRG* plasmids (Materials and Methods) in cells cultured without geneticine selection. These plasmids contained PyV minimal core origin (SEQ ID NO: 2) and either BPV-1 Minichromosome maintenance element (MME) or EBV FR-element. The viral trans-factors (either PyV LT and BPV1 E2 or PyV LT and EBV EBNA1 protein) were stably expressed in the cell line. For the analysis of the plasmid loss we measured the expression of the reporter gene EGFP (or d1 EGFP) with flow cytometry. In the case of plasmids containing the PyV minimal core origin and BPV-1 MME the rate of episomal loss was ~6% per cell division in the absence of geneticine selection. For plasmids containing PyV minimal origin and EBV FR-element, the rate of episomal loss was faster (~13%), but compared to the 22-30% rate of loss of the control plasmids (pEGFP-C1 and pd 1 EGFP-N1), which contained neither replication origin nor segregation element, this rate is still significantly lower. The rate of loss of plasmids containing PyV minimal core origin and FR-element (pFRG*) is also different from the previously published results of the rate of loss of several replicating plasmids that contained FR-element as stable maintenance factor, where the rate of loss was 2.1-7.8% (Wade-Martins et al., 1999) but it is very similar to the 15% rate of loss previously estimated for oriP containing plasmids (Hung et al., 2001). We have verified the requirement of FR-element in long-term experiment. For that we have deleted FR element from the pFRG-EGFP plasmid. Plasmids with or without FR element were electroporated into CHOEBNALT85 cells. Samples for Southern-Blot analysis were taken from different time-points (48 hours, 14, 21 and 22 days after transfection). As shown in FIG. 19, lines 1-4 plasmid (pFRG-EGFP) could be detected from all time points observed. At the same time plasmid (pFRG-EGFP-FR without FR element could be detected only 48 hours after transfection. In all other time points no plasmid could be detected within CHOEBNALT85 cells.

The examples presented below are meant to be descriptive and by no mean limiting the various embodiments of the present invention.

Materials and Methods Used in the Examples

Plasmids. MME-plasmids For constructing hybrid replicons, containing PyV origin (core origin), we used vector pUC19 as the basic backbone where we cloned 1, 5 or 10 head-to-tail copies of high-affinity E2 binding site 9. PyV wt and core origin were amplified by PCR from vectors pmu1046/CAT and pmu1047/CAT using primers Py4963 (5'-AGGGAGCTACTCCTGATG-3') (SEQ ID NO: 10) and Py174 (-CTACCACCACTCCGACTT-3') (SEQ ID NO:11). Amplified PyV origin fragments were digested with enzymes EheI and BclI and inserted between BamHI and HincII sites of pUC19 vector containing different number of BPV-1 E2 binding sites. In the vector the E2 binding sites exist together with spacers.

For constructing hybrid replicons (FIG. 1), containing PyV origin (core origin), we used vector pUC19 as the basic backbone and FR element originated from EBV genome (Strain 95-8; GenBank: V01555.2). FR element was cloned into the pUC19 containing Py core origin (SEQ ID NO: 2). Sequence of FR element used in plasmids comprised at least 16 EBNA1-binding sites separated by spacer sequences. FIG. 1 shows and FR element containing 21 EBNA1 binding sites and having a sequence according to SEQ ID NO: 1

Figure 2:
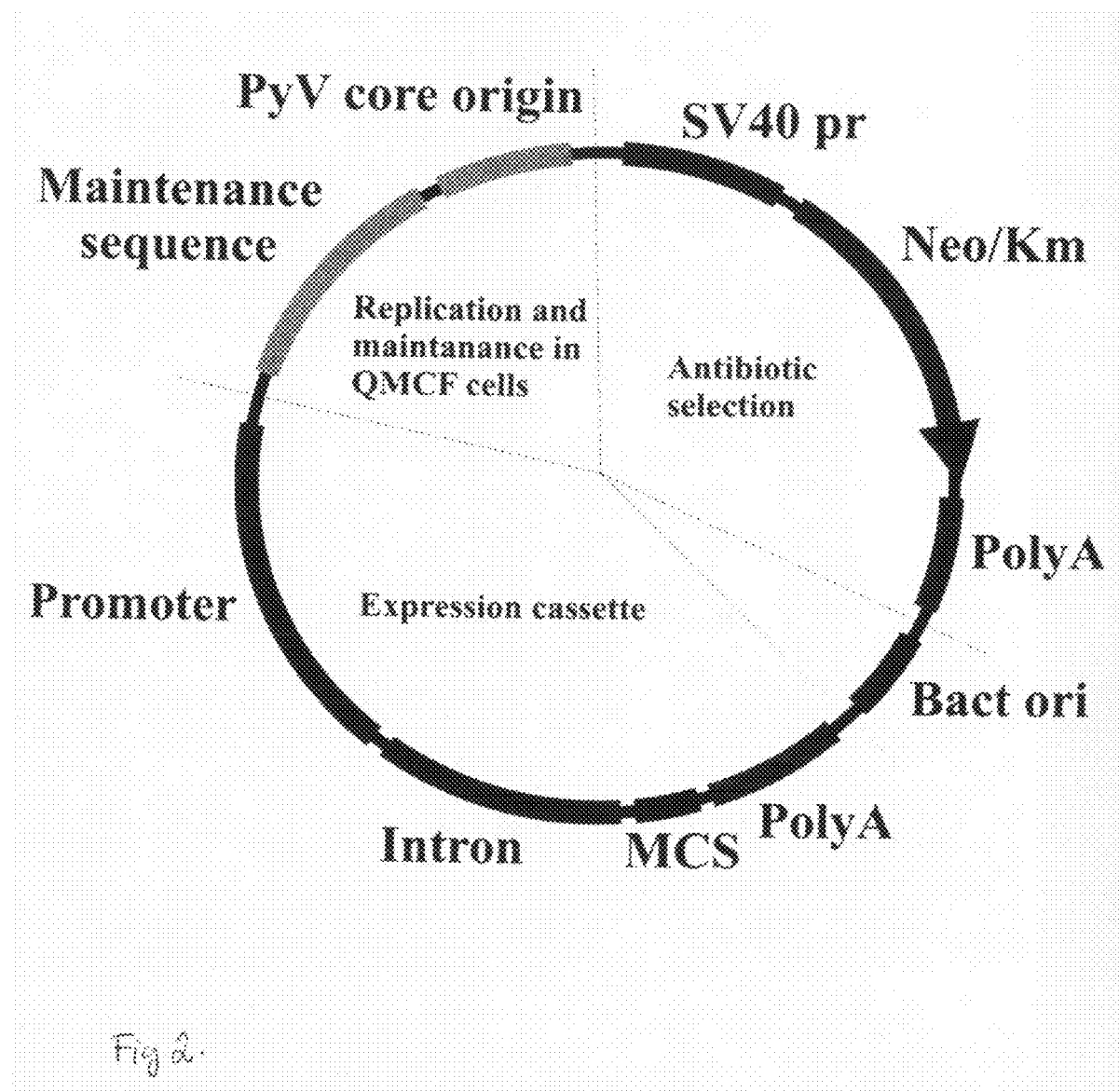
FIG. 2. Schematic representation of new generation expression plasmid. 1. Replication and maintenance in QMCF cells: Maintenance element—(Epstein-Barr Virus Family of Repeats (FR) (SEQ ID NO: 1) or Bovine Papillomavirus type I Minichromosome Maintenance Element (MME) SEQ ID NO: 7); Py origin of replication—murine polyomavirus origin of replication (SEQ ID NO:2); 2. Antibiotic selection: SV40 pr—SV 40 promoter (SEQ ID NO:17) controlling expression of Neo resistance gene; Neo/Km—Neomycin/Kanamycin resistance marker (SEQ ID NO: 18) for selection of plasmid containing cells in bacteria and eukaryotic cells; 3. Replication in bacteria: pMMB origin of replication (SEQ ID NO: 25); 4. Expression cassette: Promoter (CMV (SEQ ID NO:13), hEF 1α-HTLV (SEQ ID NO:14), hEF 1α (SEQ ID NO:8), RSV-LTR (SEQ ID NO:16), heIF4A (SEQ ID NO:9) or β-actin (SEQ ID NO:12)); Intron—hEF1α intron (SEQ ID NO: 19) in 5' position from gene of interest cDNA; MCS—multicloning sequence; polyA—SV40 polyadenylation sequence (SEQ ID NO:15) (regulating expression of Neo/Km and gene of interest simultaneously).

For construction of new generation pQMCF plasmids, modified pFRG vector (pFRG-shorty-SV40 pA) without expression cassette for protein of interest was used. Plasmids containing different promoters (CMV, hEF1α, heIF4a, RSV-LTR, β-actine and hEF1α-HTLV) and hEF1α intron in 5' position from protein of interest were constructed in pUC19 cloning vector. DNA fragments containing different promoters with intron sequence were cloned into pFRG-shorty-SV40pA which contains also SV40 polyA sequence (FIG. 2). SV40 PolyA sequence regulating expression of Neomycine resistance and gene of interest simultaneously. After that multi-cloning sequence containing sites for single-cutting enzymes for cloning of genes of interest were added into the vectors (Table 1).

TABLE 1 pQMCF and pQMME expression vectors and promoters used for expression of protein of interest.

| FR-based vectors | MME-based vectors | Promoter |
| --- | --- | --- |
| pQMCF-1 | pQMME-1 | CMV |
| pQMCF-2 | pQMME-2 | hEF1α-HTLV |
| pQMCF-3 | pQMME-3 | heIF4a |
| pQMCF-4 | pQMME-4 | β-actin |
| pQMCF-5 | pQMME-5 | RSV-LTR |
| pQMCF-6 | pQMME-6 | hEF1α |

For construction of antibody- or VLP-expressing vectors another expression cassette containing CMV, hEF1α-HTLV or RSV-LTR promoter for expression of antibody light- or heavy chain or gag protein was added into the pQMCF-1 plasmid.

Construction of cell lines. For construction of cell lines, which express BPV-1 wt E2 protein and its mutant forms E39A and R68A, the vector pBabePuro was linearized using enzyme SalI and was ligated with equal amount of E2 expression vectors (pCGE2, pCGE2/R68, pCGE2/E39), which were linearized with XhoI endonuclease. 1 μg of ligated hybrid plasmids was electroporated into COP5 cell line. COP5 cell line is derived from mouse C127 cells (ATCC CRL-1804) and described in Tyndall et al. 1981. Electroporation experiments were preformed with a Bio-Rad Gene Pulser with capacitance and voltage settings of 975 μF and 220 V. For selection puromycin (2 μg/ml) was added. The expression of the proteins was analyzed by Western blot.

A cell line which expresses wt E2 and carries neomycine selection cassette was constructed by the same protocol described above, using vector pBabeNeo instead of pBabePuro.

A cell line expressing PyV T-antigens and EBV EBNA1 protein was generated as a result of transfection of the NotI linearized plasmid pBabePuro/EBNA1 (EBNA1 coding sequence inserted into EcorI/SalI sites in pBabePuro vector) into COP5 cell line and selection for puromycin (2 μg/ml). The expression of the proteins was analyzed by Western blot. The cell line was named COP5EBNA1/Puro.

Sometimes cell line CHO4.15 was used. This cell line is derived from CHO-K1 cell line (ATCC CCL 61) and described in Ustav 1993. CHO, HEK293 and U2OS derived cell lines expressing EBV EBNA1, PyV LT, BPV E2 were constructed using the same method as used for construction of COP derived cell lines.

Cells and transfection. COP5 cells (Tyndall et al., 1981) and its derivatives COP5E2/Puro, COP5E2/Neo COP5R68/

Puro, COP5E39/Puro, COP5EBNA1/Puro expressing polyomavirus T-antigens and BPV-1 wt E2 or its mutant forms or EBNA1 were grown in Iscove's modified Dulbecco's medium ("Difco") supplemented with 10% fetal calf serum. For selection G418 (500 μg/ml) or puromycin (2 μg/ml) were added, depending on selection marker. Electroporation experiments were performed with a Bio-Rad Gene Pulser with capacitance and voltage settings of 975 μF and 220 V, respectively.

COP5E2/Puro cells transfected with neomycin-constructs were selected with G418 at 500 μg/ml. COP5E2/Neo cells co-transfected with pBabePuro (Morgenstern, J. P., and H. Land. 1990) were selected with puromycin at 2 μg/ml. After transfection with plasmids carrying geneticine resistance marker and GFP coding sequence, COP5EBNA1/Puro cell line was grown in IMDM medium containing 500 μg/ml G418 (medium contained no puromycin).

The CHOEBNALT 85 cells are adapted to serum-free suspension culture in 1:1 mixture of CD CHO and 293 SFMII medium supplemented with L-Glutamine, HT Supplement and puromycin (20 μg/ml). CD CHO Medium (Invitrogen Cat. No. 10743-029) supplemented with 8 mM Lglutamine and 20 ml/l HT Supplement and• 293 SFM II Medium (Invitrogen Cat. No. 11686-029) supplemented with 4 mM Lglutamine.

Electroporation were performed with a Bio-Rad Gene Pulser with capacitance and voltage settings of 975 μF and 230 V. 6×106 CHOEBNALT 85 cells were transfected with pQMCF plasmids. 48 hours after transfection G418 is added at final concentration 700 μg/ml.

The 293EBNALT 75 cells are adapted to serum-free suspension culture in 1:1 mixture of Pro293s-CDM and 293 SFMII medium supplemented with L-Glutamine and puromycin. To prepare a 293 medium for 293EBNALT 75 cells mix in equal amounts: Pro293s-CDM (BioWhittaker™ Cat. No. 12002-026) and 293 SFM II Medium (Invitrogen Cat. No. 11686-029), supplemented with 4 mM L-Glutamine and puromycin to the final concentration of 0.8 μg/mL. For electroporation 4·106 viable cells were taken. Electroporation settings are 975 μF and 150V. 48 hours after transfection G418 is added at final concentration 10 μg/ml.

The U2OSEBNALTD3 cells are grown in DMEM high Glucose (4.5 g/L) with Sodium Pyruvate and Lglutamine (PAA E15-843 or equivalent); 10% Foetal Bovine Serum (FBS)(PAA E15-151 or equivalent) in the presence of Puromycin (2 μg/mL). For transfection $3.5 \times 10^6$ cells from dish containing cells growing in logarithmic growth phase with 70-80% confluency were used. Electroporation settings are 250V; 975 μF.

Southern blot analysis. Total DNA was extracted from cells following standard protocol. Extraction of low-molecular-weight DNA from cells as well as analysis of origin constructs levels in both low molecular weight and total DNA preparation were performed as described previously (Ustav and Stenlund, 1991; Piirsoo and Ustav 1996). Specific probes were labeled with [$^{32}$P]dCTP by random-hexamer-primed synthesis using DecaLabel kit (Fermentas, Lithuania). Hybridizing species were visualized by autoradiography. Radioactive signals on the blots were quantified on PhosphorImager using ImageQuant software (Molecular Dynamics, Amersham Biosciences, UK).

Immunoprecipitation. Cells ($1.5 \times 10^7$) were lysed with ice-cold 1% sodium dodecyl sulfate (SDS)-phosphate-buffered saline on ice, collected in a 15-mil tissue culture tube, and sonicated. From this step an aliquot for the Bradford assay was taken. SDS was diluted to 0.1% by adding ice-cold radioimmunoprecipitation assay (RIPA) buffer (50 mM Tris-HCl, pH 8.0, 150 mM NaCl, 1% NP-40, 0.5% dexycholate, 0.1 mM dithiotreitol (DDT), 0.5 mM phenylmethylsulfonyl fluoride, protease inhibitors). The insoluble fraction was sedimented by centrifugation at 5,000×g for 15 min. The soluble fraction was transferred to a new tube and incubated with 5H4, 3E8, 1'E4 and 3F12 antibodies over night at 4 C. Then protein G-Sepharose (Amersham Biosciences) was added and incubated for 1 h. Sepharose beads where washed three times with RIPA buffer and resuspended in SDS loading buffer and subjected to immunoblotting analysis with horseradish peroxidase-conjugated eE11 (subclone of MAb 3F12 (antibody (Quattromed AS, Tartu, Estonia).

Immunoblotting. Total protein from the same number of cells lysed in standard loading buffer supplemented with 100 mM DDT was separated by electrophoresis on 8% polyacrylamide-SDS gel and transferred to Immobilon-P membrane (Millipore, USA). Antibody 1E4 (Kurg et al., 1999) was used to detect E2 proteins. Antibodies BM3167 and BM1083 (DPC Biermann) was used to detect EBNA1 protein. Peroxydase-conjugated goat-anti mouse antibody and the enhanced chemoluminescence detection kit (Amersham Biosciences) were used for subsequent developing of the blot, using a standard protocol provided by the supplier.

The plasmid rescue assay was performed for detection of the episomal state of the plasmid as described previously in Männik et al 2003. Two micrograms of uncut genomic DNA was electrotransformed in to *Escherichia coli* strain DH10B. The electrocompetent cells were prepared and the transformations were performed using a Pulser apparatus and 2-mm electroporation cuvette (Bio-Rad Laboratories, Hercules, Calif.) according to the manufacturer's instructions. The cells were recovered by centrifugation and were grown on medium containing ampicillin at 100 Plasmid DNA from single colonies was purified and analyzed using restriction endonucleases.

Flow cytometry analysis. EGFP expression was analysed by flow cytometry using Becton-Dickinson FACSCalibur flow cytometer with associated CellQuest software. 100 000-200 000 signals were analysed from each sample. The threshold for autofluorescence was set to 99% of the signals from the mock-transfected control cells. All the signals above the threshold were considered to correspond to EGFP-positive cells. For calculating the episomal rates of loss in the FIG. 8, EGFP expression data was analyzed on days 0 and 12 (pEGFP-C1, pd1EGFP-N1), on days 0 and 55 for pMMEG, on days 0 and 37 for pMMEG* and on days 0 and 30 for pFRG*. For this calculation first order rate-of-loss model was used: rate of loss $\lambda = (-1/t)(\ln N_t/N_o)$. $N_o$ is the percentage of the green cells at the beginning of the experiment of non-selective conditions and $N_t$ is the percentage of the green cells after t generations.

Expression of luciferase analysis. The expression analysis was done in CHO4.15 E2 cell line with plasmids carrying different regulatory elements and recombinant EGFP-luciferase gene. The cells were electroporated with the equimolar amounts of the EGFP-luciferase vectors. For negative control the cells were transfected with carrier DNA only. In different time-point, the cells were washed with PBS and lyzed with appropriate amount of 1*CCLR agent (Promega). Luciferase activities in the samples were measured using Luciferase Assay System kit (Promega) and plate reading luminometer (Tecan). Different dilutions of the samples in 1*CCLR buffer were used for verifying that all measurements are done at linear range. For normalisation of the activities of to the total protein in the samples, these were diluted 4 times with water. Thereafter, BCA assay kit (Pierce) was used for measurements.

Western-Blot Analysis

Total protein from the same number of cells or supernatant of equal number of cells were taken for analysis. Cells were lysed in standard loading buffer (Laemmli buffer) supplemented with 100 mM DDT. Supernatant of the cells was mixed with Laemmli buffer with or without DDT. Samples were separated by electrophoresis on 8 to 12% polyacrylamide-SDS gel and transferred to Immobilon-P membrane (Millipore, USA). Antibody 1E4 (Kurg et al., 1999) was used to detect E2 proteins. Antibodies BM3167 and BM1083 (DPC Biermann) was used to detect EBNA1 protein. Peroxydase-conjugated goat-anti mouse antibody and the enhanced chemoluminescence detection kit (Amersham Biosciences) were used for subsequent developing of the blot, using a standard protocol provided by the supplier. For detection of DNaseI, CDNF or ETAR protein expression appropriate antibodies were used and for visualization of expression alkaline-phosphatase conjugated secondary antibodies were used.

Example 1

Figure 21:
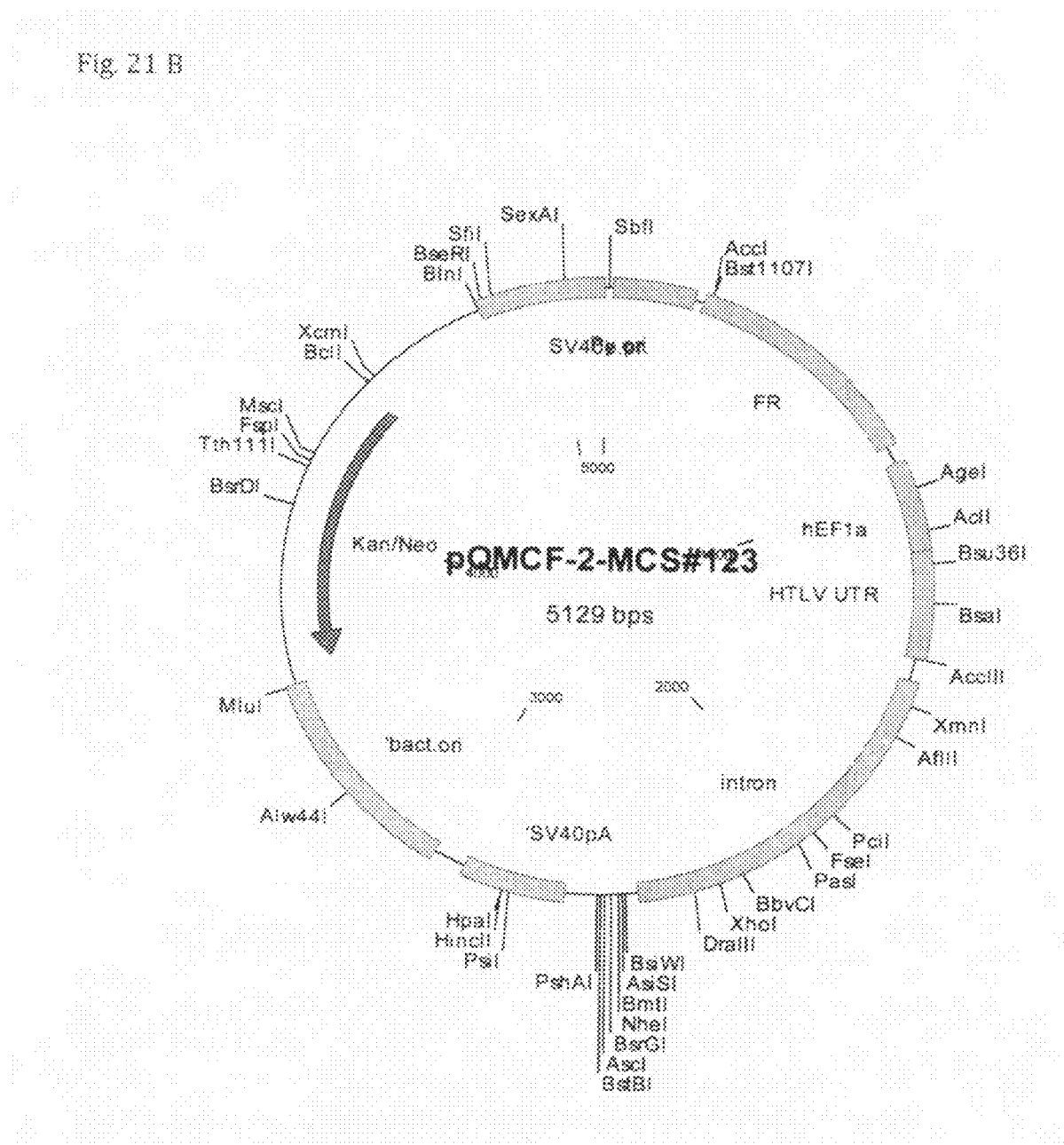
Figure 21:
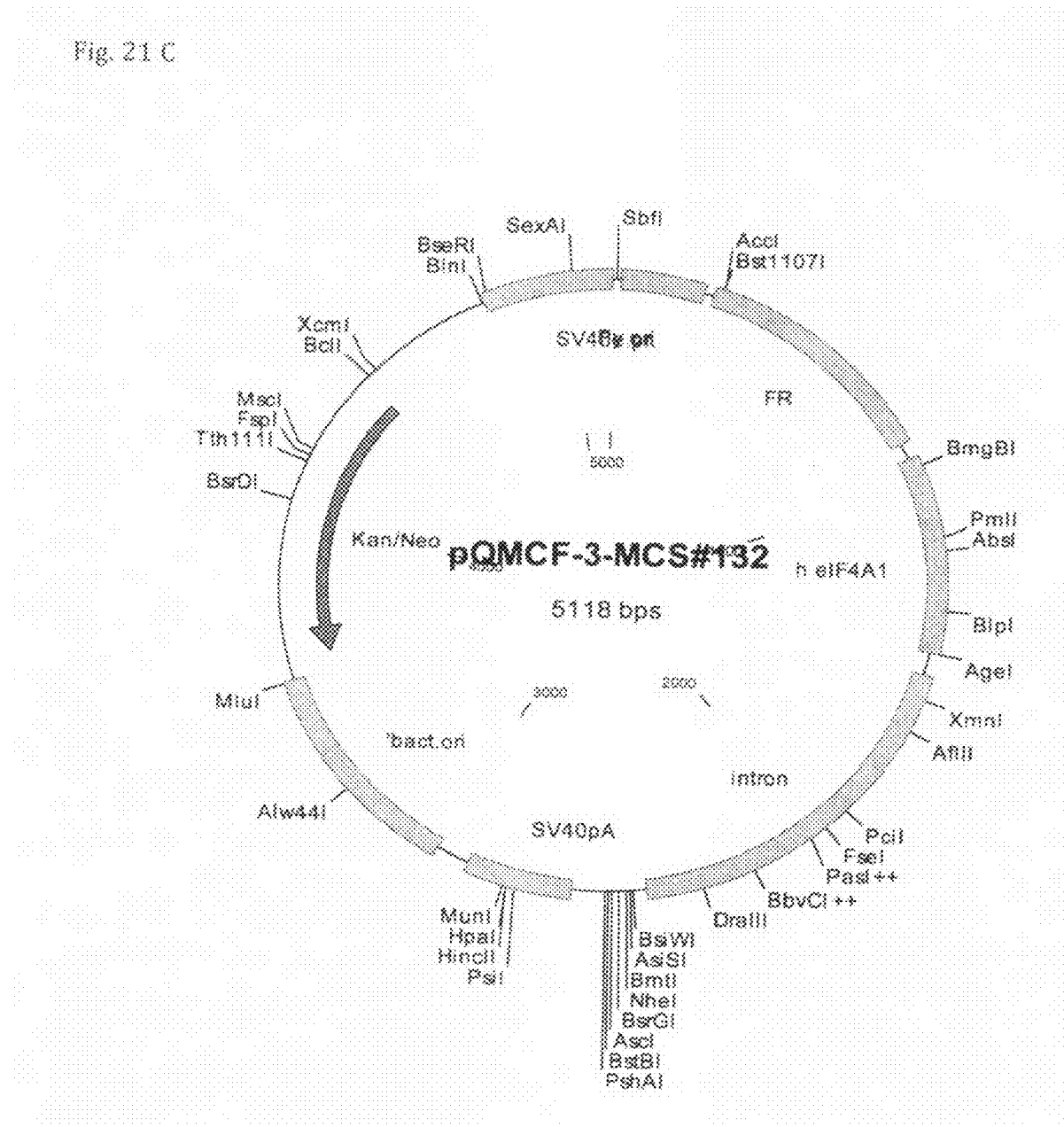
Figure 21:
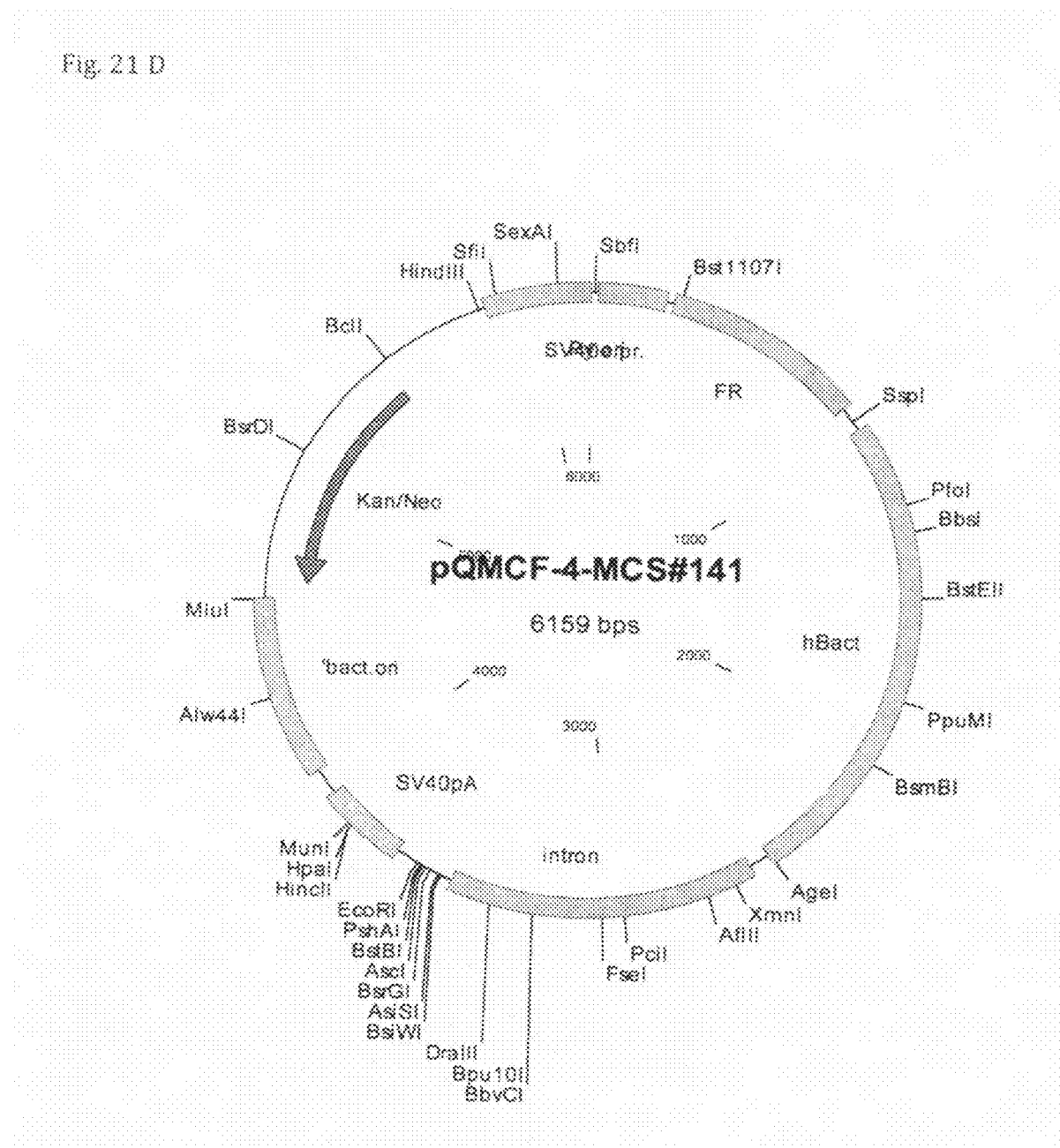
Figure 21:
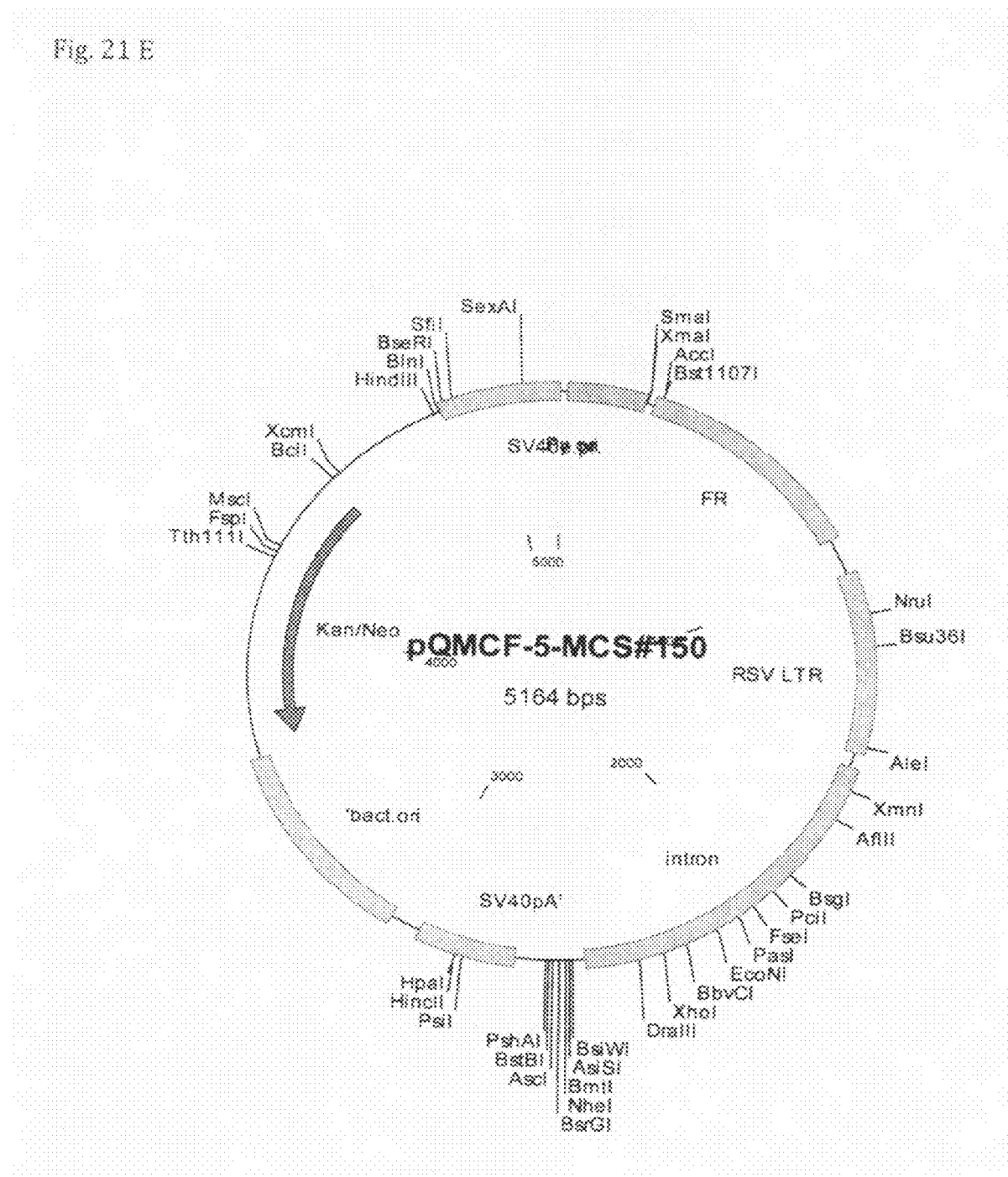
Figure 21:
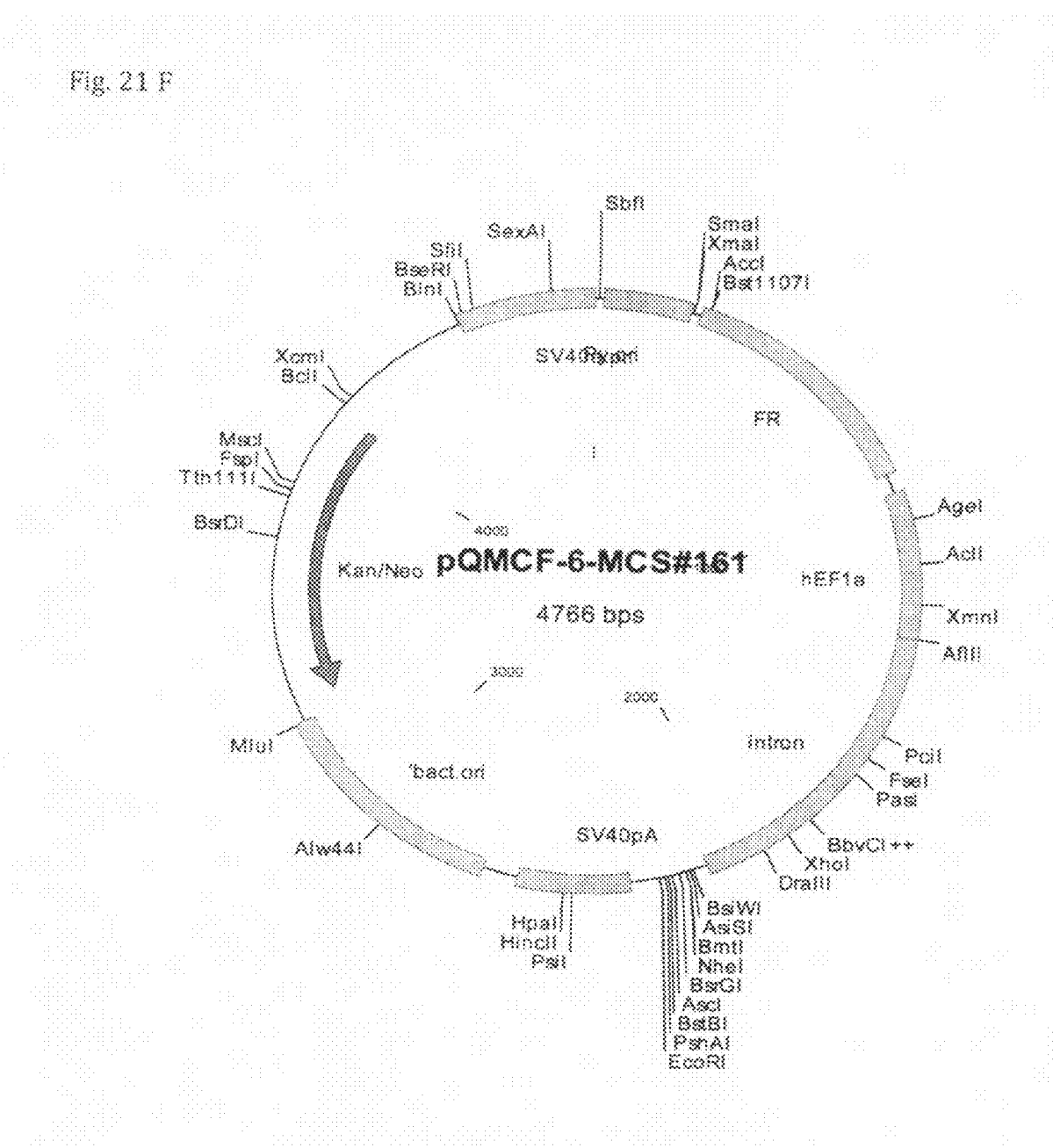

PyV Hybrid Origin Constructs Including PyV Core Origin and EBV FR Element and Construction of Plasmids for Extended Episomal Maintenance FIG. 1 schematically shows mouse polyoma virus core origin of replication (SEQ ID NO: 2) and FR (Family of repeats) element. Here, FR element (SEQ ID NO: 1) contains 21 possible EBNA-1 binding sequences. Table 1 above and FIG. 21 show the novel QMCF-plasmids according to this disclosure. pQMCF1 contains CMV promoter-driven expression cassette. pQMCF2 contains EF1α-HTLV promoter-driven expression cassette. EF1α-promoter GenBank J04617.12 and HTLV leader sequence GenBank AB513134). pQMCF-3 contains heIF4a promoter-driven expression cassette (heIF4a GeneBank J04617.1) pQMCF-4 contains β-actine promoter-driven expression cassette. pQMCF-5 contains RSV-LTR promoter-driven expression cassette.

Example 2

Comparison of BPV-1 Mme and EBV FR Element in Providing Segregation/Partitioning Function to the PyV Core Origin Plasmids Maintenance of plasmids containing PyV core origin, MME or FR, selection marker (geneticine resistance) and green fluorescent protein marker (either long half-life EGFP or short half-life d1EGFP) was analyzed by flow cytometry. The flow cytometry analysis was conducted in the COP5EBNA1/Puro cell line with plasmid containing PyV core origin, FR-element, selection marker (geneticine resistance) and green fluorescent protein marker (short half-life d1 EGFP) (pFRG*). In this case the replication function of the plasmid is provided by PyV core origin and LT protein and the segregation/partitioning function is provided by FR-element and EBNA1 protein of the EBV. The results are similar to the flow cytomery analysis with plasmids pMMEG and pMMEG* in COP5E2/Puro cell line. Transfected cells were grown in continuous culture in the presence or absence of geneticine for up to 75 days. Selection of the transfected COP5EBNA1/PuroFRG* for geneticine resulted in the cell culture, which had approximately 40% d1EGFP positive cells (FIG. 20 D). When the geneticine selection was removed the percentage of d1EGFP-positive cells decreased from 40% to 1% in 30 days. When the geneticine selection on COP5E2/PuropFRG* cell line was restored at this point, the proportion of EGFP expressing cells increased back to the initial level (FIG. 20D). These results show that episomal persistence of the plasmid occurs with certain efficiency, which is different from 100%. Clearly also, EBNA1/FR and E2/MME elements confer comparable segregation/partitioning functions for the PyV core origin reporter plasmids in the cell models.

To exclude the possibility that the loss of EGFP fluorescence is due to inactivation of the promoter of EGFP, we also analyzed the DNA content in the cells. After removal of geneticin selection total DNA was extracted from cells and digested with MluI (linearizes pMMEG* and pFRG* plasmids) and DpnI. Equal amounts of total DNA were then analyzed using Southern blotting with a radioactively labelled probe against the pMMEG* or pFRG* plasmid. The loss of the episomal plasmid DNA from the cells grown without Geneticin selection correlates with the flow cytometry analysis (results not shown). On the other hand, these results indicate that EGFP fluorescence was indeed measured from plasmids which exists in the episomal state. In the case of plasmid integration the hybridization signals remained constant.

Example 3

Production of Recombinant Proteins and Generation of Cell-Based Assay (CBA) Test-System for Development Drug Candidates We have constructed set of new expression plasmids containing polyoma virus (PyV) core origin (SEQ ID NO: 2) in combination with Family of Repeats (FR) of Epstein-Barr Virus, an element for extrachromosomal genome maintenance of Epstein-Barr virus (EBV) or MME (minichromosome maintenance element) from Bovine Papilloma virus (BPV-1) in proliferating cells. (construction of the plasmids is described above and in previous patent application Ser. No. 11/351,809 which is incorporated herein by reference; and plasmids are shown in FIG. 22). Such hybrid origin uses mouse polyomavirus (PyV) Large-T antigen for initiation of plasmid replication during S-phase of the cell cycle and EBV EBNA-1 or BPV E2 protein for segregation/partitioning of the extrachromosomal plasmid into the daughter cells during cell division. We engineered six different promoters—four human originated cellular promoters (EF1α; EF1α-HTLV; heIF 4a; β-actine) and two viral promoters Cytomegalovirus immediate early (CMV) and Rous Sarcoma Virus proviral Long Terminal Repeat (RSV-LTR) driven expression cassettes in new expression vectors (FIG. 21). Different strength of selected promoters allows modulation of the protein of interest expression depending on purpose of use of expression system. In all cases the expression cassettes were equipped with hEF1α intron (GenBank J04617.1) locating at 5' position from gene of interest coding sequence. SV40 polyadenylation (polyA) sequence regulating expression of Neo/Km and gene of interest simultaneously is used in protein of interest expression cassettes. New generation plasmids are suitable for expression of recombinant proteins or target-proteins for generation of CBA-s. Cell lines for expression of recombinant proteins and for generation of cell based assays are different. For protein expression modified suspension cell lines based on CHO or HEK293 are used. For generation of CBA-modified CHO, HEK293, U2OS adherent cell lines are suitable.

A. Testing of pQMCF and pQMME Expression Vectors Using Gaussia Luciferase as Test System in Transient Expression of Reporter Gene To characterize new expression vectors we use gaussia luciferase as reporter system. For analysis of pQMCF vectors suspension CHOEBNALT85 and 293EBNALT75 cell line was used, for analysis of pQMME vectors CHOmLTE2 63 cell line was used. In FIG. 3A, results of gaussia luciferase activities using different vectors in suspension CHOEBNALT85 and 293EBNALT75 is shown. In FIG. 3B, results of gaussia luciferase activities using different vectors in suspension CHOmLTE2 is shown.

Figure 3:
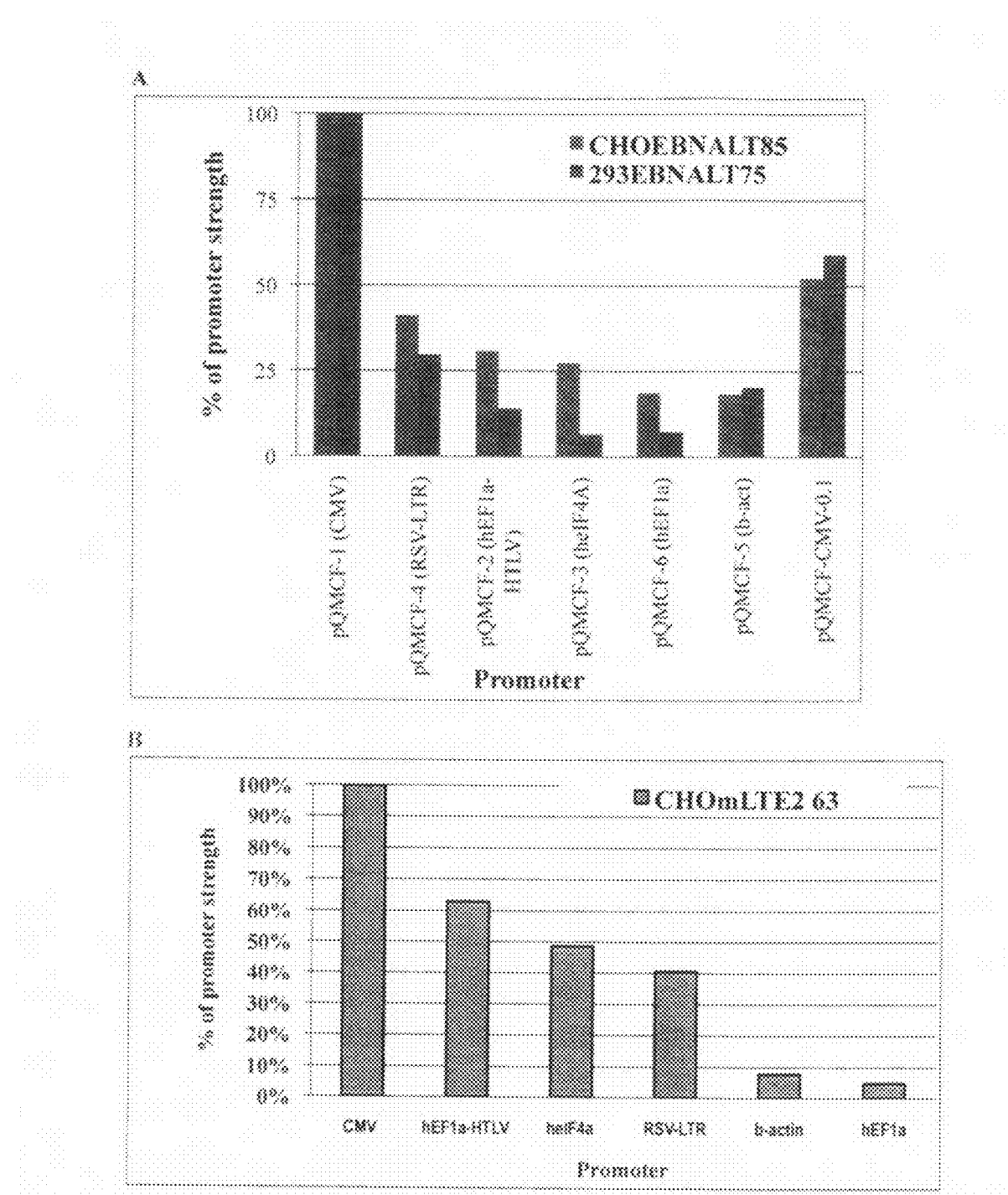
FIGS. 3A and B. Strength of different promoters used in pQMCF and pQMME plasmids. Gaussia luciferase gene was used as reporter and data is represented as relative promoter strength compared to strongest CMV promoter-3' intron containing vector (pQMCF-1/pQMME-1). A. Promoter comparison in different pQMCF vectors. B. Promoter comparison in different pQMCF vectors. Also comparison with old version pQMCF-CMV-0.1 vector is represented in comparison to pQMCF-1.

Activity of luciferase was measured 24 hours after transfection. As shown in FIG. 2A, CMV promoter in pQMCF-1 is approximately two times higher compared to our initial vector pQMCF-CMV-0.1 (modified plasmid pFRG). Also in pQMME-1 CMV promoter exhibits highest activity compared to all other promoters. All other promoters in pQMCF show two to four times lower activity compared to pQMCF-1 vector (FIG. 3). In pQMME expression vectors hEF1α, heIF4a and RSV-LTR promoters are approximately two-times weaker than CMV promoter. Other two promoters (β-actin and hEF1α) exhibit 10-15 times lower activity compared to CMV promoter. Differences in promoter strength in QMCF cell lines makes these useful for expression of those proteins which high-level expression is toxic to the cells and allows modulate protein of interest expression level.

Activity of luciferase was measured 24 hours after transfection. As shown in FIG. 3, CMV promoter in pQMCF-1 is approximately two times higher when compared to another pQMCF-CMV-0.1 vector containing different configuration of expression cassette (CMV-promoter and 3' intron). All other promoters show two to four times lower activity as compared to pQMCF-1 vector (FIG. 3) which makes these promoters useful for expression of proteins which are toxic to the cells in high-levels.

Figure 4:
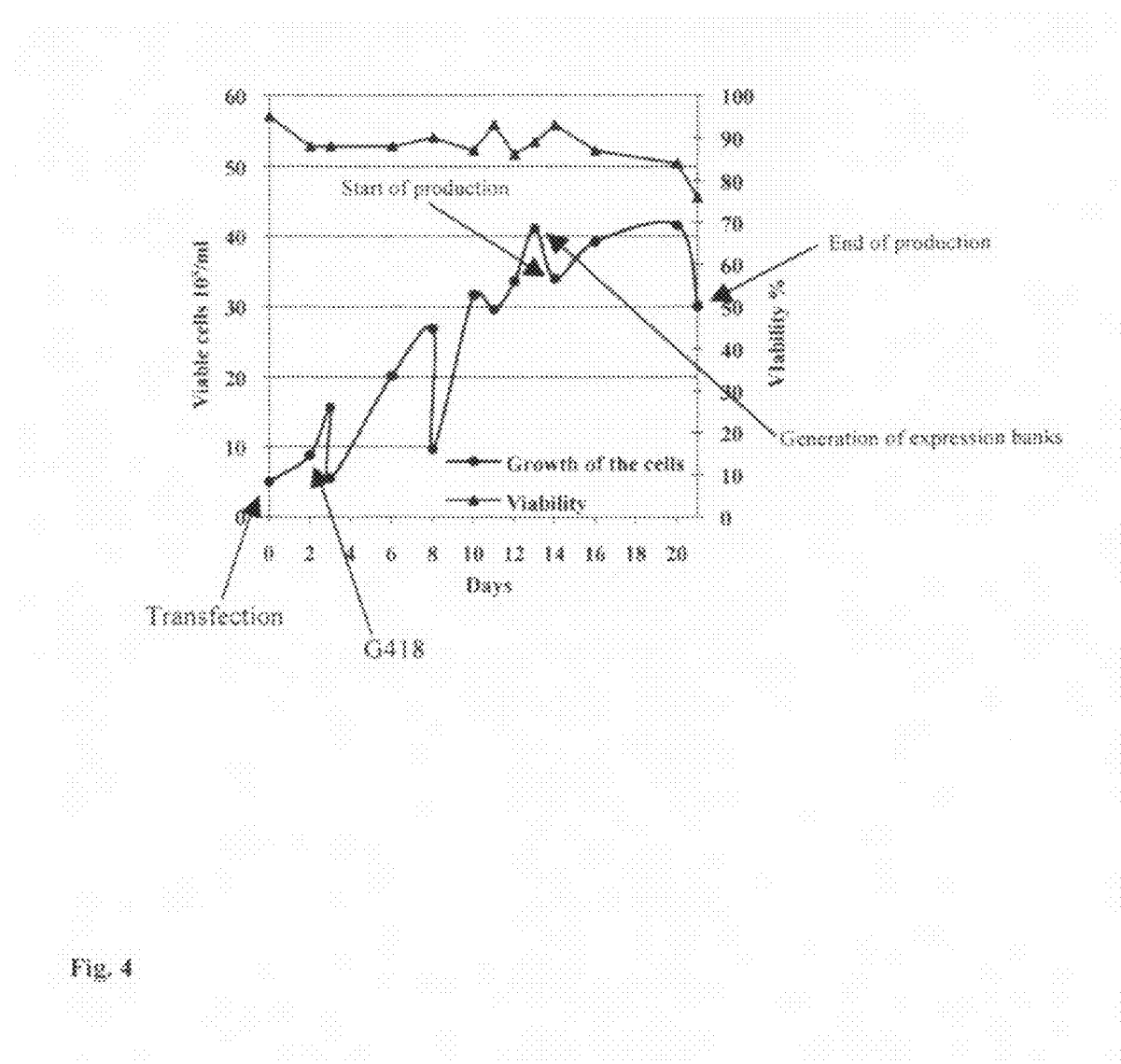
FIG. 4. Growth of the CDNF-expressing CHOEBNALT85 cell culture. 48 h after transfection G418 (700 µg/ml) was added. 12 days after transfection expression cell bank was generated. From day 13 to 21 the production phase was performed. Temperature was reduced to 30° C., additional nutrients were added to the medium. The viability of the cell culture was more than 85% during antibiotic selection and production. At day 21 when viability of the culture starts to decline, supernatant of the culture was clarified by centrifugation and filtered through 0.45 µm filter.

B. Use of the Novel Constructs, Vectors and Cell Lines of this Disclosure for Expression of Human Neurotrophic Factors e.g. Expression of Human CDNF cDNA encoding human CDNF protein (UniProtKB/Swiss-Prot Q49AH0) was cloned into all new pQMCF vectors (pQMCF-1 to pQMCF-6, vectors are shown in FIG. 21) and expressed in CHOEBNALT85 cell line. In FIG. 4, growth of the CHOEBNALT85 cells expressing CDNF [pQMCF-1-CDNF] is shown.

The expression of the CDNF was analysed in the cells as well as in culture media after transient transfection using electroporation of the QMCF vector encoding CDNF. Transfection efficiency of the CHOEBNALT85 suspension cells was around 85%. As shown on FIG. 5, CDNF is expressed effectively in cells carrying the leader peptide as well as processed CDNF. At the same time only processed CDNF can be found in the culture media, indicating that only processed form of the CDNF is secreted out of the cells. Approximately 9-12 days after transfection production cell bank could be generated ($1 \times 10^7$ cells/vial). Human CDNF expression by cells taken from expression cell bank is comparable to the expression started by newly transfected CHOEBNALT85 cells.

Stability of pQMCF Expression Vectors

Figure 5:
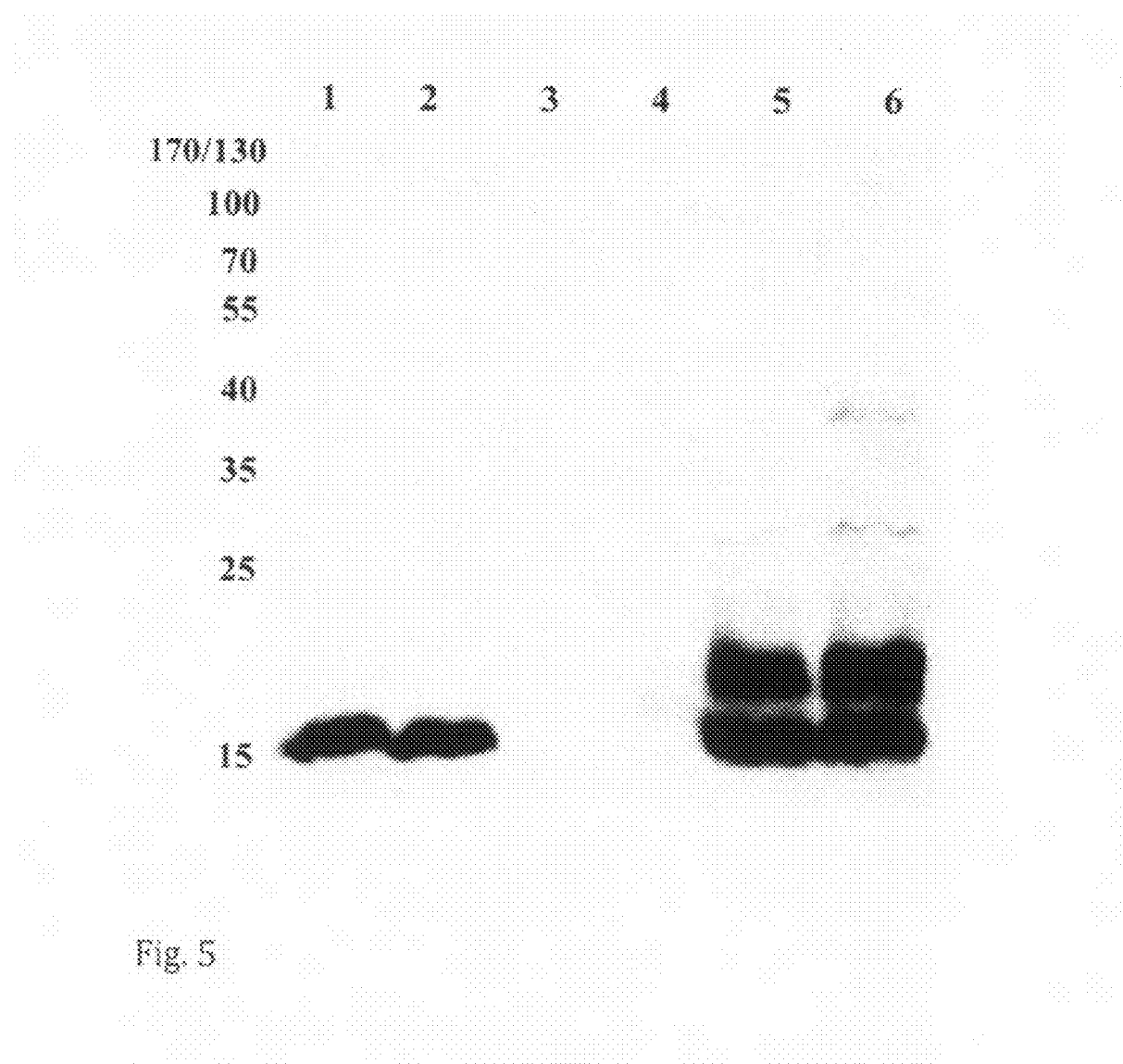
FIG. 5. Analysis of expression of the CDNF by CHOEBNALT85 cells using Western Blot 48 hours after transfection. Lane 1. PageRuler Prestained Protein Ladder (#SM0671, lot: 00036958, Fermentas); lane 2—17 µL of the supernatant from cells transfected with 1 µg of the CDNF expression vector; lane 3—17 µL of supernatant from the cells transfected with 5 µg of the CDNF expression vector; lane 4—17 µL supernatant from the untransfected CHOEBNALT85 cells; lane 5—17 µL of the untransfected CHOEBNALT85 cell lysate; lane 6—17 µL of the cell lysate transfected with 1 µg of the CDNF expression vector; lane 7—17 µL of the cell lysate transfected with 5 µg of the CDNF expression vector.
Figure 6:
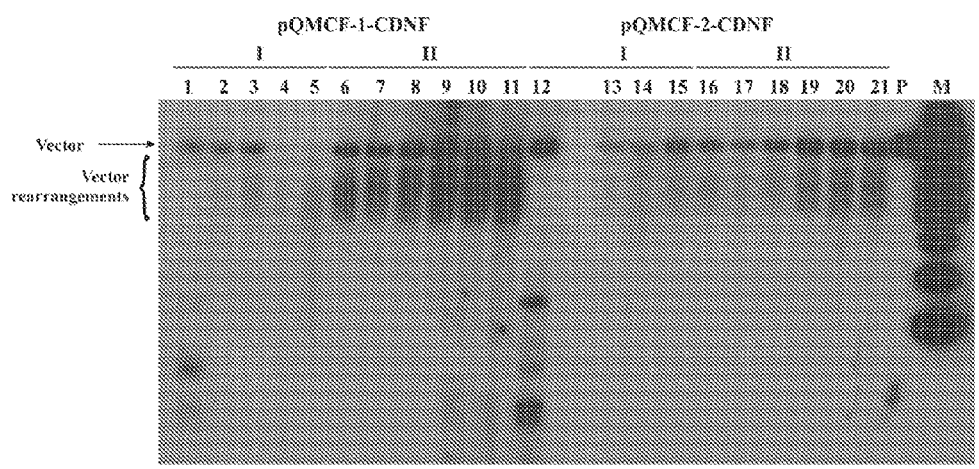
FIG. 6. Southern-Blot analysis of CDNF production plasmids. Lines 1-12 pQMCF-1-CDNF (CDNF expressed under control of CMV promoter). Lines 13-21 pQMCF-2-CDNF (CDNF under control of hEF1α-HTLV promoter). I and II designated cells transfected and grown from production cell bank, respectively. Line 1 and Line 12 designate time point 48 hours after transfection. Lines 2, 6, 13 and 16 designate time point at the beginning of production. All other lines—different time points during CDNF production phase.

We have seen that one important reason for plasmid instability during production phase is the dependence of the protein of interest on the expression level. The stress generated due to the over-expression of the protein depends strongly on the physiological effect of the protein and level of expression. We have analyzed by Southern-Blot method the intactness of the input plasmid in CHOEBNALT85 suspension cell line 48 h after transfection, after selection, and before production phase and during production. As shown in FIG. 5 in the CDNF expression vector (pQMCF-2-CDNF) containing EF1α-HTLV promoter (HTLV leader sequence—GeneBank AB513134; hEF1α promoter—GenBank J04617.1) exhibits the least plasmid rearrangements and reduction of the plasmid copy-number as compared to CMV promoter driven vector (pQMCF-1-CDNF) both during the expression of CDNF originated from transfection and production cell bank (for more detailed information is provided in FIG. 6 legend).

Figure 7:
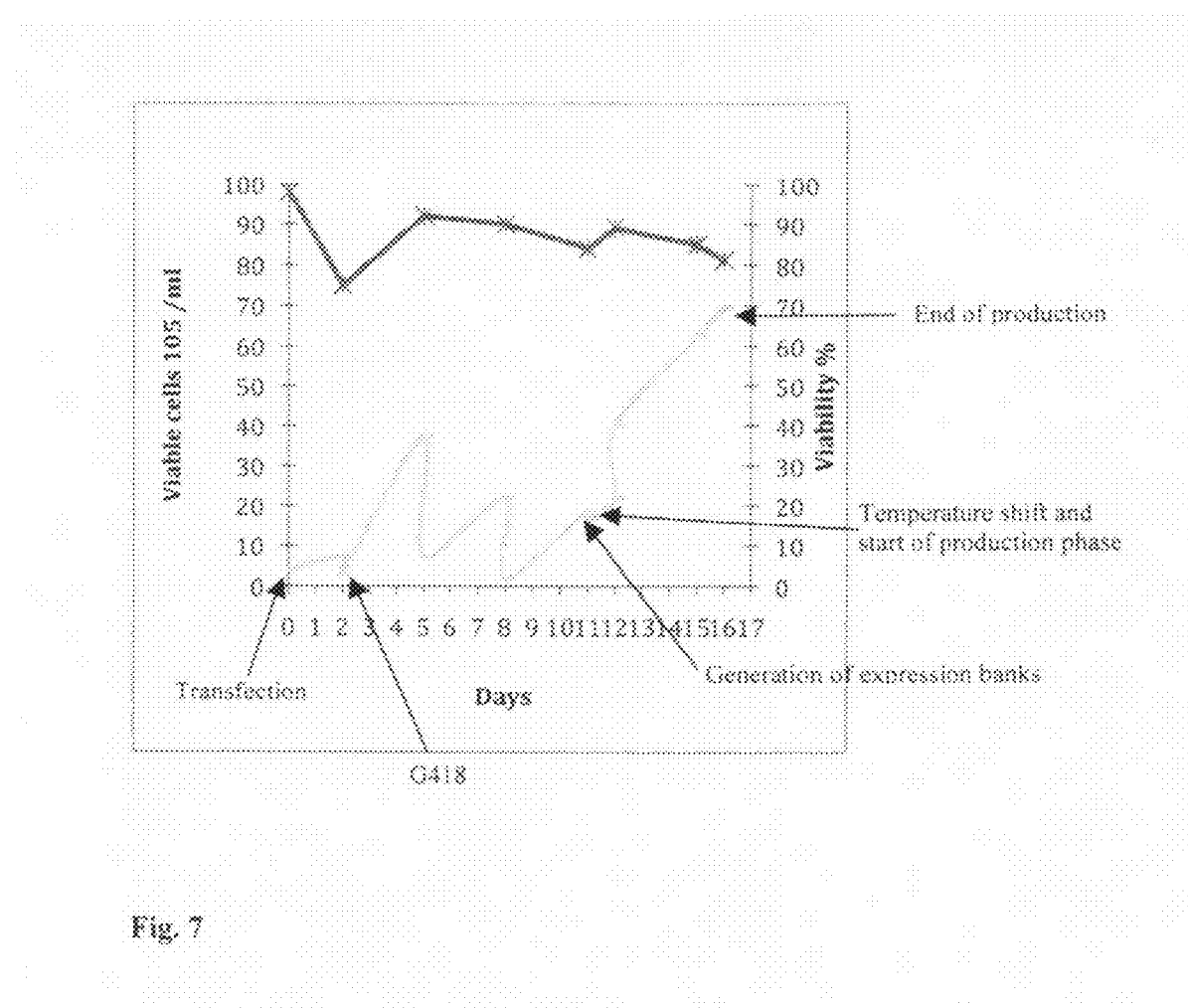
FIG. 7. Growth of the bovine DNaseI-expressing CHOEBNALT85 cell culture. 48 h after transfection G418 (700 μg/ml) was added. 12 days after transfection expression cell bank was generated. From day 13 to 21 the production phase was performed. Temperature was reduced to 30° C., additional nutrients were added to the medium. The viability of the cell culture was more than 85% during antibiotic selection and production. At day 17 when viability of the culture starts to decline, supernatant of the culture was clarified by centrifugation and filtered through 0.45 μm filter.

C. Expression of Recombinant Bovine DNaseI Using the Novel Constructs Vectors and Cell Lines of this Disclosure cDNA of Bovine DNaseI protein was cloned into the different pQMCF expression vectors (pQMCF-1 to pQMCF-6, see FIG. 21). For production of CDNF 1 μg of plasmid DNA (expression vector) was used for transfection of the $4 \times 10^6$ CHOEBNALT85 suspension cells. 48 hours after transfection 700 μg/ml of G418 is added to the growth medium. Duration of G418 selection depends on transfection efficiency and rate of toxicity of protein of interest to the appropriate cell line. In most cases 75-80% transfection efficiency is achieved with CHOEBNALT85 suspension cells. After G418 selection production phase (7 days) is performed. Production phase is started with $6 \times 10^6$ cells/ml, temperature is shifted to 30° C., feed is added to the cell culture (FIG. 7). After production phase supernatant is clarified and frozen prior the use. Similarly to CDNF production, there was no significant difference between bovine DNaseI production started from transfected cells or from production cell bank (data not shown).

Figure 8:
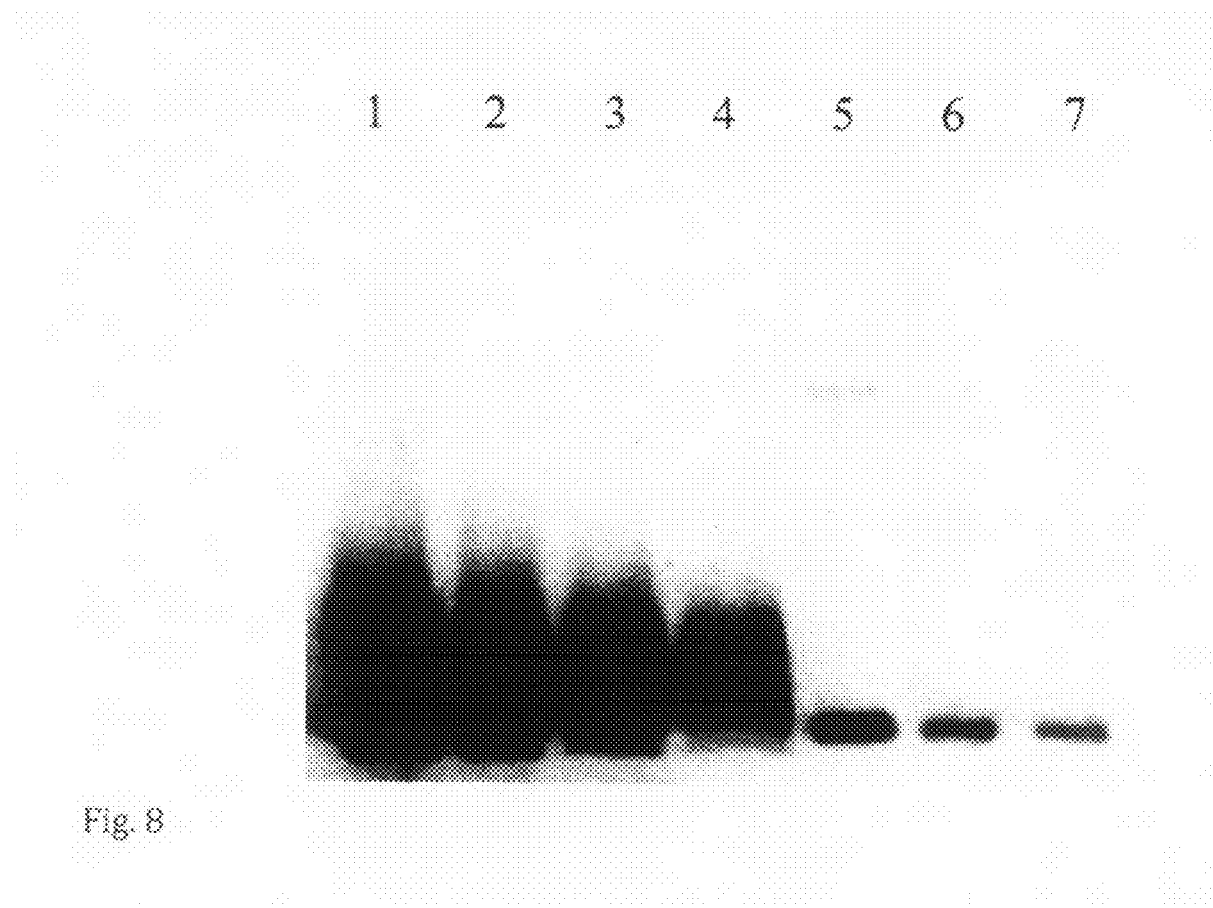
FIG. 8. Production of Bovine DNaseI in CHOEBNALT85 Cells after Selection of Plasmid-Positive Cells 1. CHOEBNALT85 [pQMCF-CMV-0.2-DNaseI] culture supernatant (14 μl) 2. CHOEBNALT85 [pQMCF-CMV-0.2-DNaseI] culture supernatant (7 μl) 3. CHOEBNALT85 [pQMCF-CMV-0.2-DNaseI] culture supernatant (3.5 μl) 4. CHOEBNALT85 [pQMCF-CMV-0.2-DNaseI] culture supernatant (1.25 μl) 5. "Ambion" DNaseI (0.25 μg) 6. "Ambion" DNaseI (0.125 μg) 7. "Ambion" DNaseI (0.0625 μg)

For selection of plasmid-containing cells 48 h after transfection G418 (700 μg/ml) was added and cells were grown additionally 10 days. 4 vials ($1 \times 10^7$) cells were frozen as expression cell bank. For production of bovine DNaseI in 200 ml volume 1 vial from expression cell bank was taken and grown 6 days to reach to the 200 ml volume ($4 \times 10^6$ cells/ml). After 7-days of production phase the viability of culture was 83% containing $8 \times 10^6$ cells/ml. Supernatant of the cells was clarified, frozen down and analyzed for DNaseI expression level using semi-quantitative Western-Blot method (FIG. 8).

Figure 9:
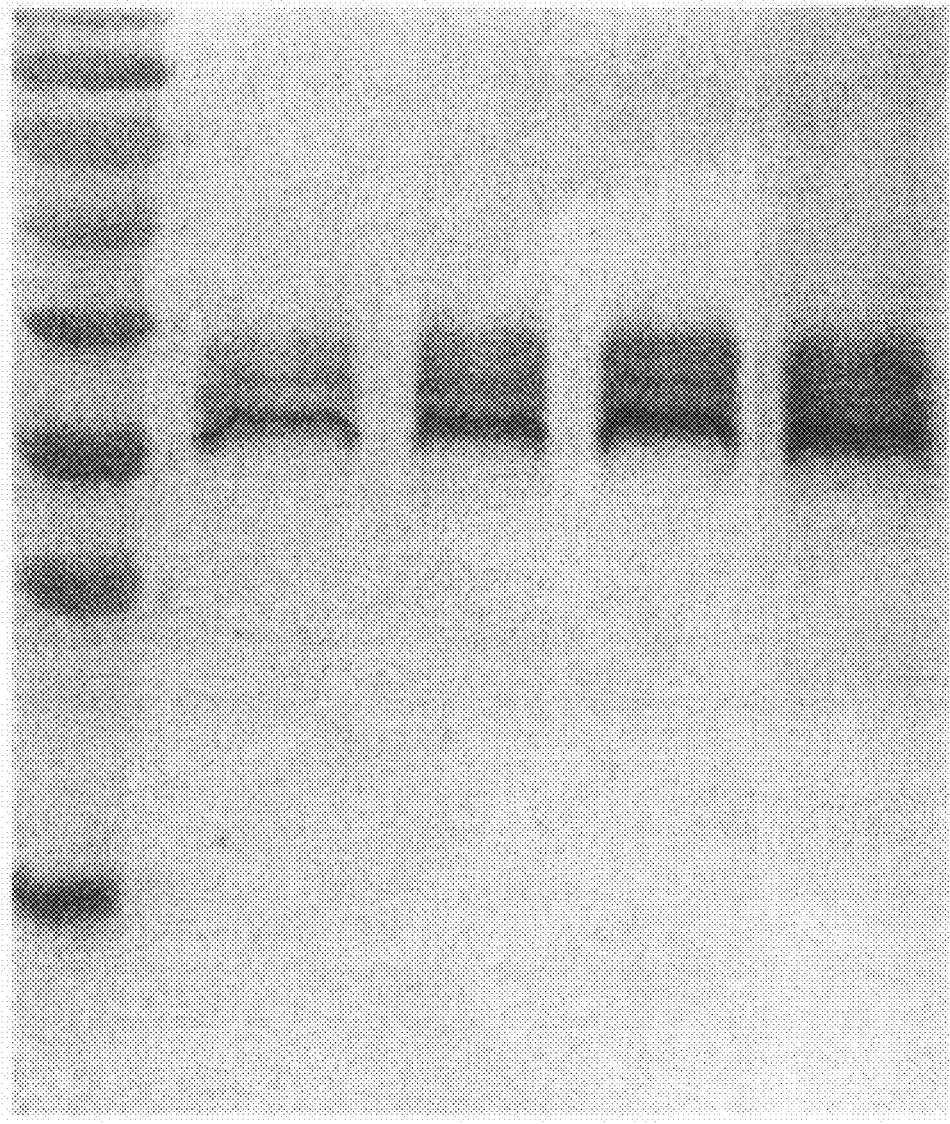
FIG. 9. Production of Bovine DNaseI by CHOEBNALT85 Cells Started from Newly Transfected Cells or from Production Cell Bank.

Bovine DNaseI expression by cells taken from expression cell bank is comparable to the expression started by newly transfected CHOEBNALT85 cells (FIG. 9).

Stability of pQMCF expression vectors. We have analyzed by Southern-Blot analysis the stability of plasmid in CHOEBNALT85 suspension cell line 48 h after transfection, before production phase and during production. As shown in FIG. 10, new generation pQMCF vectors are much more stable (FIG. 10, Lines 5-26) as compared to pFRG-type plasmid (FIG. 10, Lines 1-4).

Example 4

Examples of Cell-Based Assays (CBA) Generated by QMCF Plasmids and Cell Lines

We developed adherent cell lines based on U2OS, CHO and HEK293 stably expressing Mouse Polyomavirus (PyV) Large-T antigen for initiation of plasmid replication during S-phase of the cell cycle and Epstein-Barr Virus (EBV) EBNA-1 protein for segregation/partitioning of the extrachromosomal plasmid into the daughter cells during cell division. Adherent, monolayer growth of cell culture allows use of these cell lines as cell-based assay test-systems. New generation pQMCF expression plasmids (pQMCF-1 to pQMCF-6, as shown in FIG. 21) are suitable for this approach. cDNA of target protein is inserted into the pQMCF expression vector, adherent QMCF cell lines are transfected by electroporation, plasmid-containing cells are selected by G418 and protein expression or translocation is detected. For detection target proteins are fused with EGFP* (in the case of target-protein-EGFP fusion systems) or by N- or C-terminal epitope-tag sequences. Appropriate fluorescent monoclonal anti-epitope-tag antibodies are used for protein localization visualization. We have developed 4 different epitope-tags, which allow detecting more than one target-protein localization within same cell-based assay simultaneously. Detection of more than one target-protein within same cell gives good possibility to reconstruct signal-pathways and investigate possible side effects of drug candidate.

Epitope-tag sequences used for target-protein detection:

```
6G5     - TVKAKLLSVE              (SEQ ID NO: 20)

5E11    - SSTSSDFRDR              (SEQ ID NO: 21)

HIV-1 p24 - TPQDLNTMLNTVGGH       (SEQ ID NO: 22)

9A2.1   - LSSKAVNHIRSVWKDLLEDT    (SEQ ID NO: 23)
```

A. Endothelin A Receptor (ETAR-EGFP) Translocation Assay.

Adherent CHOEBNALT cells were transfected with expression plasmid containing ETAR-EGFP fusion protein under the control of CMV promoter. 800 ng of expression plasmid was transfected into $4\times10^6$ CHOEBNALT adherent cells. 48 hours after transfection 400 μg/ml of G418 is added to the growth medium. Duration of G418 selection depends on transfection efficiency and rate of toxicity of target protein into the appropriate cell line. After G418 selection cells were treated with 300 nM endothelin (ETAR internalization effector) and visualized by fluorescent microscopy (FIG. 11).

B. Endothelin A Receptor ETAR-5E11 Tag) Detection Using Fluorescent Dye Labelled Antibody Directed Against Epitope Tag.

Adherent U2OSEBNALTD3 cells were transfected with expression ETAR-5E11 tag-fusion plasmid. 800 ng of expression plasmid was transfected into $4\times10^6$ CHOEBNALT adherent cells. 48 hours after transfection cells were fixed and permeabilized and IF (immunofluorescence) analysis was performed using Thermo Scientific DyLight488 fluorescent dye conjugated anti 5E11 epitope-tag antibody (FIG. 12).

Example 5

Expression of Virus Like Particles (VLP-s)

Expression of viral envelope or capside proteins results self-assembly of virus like particles (VLP-s). VLPs could be produced in different cell systems, including mammalian, insect, yeast and plant cells. One good possibility to produce membrane proteins in functional and correct conformational manner is expression of these proteins in composition of virus like particles (VLP-s). VLP-s could be used for different approaches e.g. vaccine development, investigation of receptor functions and also for expression of different membrane proteins.

We have constructed expression vectors for production of membrane-bound proteins eg. ion-channels, receptors, viral glycoproteins in composition of gag protein-based VLP-s using new generation pQMCF vectors (FIGS. 21, 23) and the mammalian cell lines as described in this application. All expression vectors for production of VLP-s carry maintenance, replication and antibiotic selection elements as described above.

Two different types of expression vectors are constructed: single- or two-expression cassettes-containing vectors. (FIG. 13A and B respectively). Also, two different types of gag proteins, HIV-1 and MLV (murine leukemia virus) gag proteins are used for formation of VLP-s.

As it is shown in FIG. 9, strong CMV promoter is used for expression of gag protein or in the case of single expression cassette-containing vector also protein of interest expression. Gag and protein of interest expression is divided in single-expression cassette vector by foot-and-mouth disease virus (FMDV) 2A peptide (FIG. 10A). As expression of ion channels and receptor proteins is sometimes toxic to the cells, we use two "weaker" RSV-LTR or hEF1α-HTLV promoters for protein of interest expression.

A. Expression of Endothelin A Receptor (ETAR) in HIV-1 gag Protein-Based VLP-s

Production of VLP-s by Use of Novel Constructs, Vectors and Cell Lines of this Disclosure We found in our experiments that for production of VLP-s HEK293-based cell line 293EBNALT75 gives more stable VLP expression than CHOEBNALT85 cell line. For production of VLP-s 1 μg of plasmidial DNA (expression plasmid) for transfection of the $4\times10^6$ 293EBNALT75 cells. 48 hours after transfection 10 μg/ml (293EBNALT75) G418 is added to the growth medium. Duration of G418 selection depends on transfection efficiency and rate of toxicity of protein of interest to the appropriate cell line. In most cases 30-50% transfection efficiency is achieved with 293EBNALT75 cells. After G418 selection production phase (3-5 days) is performed. Production phase is started with $6\times10^6$ cells/ml, temperature is shifted to 30° C. After production phase supernatant is clarified and VLP-s are purified by ultracentrifugation or precipitation and gel-filtration.

In FIG. 14, production of ETAR-pseudotyped HIV-gag based VLP-s is shown. ETAR protein (P25101) is tagged by 5E11 epitope tag (U.S. Pat. No. 7,189,540) and appropriate antibody was used for detection of protein expression. VLP-s are produced by 293EBNALT75 cell line in small, 20 ml medium volume. Compared to cells expressing only ETAR protein (Line 2), type II ETAR-pseudotyped VLP-s are formed efficiently (Line 3, FIG. 14).

Example 6

Production of Recombinant Monoclonal Antibodies

All expression vectors for production of monoclonal antibodies carry maintenance, replication and antibiotic selection elements as described above. Antibody expression vectors contain two separate expression cassettes (FIG. 24). All DNA elements (promoters, introns, polyA sequences) in expression cassettes were chosen as different as possible.

Two different types of antibody expression vectors are constructed: single- or two-expression cassettes-containing vectors. (FIG. 15 A and B respectively).

A. Expression of Partially Humanized (Chimeric) Tyrosinase A Antibodies

We have validated methods for generation of production system for recombinant murine- or partially humanized (chimeric) tyrosinase A antibodies. cDNA-s encoding variable regions of IgG1 antibody light- or heavy chains were generated from appropriate hybridoma culture and recombinant IgG1 antibody-expressing vectors were generated fusing antibody variable regions-encoding DNA fragments to the antibody constant regions. Recombinant antibody expression plasmids were transfected into the CHOEBNALT85 cells and antibodies were produced, purified and in vitro antigene-binding affinity was measured in comparison with tyrosinase A antibody expressed and purified from hybridoma culture.

For production of partially humanized (chimeric) tyrosinase A antibody 1 μg of plasmid DNA (expression vector) was used for transfection of the 4×106 CHOEBNALT85 cells. 48 hours after transfection 700 μg/ml of G418 is added to the growth medium. Duration of G418 selection depends on transfection efficiency and rate of toxicity of protein of interest to the appropriate cell line. In most cases 75-80% transfection efficiency is achieved with CHOEBNALT85 cells. After G418 selection production phase (6 days) is performed. Production phase is started with 6×10$^6$ cells/ml, temperature is shifted to 30° C., feed is added to the cell culture (FIG. 16). After production phase supernatant is clarified and frozen prior usage.

In FIG. 18 expression of partially humanized (chimeric) tyrosinase A antibody was verified by Western-Blot analysis. In FIG. 16 expression of partially humanized (chimeric) tyrosinase A antibody was analyzed from different time points of growth. As shown in FIG. 18, significantly larger amount of monoclonal antibody is detected at the end of production (FIG. 18, Line 4).

Example 7

Stability of pQMME in U2OSEBNALTE2 Cell Lines

Southern-Blot Analysis of pQMME Plasmid in U2OSEBNALTE2 Cell Lines

We have analyzed stability of plasmid pQMME (FIG. 22) in U2OSEBNALTE2 cell line. For construction of U2OSEBNALTE2 cell line BPV E2 protein-expressing concatamer is inserted into U2OSEBNALTD3 cell line. EGFP-expression plasmid pQMME-1-EGFP is transferred into the U2OSEBNALTE2 cell line and cells are grown under the G418 selection constantly passaging for more than 8 weeks. Samples for plasmid analyses were taken 48 hours, 32 days and 52 days after transfection. As shown in FIG. 25, plasmid remains stable during all experiment.

REFERENCES

1. Abroi, A., I. Ilves, S. Kivi, and M. Ustav. 2004. Analysis of chromatin attachment and partitioning functions of bovine papillomavirus type 1 E2 protein. Journal of Virology 78:2100-13.
2. Ilves, I., S. Kivi, and M. Ustav. 1999. Long-term episomal maintenance of bovine papillomavirus type 1 plasmids is determined by attachment to host chromosomes, which is mediated by the viral E2 protein and its binding sites. Journal of Virology 73:4404-12.
3. Kurg, R., J. Parik, E. Juronen, T. Sedman, A. Abroi, I. Liiv, U. Langel, and M. Ustav. 1999. Effect of bovine papillomavirus E2 protein-specific monoclonal antibodies on papillomavirus DNA replication. Journal of Virology 73:4670-7.
4. Mannik, A., M. Piirsoo, K. Nordstrom, E. Ustav, B. Vennstrom, and M. Ustav. 2003. Effective generation of transgenic mice by Bovine papillomavirus type 1 based self-replicating plasmid that is maintained as extrachromosomal genetic element in three generations of animals. Plasmid 49:193-204.
5. Morgenstern, J. P., and H. Land. 1990. Advanced mammalian gene transfer: high titre retroviral vectors with multiple drug selection markers and a complementary helper-free packaging cell line. Nucleic Acids Research 18:3587-96.
6. Nilsson, M., M. Forsberg, Z. Y. You, G. Westin, and G. Magnusson. 1991. Enhancer effect of bovine papillomavirus E2 protein in replication of polyomavirus DNA. Nucleic Acids Research 19:7061-5.
7. Piirsoo, M., E. Ustav, T. Mandel, A. Stenlund, and M. Ustav. 1996. Cis and trans requirements for stable episomal maintenance of the BPV-1 replicator. EMBO Journal 15:1-11.
8. Tyndall, C., G. La Mantia, C. M. Thacker, J. Favaloro, and R. Kamen. 1981. A region of the polyoma virus genome between the replication origin and late protein coding sequences is required in cis for both early gene expression and viral DNA replication. Nucleic Acids Research 9:6231-50.
9. Ustav E, Ustav M, Szymanski P, Stenlund A. 1993 The bovine papillomavirus origin of replication requires a binding site for the E2 transcriptional activator. Proc. Natl. Acad. Sci. USA 90 (3): 898-902
10. Ustav, M., and A. Stenlund. 1991. Transient replication of BPV-1 requires two viral polypeptides encoded by the E1 and E2 open reading frames. EMBO Journal 10:449-57.
11. Wade-Martins, R., J. Frampton, and M. R. James. 1999. Long-term stability of large insert genomic DNA episomal shuttle vectors in human cells. Nucleic
12. Guo, Z. S., and M. L. DePamphilis. 1992. Specific transcription factors stimulate simian virus 40 and polyomavirus origins of DNA replication. Mol Cell Biol 12:2514-24. Acids Research 27:1674-82.
13. Hung, S. C., M. S. Kang, and E. Kieff. 2001. Maintenance of Epstein-Barr virus (EBV) oriP-based episomes requires EBV-encoded nuclear antigen-1 chromosome-binding domains, which can be replaced by high-mobility group-I or histone H1. Proceedings of the National Academy of Sciences of the United States of America 98:1865-70.

What is claimed is:

1. An expression system to provide extended episomal replication of hybrid plasmid in eukaryotic cell lines, said system comprising:
   a. a vector having a polyoma virus core origin consisting of SEQ ID NO:2, an FR element of EBV, a selection marker, and a gene of interest operably linked within an expression cassette expressing the gene in a eukaryotic cell; and
   b. a compatible mammalian cell line, where the vector is expressed, said cell line constitutively expressing EBV EBNA 1 protein and PyV LT protein either in presence or in absence of selective pressure.

2. The system according to claim 1, wherein the FR element comprises 21 EBNA 1 binding sites.

3. The system according to claim 2, wherein at least one of the EBNA 1 binding sites consist of a sequence selected from the group consisting of SEQ ID NOs 3, 4 and 6.

4. The system according to claim 2, wherein the FR element consists of SEQ ID NO: 1.

5. The system according to claim 1, wherein the cell line is of mouse, hamster or human origin.

6. The system according to claim 1, wherein the gene of interest encodes a protein for pharmaceutical use.

7. The system according to claim 6, wherein the protein is a monoclonal antibody.

8. The system according to claim 6, wherein the protein is virus envelope or capside protein.

9. The system according to claim 6, wherein the protein is fused to an epitope-tag.

10. The system according to claim 9, wherein the epitope tag has an amino acid sequence selected from the group consisting of SEQ ID NO: 20, 21, 22, and 23.

11. An expression plasmid for use in mammalian cell expression system, said vector comprising:
    a. a polyoma virus core origin consisting of SEQ ID NO:2;
    b. an FR element of Eppstein Barr Virus (EBV);
    c. a selection marker; and
    d. a gene of interest in an expression cassette expressing in a eukaryotic cell.

12. The expression plasmid of claim 11, where the FR element consists of SEQ ID NO:1.

13. The expression plasmid of claim 11, wherein the expression cassette comprises a multicloning site for insertion of the gene of interest, and a promoter.

14. The expression plasmid of claim 13, wherein the promoter is selected from the group consisting of Cytomegalovirus immediate early (CMV)-promoter, EF1α, EF1α-HTLC, heIF 4a, β-actin, and Rous Sarcoma Virus proviral Long Terminal Repeat (RSV-LTR)-promoter.

15. The expression plasmid of claim 11, wherein the gene of interest encodes protein for pharmaceutical use.

16. The expression plasmid of claim 15, wherein the protein is monoclonal antibody.

17. The expression plasmid of claim 15, wherein the protein is virus envelope or capside protein.

18. The expression plasmid of claim 15, where the protein is fused to an epitope tag.

19. The expression plasmid of claim 18, where the epiotope tag has an amino acid sequence selected from the group consisting of SEQ ID NO: 20, 21, 22, and 23.

20. A cell line comprising the expression plasmid of claim 11.

* * * * *